(12) United States Patent
Ang et al.

(10) Patent No.: US 12,366,920 B2
(45) Date of Patent: Jul. 22, 2025

(54) SYSTEMS AND METHODS FOR GESTURE INFERENCE USING TRANSFORMATIONS

(71) Applicant: Pison Technology, Inc., Boston, MA (US)

(72) Inventors: Dexter Ang, Boston, MA (US); David Cipoletta, Boston, MA (US); Xiaofeng Tan, Boston, MA (US); Matt Fleury, Boston, MA (US); Dylan Pollack, Boston, MA (US)

(73) Assignee: Pison Technology, Inc., Boston, MA (US)

( * ) Notice: Subject to any disclaimer, the term of this patent is extended or adjusted under 35 U.S.C. 154(b) by 354 days.

(21) Appl. No.: 18/161,053

(22) Filed: Jan. 28, 2023

(65) Prior Publication Data

US 2024/0103623 A1 Mar. 28, 2024

Related U.S. Application Data

(63) Continuation-in-part of application No. 17/935,480, filed on Sep. 26, 2022, now Pat. No. 11,914,791.

(51) Int. Cl.
*G06F 3/01* (2006.01)
*G06N 5/04* (2023.01)

(52) U.S. Cl.
CPC .............. *G06F 3/015* (2013.01); *G06F 3/017* (2013.01); *G06N 5/04* (2013.01)

(58) Field of Classification Search
CPC .......... G06F 3/015; G06F 3/017; G06F 1/163; G06F 3/014; G06F 3/016; G06N 5/04; A61B 5/1114; A61B 5/332; A61B 5/681; A61B 5/0022; G04G 21/025
See application file for complete search history.

(56) References Cited

U.S. PATENT DOCUMENTS

| | | |
|---|---|---|
| 1,007,079 A | 10/1911 | Engberg |
| 1,062,090 A | 5/1913 | Flint |
| 1,078,880 A | 11/1913 | Rusnak |
| 1,411,995 A | 4/1922 | Dull |
| 3,408,133 A | 10/1968 | Lee |
| 3,620,208 A | 11/1971 | Higley et al. |
| 3,712,716 A | 1/1973 | Cornsweet et al. |
| 3,880,146 A | 4/1975 | Everett et al. |
| 4,055,168 A | 10/1977 | Miller et al. |
| 4,427,912 A | 1/1984 | Bui et al. |
| 4,602,639 A | 7/1986 | Hoogendoorn et al. |
| 4,705,708 A | 11/1987 | Briggs et al. |
| 4,751,505 A | 6/1988 | Williams et al. |
| 4,757,714 A | 7/1988 | Purdy et al. |
| 4,978,213 A | 12/1990 | Hage |
| 4,987,410 A | 1/1991 | Berman et al. |
| 5,003,978 A | 4/1991 | Dunseath |

(Continued)

*Primary Examiner* — Matthew A Eason
*Assistant Examiner* — Chayce R Bibbee
(74) *Attorney, Agent, or Firm* — Scale LLP

(57) ABSTRACT

Disclosed are methods, systems and non-transitory computer readable memory for gesture inference. For instance, a first method may include computer vision to train and/or infer gesture inferences. For instance, a second method may include using transformations to data and/or ML models to address inter/intra-session variability of sensor data. For instance, a third method may include using ML model selection to select a ML model to address inter/intra-session variability of sensor data.

20 Claims, 18 Drawing Sheets

(56) References Cited

U.S. PATENT DOCUMENTS

| | | |
|---|---|---|
| D322,227 S | 12/1991 | Warhol |
| 5,081,852 A | 1/1992 | Cox |
| 5,103,323 A | 4/1992 | Magarinos et al. |
| 5,217,014 A | 6/1993 | Hahn et al. |
| 5,231,674 A | 7/1993 | Cleveland et al. |
| 5,251,189 A | 10/1993 | Thorp |
| 5,287,859 A | 2/1994 | John |
| D348,660 S | 7/1994 | Parsons |
| 5,445,869 A | 8/1995 | Ishikawa et al. |
| 5,467,104 A | 11/1995 | Furness, III et al. |
| 5,482,051 A | 1/1996 | Reddy et al. |
| 5,488,957 A | 2/1996 | Frey et al. |
| 5,544,268 A | 8/1996 | Bischel et al. |
| 5,589,956 A | 12/1996 | Morishima et al. |
| 5,596,339 A | 1/1997 | Furness, III et al. |
| 5,605,059 A | 2/1997 | Woodward |
| 5,619,373 A | 4/1997 | Meyerhofer et al. |
| 5,625,577 A | 4/1997 | Kunii et al. |
| 5,660,177 A | 8/1997 | Faupel et al. |
| 5,696,521 A | 12/1997 | Robinson et al. |
| 5,719,561 A | 2/1998 | Gonzales |
| 5,818,359 A | 10/1998 | Beach |
| 5,823,957 A | 10/1998 | Faupel et al. |
| 5,886,822 A | 3/1999 | Spitzer |
| 5,986,811 A | 11/1999 | Wohlstadter |
| 6,005,548 A | 12/1999 | Latypov et al. |
| 6,008,781 A | 12/1999 | Furness, III et al. |
| 6,009,210 A | 12/1999 | Kang |
| 6,027,216 A | 2/2000 | Guyton et al. |
| 6,032,530 A | 3/2000 | Hock |
| 6,032,560 A | 3/2000 | Puchovsky |
| 6,128,003 A | 10/2000 | Smith et al. |
| 6,147,807 A | 11/2000 | Droessler et al. |
| 6,151,167 A | 11/2000 | Melville |
| 6,184,847 B1 | 2/2001 | Fateh et al. |
| 6,238,338 B1 | 5/2001 | DeLuca et al. |
| 6,244,873 B1 | 6/2001 | Hill et al. |
| 6,255,537 B1 | 7/2001 | Hayashi et al. |
| 6,353,503 B1 | 3/2002 | Spitzer et al. |
| 6,411,843 B1 | 6/2002 | Zarychta |
| 6,433,907 B1 | 8/2002 | Lippert et al. |
| 6,456,438 B1 | 9/2002 | Lee et al. |
| 6,470,893 B1 | 10/2002 | Boesen |
| 6,515,781 B2 | 2/2003 | Lewis et al. |
| 6,525,310 B2 | 2/2003 | Dunfield |
| 6,529,331 B2 | 3/2003 | Massof et al. |
| 6,583,772 B1 | 6/2003 | Lewis et al. |
| 6,658,287 B1 | 12/2003 | Litt et al. |
| 6,666,825 B2 | 12/2003 | Smith et al. |
| 6,673,027 B2 | 1/2004 | Fischer |
| 6,681,031 B2 | 1/2004 | Cohen et al. |
| 6,719,693 B2 | 4/2004 | Richard |
| 6,720,984 B1 | 4/2004 | Jorgensen et al. |
| 6,724,012 B2 | 4/2004 | Kimura |
| 6,731,434 B1 | 5/2004 | Hua et al. |
| 6,747,785 B2 | 6/2004 | Chen et al. |
| 6,764,012 B2 | 7/2004 | Connolly et al. |
| 6,774,885 B1 | 8/2004 | Even-Zohar |
| 6,795,221 B1 | 9/2004 | Urey |
| 6,807,438 B1 | 10/2004 | Re et al. |
| 6,830,344 B2 | 12/2004 | Reho et al. |
| 6,880,364 B1 | 4/2005 | Vidolin et al. |
| 6,924,476 B2 | 8/2005 | Wine et al. |
| 6,937,221 B2 | 8/2005 | Lippert et al. |
| 6,972,734 B1 | 12/2005 | Ohshima et al. |
| 6,984,208 B2 | 1/2006 | Zheng |
| 6,999,238 B2 | 2/2006 | Glebov et al. |
| 7,054,045 B2 | 5/2006 | McPheters et al. |
| 7,061,450 B2 | 6/2006 | Bright et al. |
| 7,071,594 B1 | 7/2006 | Yan et al. |
| 7,082,393 B2 | 7/2006 | Lahr |
| 7,106,519 B2 | 9/2006 | Aizenberg et al. |
| 7,145,722 B2 | 12/2006 | Dutta |
| 7,190,508 B2 | 3/2007 | Yang |
| 7,193,758 B2 | 3/2007 | Wiklof et al. |
| 7,206,625 B2 | 4/2007 | Kurtz et al. |
| 7,209,538 B2 | 4/2007 | Sukovic et al. |
| 7,232,071 B2 | 6/2007 | Lewis et al. |
| 7,333,090 B2 | 2/2008 | Tanaka et al. |
| 7,369,321 B1 | 5/2008 | Ren et al. |
| 7,400,439 B2 | 7/2008 | Holman |
| 7,486,255 B2 | 2/2009 | Brown et al. |
| 7,542,210 B2 | 6/2009 | Chirieleison |
| 7,545,571 B2 | 6/2009 | Garoutte et al. |
| 7,580,007 B2 | 8/2009 | Brown et al. |
| 7,596,393 B2 | 9/2009 | Jung et al. |
| 7,619,807 B2 | 11/2009 | Baek et al. |
| 7,623,560 B2 | 11/2009 | El-Ghoroury et al. |
| 7,640,007 B2 | 12/2009 | Chen et al. |
| 7,724,210 B2 | 5/2010 | Sprague et al. |
| 7,747,301 B2 | 6/2010 | Cheng et al. |
| 7,791,810 B2 | 9/2010 | Powell |
| 7,804,624 B2 | 9/2010 | Cernasov |
| 7,860,587 B2 | 12/2010 | Berg et al. |
| 7,874,666 B2 | 1/2011 | Xu et al. |
| 7,945,338 B2 | 5/2011 | Fuller et al. |
| 7,952,809 B2 | 5/2011 | Takai |
| 7,954,953 B2 | 6/2011 | Sprague |
| 8,098,265 B2 | 1/2012 | El-Ghoroury et al. |
| 8,107,147 B2 | 1/2012 | Hudman et al. |
| 8,170,656 B2 | 5/2012 | Tan et al. |
| 8,177,361 B2 | 5/2012 | Sessner et al. |
| 8,228,315 B1 | 7/2012 | Starner et al. |
| 8,279,716 B1 | 10/2012 | Gossweiler, III et al. |
| 8,289,162 B2 | 10/2012 | Mooring et al. |
| 8,293,354 B2 | 10/2012 | Fu et al. |
| 8,386,026 B2 | 2/2013 | Fink et al. |
| 8,444,559 B2 | 5/2013 | Fink et al. |
| 8,447,704 B2 | 5/2013 | Tan et al. |
| 8,467,133 B2 | 6/2013 | Miller |
| 8,471,967 B2 | 6/2013 | Miao et al. |
| 8,477,425 B2 | 7/2013 | Border et al. |
| 8,482,859 B2 | 7/2013 | Border et al. |
| 8,497,767 B2 | 7/2013 | Hollis, Jr. |
| 8,508,830 B1 | 8/2013 | Wang |
| 8,508,851 B2 | 8/2013 | Miao et al. |
| 8,510,244 B2 | 8/2013 | Carson et al. |
| 8,519,950 B2 | 8/2013 | Radivojevic et al. |
| 8,553,910 B2 | 10/2013 | Dong et al. |
| 8,581,856 B2 | 11/2013 | Benko et al. |
| 8,619,049 B2 | 12/2013 | Harrison et al. |
| 8,672,752 B2 | 3/2014 | Gagner et al. |
| 8,694,084 B2 | 4/2014 | Sullivan et al. |
| 8,725,842 B1 | 5/2014 | Al-Nasser |
| 8,743,145 B1 | 6/2014 | Price |
| 8,754,829 B2 | 6/2014 | Lapstun |
| 8,773,599 B2 | 7/2014 | Saeedi et al. |
| 8,781,221 B2 | 7/2014 | Ding et al. |
| 8,798,710 B2 | 8/2014 | Chi |
| 8,854,724 B2 | 10/2014 | El-Ghoroury et al. |
| 8,872,853 B2 | 10/2014 | Sugden et al. |
| 8,892,479 B2 | 11/2014 | Tan et al. |
| 8,894,484 B2 | 11/2014 | Latta et al. |
| 8,912,017 B2 | 12/2014 | El-Ghoroury et al. |
| 8,928,969 B2 | 1/2015 | Alpaslan et al. |
| 8,941,559 B2 | 1/2015 | Bar-Zeev et al. |
| 8,947,783 B2 | 2/2015 | Gupta et al. |
| 8,994,718 B2 | 3/2015 | Latta et al. |
| 9,069,164 B2 | 6/2015 | Starner et al. |
| 9,071,209 B1 | 6/2015 | Harrison |
| 9,092,664 B2 | 7/2015 | Forutanpour et al. |
| 9,097,890 B2 | 8/2015 | Miller et al. |
| 9,110,505 B2 | 8/2015 | Mastandrea, Jr. |
| 9,134,535 B2 | 9/2015 | Dobschal et al. |
| 9,164,290 B2 | 10/2015 | Robbins et al. |
| 9,170,674 B2 | 10/2015 | Forutanpour et al. |
| 9,179,126 B2 | 11/2015 | El-Ghoroury et al. |
| 9,184,722 B2 | 11/2015 | Bakalski |
| 9,218,058 B2 | 12/2015 | Bress et al. |
| 9,223,139 B2 | 12/2015 | Kress et al. |
| 9,244,539 B2 | 1/2016 | Venable et al. |
| 9,274,595 B2 | 3/2016 | Reitan |
| 9,274,608 B2 | 3/2016 | Katz et al. |
| 9,278,453 B2 | 3/2016 | Assad |

(56) References Cited

U.S. PATENT DOCUMENTS

| | | |
|---|---|---|
| 9,299,248 B2 | 3/2016 | Lake et al. |
| 9,306,534 B2 | 4/2016 | Chung |
| 9,317,128 B2 | 4/2016 | Minnen et al. |
| 9,319,741 B2 | 4/2016 | Igoe et al. |
| 9,330,666 B2 | 5/2016 | Alameh et al. |
| 9,335,602 B2 | 5/2016 | Chung et al. |
| 9,345,609 B2 | 5/2016 | Hyde et al. |
| 9,351,653 B1 | 5/2016 | Harrison |
| 9,372,535 B2 | 6/2016 | Bailey et al. |
| 9,405,124 B2 | 8/2016 | Hirsch et al. |
| 9,451,162 B2 | 9/2016 | Hoff et al. |
| 9,452,287 B2 | 9/2016 | Rosenbluth et al. |
| 9,483,123 B2 | 11/2016 | Aleem et al. |
| 9,501,145 B2 | 11/2016 | Poupyrev et al. |
| 9,529,191 B2 | 12/2016 | Sverdrup et al. |
| 9,538,182 B2 | 1/2017 | Mishourovsky et al. |
| 9,545,221 B2 | 1/2017 | Adhikari et al. |
| 9,545,567 B2 | 1/2017 | Han et al. |
| 9,565,410 B2 | 2/2017 | Huai |
| 9,569,001 B2 | 2/2017 | Mistry et al. |
| 9,600,030 B2 | 3/2017 | Bailey et al. |
| 9,632,315 B2 | 4/2017 | Smith et al. |
| 9,651,784 B2 | 5/2017 | Osterhout |
| 9,652,032 B2 | 5/2017 | Mitchell |
| 9,720,515 B2 | 8/2017 | Wagner et al. |
| 9,727,790 B1 | 8/2017 | Vaziri |
| 9,898,869 B2 | 2/2018 | Shapira et al. |
| 9,916,006 B2 | 3/2018 | Maltz |
| 9,921,687 B2 | 3/2018 | Yang et al. |
| 9,931,230 B2 | 4/2018 | Sikdar et al. |
| 9,933,621 B2 | 4/2018 | Hirano et al. |
| 9,981,193 B2 | 5/2018 | Adams et al. |
| 10,019,634 B2 | 7/2018 | Vaziri |
| 10,054,503 B2 | 8/2018 | Ma et al. |
| 10,061,387 B2 | 8/2018 | Toney et al. |
| 10,070,799 B2 | 9/2018 | Ang et al. |
| 10,080,950 B2 | 9/2018 | Kelley |
| 10,114,468 B2 | 10/2018 | Ette et al. |
| 10,120,444 B2 | 11/2018 | Nekozuka et al. |
| 10,178,218 B1 | 1/2019 | Vadodaria |
| 10,185,416 B2 | 1/2019 | Mistry et al. |
| 10,234,941 B2 | 3/2019 | Kim et al. |
| 10,234,952 B2 | 3/2019 | Parvarandeh et al. |
| 10,268,888 B2 | 4/2019 | Osterhout et al. |
| 10,295,990 B2 | 5/2019 | Dey, IV et al. |
| 10,338,685 B2 | 7/2019 | Elangovan et al. |
| 10,386,970 B2 | 8/2019 | Harley et al. |
| 10,497,191 B2 | 12/2019 | Hyde et al. |
| 10,511,769 B2 | 12/2019 | Edpalm et al. |
| 10,554,962 B2 | 2/2020 | Perdices-Gonzalez et al. |
| 10,578,882 B2 | 3/2020 | El-Ghoroury et al. |
| 10,593,137 B2 | 3/2020 | Hyde et al. |
| 10,627,860 B2 | 4/2020 | Jacobsen et al. |
| 10,627,914 B2 | 4/2020 | Ang et al. |
| 10,636,218 B2 | 4/2020 | Melo et al. |
| 10,671,160 B2 | 6/2020 | Uscinski et al. |
| 10,671,174 B2 | 6/2020 | Ang et al. |
| 10,684,489 B2 | 6/2020 | Kroll et al. |
| 10,698,603 B2 | 6/2020 | Giusti et al. |
| 10,705,597 B1 | 7/2020 | Morin et al. |
| 10,770,035 B2 | 9/2020 | Giusti et al. |
| 10,838,503 B2 | 11/2020 | Hsu et al. |
| 10,861,242 B2 | 12/2020 | Lacey et al. |
| 10,890,653 B2 | 1/2021 | Giusti et al. |
| 10,902,678 B2 | 1/2021 | Jones et al. |
| 11,093,041 B2 | 8/2021 | Bender et al. |
| 11,106,273 B2 | 8/2021 | Hazra et al. |
| 11,150,737 B2 | 10/2021 | Parizi et al. |
| 11,157,086 B2 | 10/2021 | Cipoletta et al. |
| 11,166,698 B2 | 11/2021 | Takada et al. |
| 11,199,908 B2 | 12/2021 | Cipoletta et al. |
| 11,257,268 B2 | 2/2022 | Miller, IV |
| 11,262,841 B2 | 3/2022 | Davis et al. |
| 11,276,219 B2 | 3/2022 | Wedig et al. |
| 11,367,519 B1 | 6/2022 | Heldman et al. |
| 11,430,175 B2 | 8/2022 | Wade |
| 11,435,886 B1 | 9/2022 | Yavercovski |
| 11,436,823 B1 | 9/2022 | Caulfield et al. |
| 11,448,483 B1 | 9/2022 | Curzan et al. |
| 11,449,150 B2 | 9/2022 | Cipoletta et al. |
| 11,467,670 B2 | 10/2022 | Keller et al. |
| 11,474,604 B2 | 10/2022 | Ang et al. |
| 11,475,642 B2 | 10/2022 | Fan et al. |
| 11,481,030 B2 | 10/2022 | Barachant et al. |
| 11,481,031 B1 | 10/2022 | Anderson et al. |
| 11,514,947 B1 | 11/2022 | Shaburova |
| 11,520,409 B2 | 12/2022 | Kwon et al. |
| 11,529,650 B2 | 12/2022 | Buckland et al. |
| 11,531,395 B2 | 12/2022 | Kappus et al. |
| 11,537,219 B2 | 12/2022 | Borodin et al. |
| 11,543,507 B2 | 1/2023 | Carter et al. |
| 11,546,280 B2 | 1/2023 | Majid et al. |
| 11,550,395 B2 | 1/2023 | Beattie et al. |
| 11,550,432 B2 | 1/2023 | Carter et al. |
| 11,551,374 B2 | 1/2023 | Li et al. |
| 11,553,295 B2 | 1/2023 | Kappus et al. |
| 11,558,325 B2 | 1/2023 | Kozhemiak et al. |
| 11,567,573 B2 | 1/2023 | Berenzweig et al. |
| 11,575,986 B2 | 2/2023 | Manning |
| 11,587,242 B1 | 2/2023 | Giurgica-Tiron et al. |
| 11,627,892 B2 | 4/2023 | Olson et al. |
| 2002/0008854 A1 | 1/2002 | Travis |
| 2002/0009972 A1 | 1/2002 | Amento et al. |
| 2002/0075232 A1 | 6/2002 | Daum et al. |
| 2002/0083164 A1 | 6/2002 | Katayama et al. |
| 2002/0090968 A1 | 7/2002 | Lee et al. |
| 2003/0086135 A1 | 5/2003 | Takeyama |
| 2004/0051392 A1 | 3/2004 | Badarneh |
| 2004/0068409 A1 | 4/2004 | Tanaka et al. |
| 2004/0125076 A1 | 7/2004 | Green |
| 2004/0138935 A1 | 7/2004 | Johnson et al. |
| 2004/0161132 A1 | 8/2004 | Cohen et al. |
| 2005/0212751 A1 | 9/2005 | Marvit et al. |
| 2005/0212767 A1 | 9/2005 | Marvit et al. |
| 2005/0215916 A1 | 9/2005 | Fadem et al. |
| 2005/0280879 A1 | 12/2005 | Gibson et al. |
| 2006/0132383 A1 | 6/2006 | Gally et al. |
| 2006/0152812 A1 | 7/2006 | Woodgate et al. |
| 2006/0167564 A1 | 7/2006 | Flaherty et al. |
| 2007/0083120 A1 | 4/2007 | Cain et al. |
| 2007/0100666 A1 | 5/2007 | Stivoric et al. |
| 2008/0040036 A1 | 2/2008 | Peters et al. |
| 2008/0278447 A1 | 11/2008 | Lin |
| 2008/0300055 A1 | 12/2008 | Lutnick et al. |
| 2009/0009284 A1 | 1/2009 | Sako |
| 2009/0073559 A1 | 3/2009 | Woodgate et al. |
| 2009/0103780 A1 | 4/2009 | Keith et al. |
| 2009/0199900 A1 | 8/2009 | Bita et al. |
| 2009/0265671 A1 | 10/2009 | Sachs et al. |
| 2009/0326406 A1 | 12/2009 | Tan et al. |
| 2009/0327171 A1 | 12/2009 | Tan et al. |
| 2010/0027511 A1 | 2/2010 | Terry |
| 2010/0053151 A1 | 3/2010 | Marti et al. |
| 2010/0106044 A1 | 4/2010 | Linderman |
| 2011/0054360 A1 | 3/2011 | Son et al. |
| 2011/0115887 A1 | 5/2011 | Yoo et al. |
| 2011/0166777 A1 | 7/2011 | Chavakula |
| 2011/0169934 A1 | 7/2011 | Pulluru et al. |
| 2011/0251512 A1 | 10/2011 | Fink et al. |
| 2011/0282231 A1 | 11/2011 | Pradeep et al. |
| 2011/0289456 A1 | 11/2011 | Reville et al. |
| 2011/0301488 A1 | 12/2011 | Schuette et al. |
| 2011/0306859 A1 | 12/2011 | Saldivar et al. |
| 2012/0010090 A1 | 1/2012 | Nakamura et al. |
| 2012/0029399 A1 | 2/2012 | Sankai |
| 2012/0049998 A1 | 3/2012 | Lim et al. |
| 2012/0075173 A1 | 3/2012 | Ashbrook et al. |
| 2012/0075196 A1 | 3/2012 | Ashbrook et al. |
| 2012/0154441 A1 | 6/2012 | Kim |
| 2012/0188158 A1 | 7/2012 | Tan et al. |
| 2012/0195461 A1 | 8/2012 | Inigo |
| 2012/0236201 A1 | 9/2012 | Larsen et al. |
| 2012/0290943 A1 | 11/2012 | Toney et al. |
| 2012/0299962 A1 | 11/2012 | White et al. |

(56) References Cited

U.S. PATENT DOCUMENTS

| | | |
|---|---|---|
| 2012/0320092 A1 | 12/2012 | Shin et al. |
| 2012/0323521 A1 | 12/2012 | Foras et al. |
| 2012/0326948 A1 | 12/2012 | Crocco et al. |
| 2013/0046070 A1 | 2/2013 | Chamayou et al. |
| 2013/0083303 A1 | 4/2013 | Hoover et al. |
| 2013/0138424 A1 | 5/2013 | Koenig et al. |
| 2013/0169536 A1 | 7/2013 | Wexler et al. |
| 2013/0176622 A1 | 7/2013 | Abrahamsson et al. |
| 2013/0225999 A1 | 8/2013 | Banjanin et al. |
| 2013/0227418 A1 | 8/2013 | Sa et al. |
| 2013/0232148 A1 | 9/2013 | Macdonald et al. |
| 2013/0265229 A1 | 10/2013 | Forutanpour et al. |
| 2013/0271679 A1 | 10/2013 | Sakamoto et al. |
| 2013/0285174 A1 | 10/2013 | Sako et al. |
| 2013/0286053 A1 | 10/2013 | Fleck et al. |
| 2013/0317648 A1 | 11/2013 | Assad |
| 2013/0336519 A1 | 12/2013 | Connor |
| 2014/0007008 A1 | 1/2014 | Baca et al. |
| 2014/0028546 A1 | 1/2014 | Jeon et al. |
| 2014/0049417 A1 | 2/2014 | Abdurrahman et al. |
| 2014/0055352 A1 | 2/2014 | Davis et al. |
| 2014/0085177 A1 | 3/2014 | Lyons et al. |
| 2014/0129207 A1 | 5/2014 | Bailey et al. |
| 2014/0139422 A1 | 5/2014 | Mistry et al. |
| 2014/0139576 A1 | 5/2014 | Costa et al. |
| 2014/0152781 A1 | 6/2014 | Nam et al. |
| 2014/0160078 A1 | 6/2014 | Seo et al. |
| 2014/0176417 A1 | 6/2014 | Young et al. |
| 2014/0198034 A1 | 7/2014 | Bailey et al. |
| 2014/0198035 A1 | 7/2014 | Bailey et al. |
| 2014/0198944 A1 | 7/2014 | Forutanpour et al. |
| 2014/0210745 A1 | 7/2014 | Chizeck et al. |
| 2014/0240223 A1 | 8/2014 | Lake et al. |
| 2014/0247154 A1 | 9/2014 | Proud |
| 2014/0249397 A1 | 9/2014 | Lake et al. |
| 2014/0257129 A1 | 9/2014 | Choi et al. |
| 2014/0275823 A1 | 9/2014 | Lane et al. |
| 2014/0282275 A1 | 9/2014 | Everitt et al. |
| 2014/0304646 A1 | 10/2014 | Rossmann |
| 2014/0340304 A1 | 11/2014 | Dewan et al. |
| 2014/0347295 A1 | 11/2014 | Kim et al. |
| 2014/0359540 A1 | 12/2014 | Kelsey et al. |
| 2015/0001987 A1 | 1/2015 | Masaki et al. |
| 2015/0029092 A1 | 1/2015 | Holz et al. |
| 2015/0031299 A1 | 1/2015 | Holman et al. |
| 2015/0062046 A1 | 3/2015 | Cho et al. |
| 2015/0062086 A1 | 3/2015 | Nattukallingal |
| 2015/0072619 A1 | 3/2015 | Abdurrahman et al. |
| 2015/0077326 A1 | 3/2015 | Kramer et al. |
| 2015/0135102 A1 | 5/2015 | Sung et al. |
| 2015/0138086 A1 | 5/2015 | Underkoffler et al. |
| 2015/0138314 A1 | 5/2015 | Vincent |
| 2015/0161371 A1 | 6/2015 | Hoshi et al. |
| 2015/0163345 A1 | 6/2015 | Cornaby et al. |
| 2015/0164435 A1 | 6/2015 | Nagarajan et al. |
| 2015/0182160 A1 | 7/2015 | Kim et al. |
| 2015/0185853 A1 | 7/2015 | Clausen et al. |
| 2015/0215443 A1 | 7/2015 | Heo et al. |
| 2015/0277575 A1 | 10/2015 | Aleem et al. |
| 2015/0293590 A1 | 10/2015 | Lehtiniemi et al. |
| 2015/0301256 A1 | 10/2015 | Takiguchi |
| 2015/0309582 A1* | 10/2015 | Gupta .................... G06F 3/011 345/156 |
| 2015/0323998 A1 | 11/2015 | Kudekar et al. |
| 2015/0324000 A1 | 11/2015 | Park et al. |
| 2015/0332424 A1 | 11/2015 | Kane et al. |
| 2015/0338917 A1 | 11/2015 | Steiner et al. |
| 2015/0362999 A1 | 12/2015 | Kim et al. |
| 2015/0370333 A1 | 12/2015 | Ataee et al. |
| 2016/0002273 A1 | 1/2016 | Blum et al. |
| 2016/0008088 A1 | 1/2016 | Vayser et al. |
| 2016/0026321 A1 | 1/2016 | Yeo et al. |
| 2016/0034032 A1 | 2/2016 | Jeong et al. |
| 2016/0039424 A1 | 2/2016 | Hong et al. |
| 2016/0041580 A1 | 2/2016 | Inoue et al. |
| 2016/0046294 A1 | 2/2016 | Lee et al. |
| 2016/0062320 A1 | 3/2016 | Chung |
| 2016/0077547 A1 | 3/2016 | Aimone et al. |
| 2016/0080888 A1 | 3/2016 | Kreitzer et al. |
| 2016/0091980 A1 | 3/2016 | Baranski et al. |
| 2016/0109861 A1 | 4/2016 | Kim et al. |
| 2016/0135698 A1 | 5/2016 | Baxi et al. |
| 2016/0162176 A1 | 6/2016 | Hwang |
| 2016/0188010 A1 | 6/2016 | Wright et al. |
| 2016/0195928 A1 | 7/2016 | Wagner et al. |
| 2016/0206207 A1 | 7/2016 | Avila et al. |
| 2016/0216768 A1 | 7/2016 | Goetz et al. |
| 2016/0227351 A1 | 8/2016 | Gu et al. |
| 2016/0239128 A1 | 8/2016 | Zhang et al. |
| 2016/0301662 A1 | 10/2016 | Laux et al. |
| 2016/0307447 A1 | 10/2016 | Johnson et al. |
| 2016/0313798 A1 | 10/2016 | Connor |
| 2016/0313801 A1 | 10/2016 | Wagner et al. |
| 2016/0366590 A1 | 12/2016 | Jun et al. |
| 2016/0367138 A1 | 12/2016 | Kim et al. |
| 2017/0003747 A1 | 1/2017 | Carceroni et al. |
| 2017/0010677 A1 | 1/2017 | Roh et al. |
| 2017/0011210 A1 | 1/2017 | Cheong et al. |
| 2017/0031453 A1 | 2/2017 | Presura |
| 2017/0031496 A1 | 2/2017 | Joo et al. |
| 2017/0031697 A1 | 2/2017 | Lee et al. |
| 2017/0055110 A1 | 2/2017 | Tian et al. |
| 2017/0060518 A1 | 3/2017 | Hong et al. |
| 2017/0064219 A1 | 3/2017 | Lin et al. |
| 2017/0075426 A1 | 3/2017 | Camacho Perez et al. |
| 2017/0090583 A1 | 3/2017 | Zamora Esquivel et al. |
| 2017/0123487 A1 | 5/2017 | Hazra et al. |
| 2017/0134086 A1 | 5/2017 | Liu et al. |
| 2017/0164291 A1 | 6/2017 | Ludwig et al. |
| 2017/0177086 A1 | 6/2017 | Yuen et al. |
| 2017/0185759 A1 | 6/2017 | Schmidt et al. |
| 2017/0192665 A1 | 7/2017 | Karmon |
| 2017/0215768 A1 | 8/2017 | Belfiori |
| 2017/0216675 A1 | 8/2017 | Goslin et al. |
| 2017/0308040 A1 | 10/2017 | Chui et al. |
| 2017/0316675 A1 | 11/2017 | Bauer et al. |
| 2017/0337339 A1 | 11/2017 | Cronin et al. |
| 2017/0357329 A1 | 12/2017 | Park et al. |
| 2017/0372268 A1 | 12/2017 | Ilan et al. |
| 2018/0052492 A1 | 2/2018 | Ökvist et al. |
| 2018/0074520 A1 | 3/2018 | Liu et al. |
| 2018/0096609 A1 | 4/2018 | La et al. |
| 2018/0116532 A1 | 5/2018 | Han et al. |
| 2018/0153430 A1 | 6/2018 | Ang et al. |
| 2018/0224936 A1 | 8/2018 | Tumey |
| 2018/0308187 A1 | 10/2018 | Rotem et al. |
| 2018/0329209 A1 | 11/2018 | Nattukallingal |
| 2018/0338720 A1 | 11/2018 | Gupta et al. |
| 2018/0360341 A1 | 12/2018 | Wang et al. |
| 2018/0364810 A1 | 12/2018 | Parshionikar |
| 2019/0011994 A1 | 1/2019 | Belfiori et al. |
| 2019/0094981 A1 | 3/2019 | Bradski et al. |
| 2019/0101991 A1 | 4/2019 | Brennan et al. |
| 2019/0188471 A1 | 6/2019 | Osterhout et al. |
| 2019/0196600 A1 | 6/2019 | Rothberg et al. |
| 2019/0220099 A1 | 7/2019 | Baranski et al. |
| 2019/0243357 A1 | 8/2019 | Qiu et al. |
| 2019/0265802 A1 | 8/2019 | Parshionikar |
| 2019/0324572 A1 | 10/2019 | Tan et al. |
| 2020/0042089 A1 | 2/2020 | Ang et al. |
| 2020/0081560 A1 | 3/2020 | Geller et al. |
| 2020/0103967 A1 | 4/2020 | Bar-Zeev et al. |
| 2021/0088795 A1 | 3/2021 | Cheng et al. |
| 2021/0149483 A1 | 5/2021 | Berardi et al. |
| 2021/0193977 A1 | 6/2021 | Reykhert |
| 2022/0322219 A1 | 10/2022 | Gandhi et al. |
| 2022/0334649 A1 | 10/2022 | Hwang et al. |

* cited by examiner

US 12,366,920 B2

SYSTEMS AND METHODS FOR GESTURE INFERENCE USING TRANSFORMATIONS

CROSS-REFERENCE TO RELATED APPLICATIONS

This application is a continuation-in-part of U.S. patent application Ser. No. 17/935,480, filed Sep. 26, 2022.

TECHNICAL FIELD

Various aspects of the present disclosure relate generally to systems and methods for gesture control using biopotential sensing wearable devices and, more particularly, to systems and methods for gesture inference using computer vision, transformations, or machine learning (ML) model selection.

BACKGROUND

Most machines (or groups of connected machines) have a form of "user interface" through which a user interacts with the machine. The user provides inputs through one or more devices from which the machine interprets the person's intent. The machine provides feedback to the person in response to those inputs, such as by the behavior of the machine or by outputs through one or more devices of the machine or group of machines which present information to the user or perform actions for the user.

Generally, biopotential gesture machine interfaces are configured to classify a user's input (e.g., a gesture of a user's hand or movement of hand and/or arm) and execute an action in accordance with an inferred user input. However, biopotential gesture machine interfaces are subject to inter/intra-session variability. The inter/intra-session variability may make inference more difficult and/or not possible. Thus, one challenge is to overcome inter/intra-session variability and still provide high confidence gesture identification.

Furthermore, machine interfaces are increasingly including multiple different modes of user input. For instance, in some cases, cameras of mobile devices (e.g., of cell phones or XR systems) or fixed devices (e.g., desktop computer or conferencing technology) may also be a source of user input. Handling data from disparate sources (e.g., cameras and biopotential gesture machine interfaces) is another challenge.

The present disclosure is directed to overcoming one or more of these above-referenced challenges.

SUMMARY OF THE DISCLOSURE

According to certain aspects of the disclosure, systems, methods, and computer readable memory are disclosed for gesture control using biopotential sensing wearable devices.

In some cases, a system for gesture inference may include: at least one camera configured to capture video having image(s) of an environment, the image(s) having image timestamps; a wearable device configured to be worn on a portion of an arm of a user, the wearable device comprising: a biopotential sensor, the biopotential sensor being configured to obtain biopotential data indicating electrical signals generated by nerves and muscles in the arm of the user; and a motion sensor, the motion sensor being configured to obtain motion data relating to a motion of the portion of the arm of the user, the biopotential data and/or the motion data having sensor data timestamps; a first machine learning model, the first machine learning model being configured to output a first gesture inference of the user's hand/arm based on a plurality of sets of key-point values determined based on the image(s) of the environment from the video, the first gesture inference indicating a gesture from a plurality of defined gestures; and a second machine learning model, the second machine learning model being configured to output a second gesture inference of the user's hand/arm using a combination at least the biopotential data and the motion data relating to the motion of the portion of the arm of the user. The system may be configured to: obtain the image(s) of the environment from the video; determine a plurality of sets of key-point values, each set of key-point values indicating locations of portions of a hand of the user for an image of the image(s); using the first machine learning model, process the plurality of sets of key-point values to obtain the first gesture inference; based on the image timestamps, assign a first gesture inference timestamp to the first gesture inference; select a subset of the biopotential data and the motion data having sensor data timestamps that overlap the first gesture inference timestamp; using the second machine learning model, process the subset of the biopotential data and the motion data to generate the second gesture inference; and based on at least a comparison between the first gesture inference and the second gesture inference, modify the second machine learning model.

In some cases, a computer-implemented method for gesture inference may include: obtaining, from at least one camera, image(s) of an environment from a video, the at least one camera being configured to capture the video, the image(s) having image timestamps; determining a plurality of sets of key-point values based on the image(s) of the environment from the video, each set of key-point values indicating locations of portions of a hand of a user for an image of the image(s); using a first machine learning model, processing the plurality of sets of key-point values to obtain a first gesture inference, the first machine learning model being configured to output the first gesture inference of the user's hand/arm based on the plurality of sets of key-point values, the first gesture inference indicating a gesture from a plurality of defined gestures; based on the image timestamps, assigning a first gesture inference timestamp to the first gesture inference; obtaining biopotential data from a biopotential sensor of a wearable device and motion data from a motion sensor of the wearable device, the biopotential sensor being configured to obtain the biopotential data indicating electrical signals generated by nerves and muscles in the arm of the user; the motion sensor being configured to obtain the motion data relating to a motion of the portion of the arm of the user, the biopotential data and/or the motion data having sensor data timestamps; selecting a subset of the biopotential data and the motion data having sensor data timestamps that overlap the first gesture inference timestamp; using a second machine learning model, processing the subset of the biopotential data and the motion data to generate a second gesture inference, the second machine learning model being configured to output the second gesture inference of the user's hand/arm using a combination at least the biopotential data and the motion data relating to the motion of the portion of the arm of the user; and based on at least a comparison between the first gesture inference and the second gesture inference, modifying the second machine learning model.

In some cases, a system for gesture inference may include: a wearable device configured to be worn on a portion of an arm of a user, the wearable device comprising: a biopotential sensor, the biopotential sensor being configured to obtain biopotential data indicating electrical signals generated by nerves and muscles in the arm of the user; and a motion sensor, the motion sensor being configured to obtain motion data relating to a motion of the portion of the arm of the user, the motion data and biopotential data collectively being sensor data; and a processing pipeline configured to receive the biopotential data and the motion data and process the biopotential data and the motion data to generate a gesture inference output using a ML model. The processing pipeline may include: a pre-process module configured to: obtain a first set of sensor data; determine, based on the sensor data or a derivative thereof, a first transformation to the ML model and/or a second transformation to the first set of sensor data; and apply the first transformation to the ML model to obtain a session ML model and/or apply the second transformation to the first set of sensor data or derivative thereof to obtain mapped sensor data; and an inference module configured to infer the gesture inference based on (1) the session ML model and the first set of sensor data, and/or (2) the ML model and the mapped sensor data; wherein the system is configured to, based on the gesture inference, determine a machine interpretable event, and execute an action corresponding to the machine interpretable event.

In some cases, a computer-implemented method for gesture inference may include: obtaining a first set of sensor data, the first set of sensor data including motion data and biopotential data, the motion data being obtained by a motion sensor of a wearable device, the motion sensor being configured to obtain the motion data relating to a motion of a portion of an arm of a user wearing the wearable device, the biopotential data being obtained by a biopotential sensor of the wearable device, the biopotential sensor being configured to obtain the biopotential data indicating electrical signals generated by nerves and muscles in the arm of the user; determining, based on the sensor data or a derivative thereof, a first transformation to a ML model and/or a second transformation to the first set of sensor data; applying the first transformation to the ML model to obtain a session ML model and/or applying the second transformation to the first set of sensor data or derivative thereof to obtain mapped sensor data; and inferring a gesture inference based on (1) the session ML model and the first set of sensor data, and/or (2) the ML model and the mapped sensor data; wherein the wearable device is configured to, based on the gesture inference, determine a machine interpretable event, and execute an action corresponding to the machine interpretable event.

In some cases, a system for gesture inference may include: a wearable device configured to be worn on a portion of an arm of a user, the wearable device comprising: a biopotential sensor, the biopotential sensor being configured to obtain biopotential data indicating electrical signals generated by nerves and muscles in the arm of the user; and a motion sensor, the motion sensor being configured to obtain motion data relating to a motion of the portion of the arm of the user, the motion data and biopotential data collectively being sensor data; and a base ML model. The system may be configured to: prompt the user to perform a first action; obtain, using the biopotential sensor and the motion sensor, first sensor data while the user performs the first action; using at least the base ML model and the first sensor data, determine that the first action was performed by the user; select, based on at least the first sensor data, a second ML model, the second ML model being selected to provide improved inference accuracy for the user as compared to the base ML model; obtain, using the biopotential sensor and the motion sensor, second sensor data while the user performs a second action; using at least the second ML model and the second sensor data, generate an inference output indicating that the user performed the second action.

In some cases, a computer-implemented method for gesture inference may include: prompting a user to perform a first action; obtaining, using a biopotential sensor of a wearable device and a motion sensor of the wearable, first sensor data while the user performs the first action, the biopotential sensor being configured to obtain biopotential data indicating electrical signals generated by nerves and muscles in an arm of the user, the motion sensor being configured to obtain motion data relating to a motion of a portion of the arm of the user, the motion data and biopotential data collectively being sensor data; and; using at least a base ML model and the first sensor data, determining that the first action was performed by the user; selecting, based on at least the first sensor data, a second ML model, the second ML model being selected to provide improved inference accuracy for the user as compared to the base ML model; obtaining, using the biopotential sensor and the motion sensor, second sensor data while the user performs a second action; and using at least the second ML model and the second sensor data, generate an inference output indicating that the user performed the second action.

Additional objects and advantages of the disclosed technology will be set forth in part in the description that follows, and in part will be apparent from the description, or may be learned by practice of the disclosed technology.

It is to be understood that both the foregoing general description and the following detailed description are exemplary and explanatory only and are not restrictive of the disclosed technology, as claimed.

BRIEF DESCRIPTION OF THE DRAWINGS

The accompanying drawings, which are incorporated in and constitute a part of this specification, illustrate various exemplary aspects and together with the description, serve to explain the principles of the disclosed technology.

DETAILED DESCRIPTION

In general, the present disclosure is directed to methods and systems for gesture control. In some cases herein, systems of the present disclosure may train and/or infer gestures on biopotential signals using computer-vision. In some cases herein, systems of the present disclosure may train and/or infer gestures on biopotential signals and/or video using computer-vision. In this manner, computer-vision systems may provide more robust biopotential-based inference and/or multi-model inference of gestures.

In some cases herein, systems of the present disclosure may train and/or infer gestures on biopotential signals by applying transformations to the ML models and/or session data. In this manner, systems of the present disclosure may be more accurate and/or more robust, even when processing data subject to inter/intra-session variability of data.

In some cases herein, systems of the present disclosure may train and/or infer gestures on biopotential signals to select ML models to address inter/intra-session variability of data. In this manner, a ML model selected to infer a gesture may be more accurate and/or more robust given a user's circumstances.

Thus, methods and systems of the present disclosure may be improvements to computer technology and/or gesture control technology.

Environment

Figure 1:
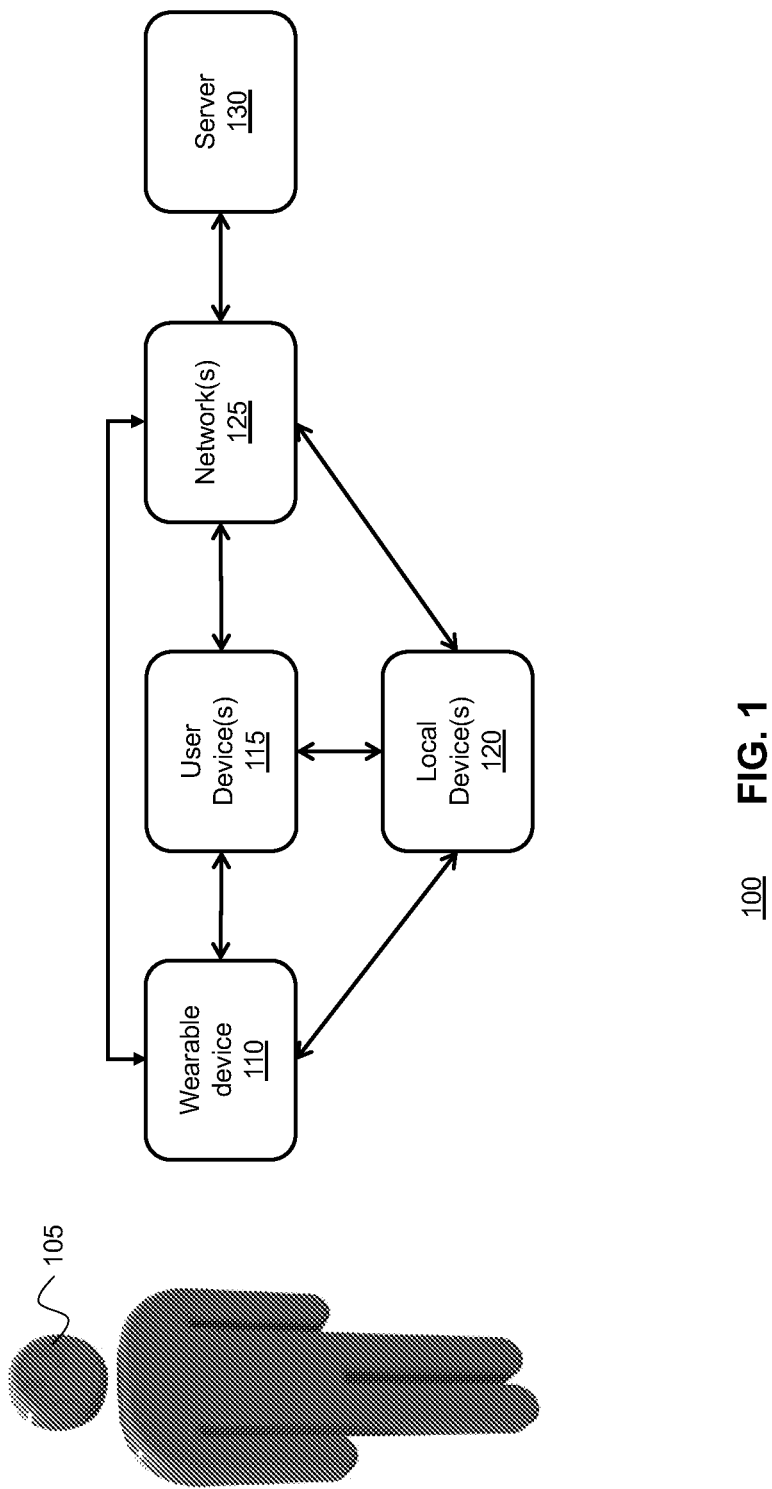
FIG. 1 depicts an example environment for gesture control using a wearable device.

FIG. 1 depicts an example environment 100 for gesture control using a wearable device 110. The environment 100 may include a user 105, the wearable device 110, a user device 115, local device(s) 120, network(s) 125, and a server 130. The wearable device 110 may obtain gesture data, so that a gesture output can be generated (e.g., by the wearable device 110, the user device 115, the server 130). The gesture output may indicate a gesture performed by the user 105. The wearable device 110, the user device 115, and/or the server 130 may then perform one or more command actions based on the gesture output, such as control remote devices (e.g., robots, UAMs, or systems), control local devices, such as the user device 115 or the local devices 120, and the like.

The user 105 may wear the wearable device 110 on a portion of an arm of the user 105, such as the wrist and/or the forearm of the user 105. The wearable device 110 may be a gesture control device, a smartwatch, or other wrist or forearm wearable (e.g., a smart sleeve). Details of electrodes and/or hardware of the wearable device 110 may be found in U.S. application Ser. No. 17/935,480, entitled "Gesture Control Using Biopotential-Based Analog Front End," filed Sep. 26, 2022, which is incorporated by reference herein.

In some cases, the user device 115 may be a personal computing device, such as a mobile phone, a tablet, a laptop, or a desktop computer. In some cases, the user device 115 may be an extended reality (XR) device, such as a virtual reality device, an augmented reality device, a mixed reality device, and the like.

The local device(s) 120 may be other information technology devices in environments, such as the home, the office, ain public, and the like. The local device(s) 120 may include speakers (e.g., smart speakers), headphones, TVs, garage doors, doors, smart locks, cars, internet of things (IoT) devices that control various electrical and mechanical devices. Thus, local device(s) 120 may generally be any software controllable device or system that can receive action commands from the wearable device 110 or the user device 115 based on gesture outputs.

The network(s) 125 may include one or more local networks, private networks, enterprise networks, public networks (such as the internet), cellular networks, satellite networks, to connect the various devices in the environment 100. In some cases, the wearable device 110 may connect to server 130 (or local device 120) via the user device 115 and/or network(s) 125, while in some cases the wearable device 110 may connect to the server 130 (or a local device 120) directly or via the network(s) 125. For instance, in some cases, the wearable device 110 may connect to the local device 120 over a short range communication standard (such as Bluetooth or WIFI) and connect to the server 130 via a longer range communication standard (such as 4G, 5G, or 6G cellular communications, or satellite communications).

The server 130 may perform certain actions, such as host ML models (e.g., different classifiers, neural networks, etc.), provide software updates to components of the environment 100, and provide personalization data for the wearable device 110. In the case of hosting ML models, the server 130 may receive requests from the wearable device 110 (e.g., via user device 115 or not) to generate a gesture output (e.g., using a certain ML model) based on gesture data; process the request to generate the gesture output; and transmit the gesture output and/or an action command based on the gesture output to the wearable device 110. In some cases, the user device 115 may host ML models and perform the same process for the wearable device 110. In some cases, the wearable device 110 may host the ML models and perform the process onboard the wearable device 110.

In the case of providing software updates to components of the environment 100, the server 130 may transmit software updates and/or ML model updates to the wearable device 110 (e.g., to change certain features thereon), transmit software features and/or ML models updates to the user device 115 (e.g., to change certain features thereon), and/or transmit software updates to the local device(s) 120 (to change certain features thereon). In some cases, the software updates may change what gesture output corresponds to what action command. In some cases, for the wearable device 110, the software updates may change how biopotential signals are processed onboard the wearable device 110, such as configurations of connection states of electrodes of a biosensor device, how encryption is handled, how communications are handled, and the like.

Figure 2A:
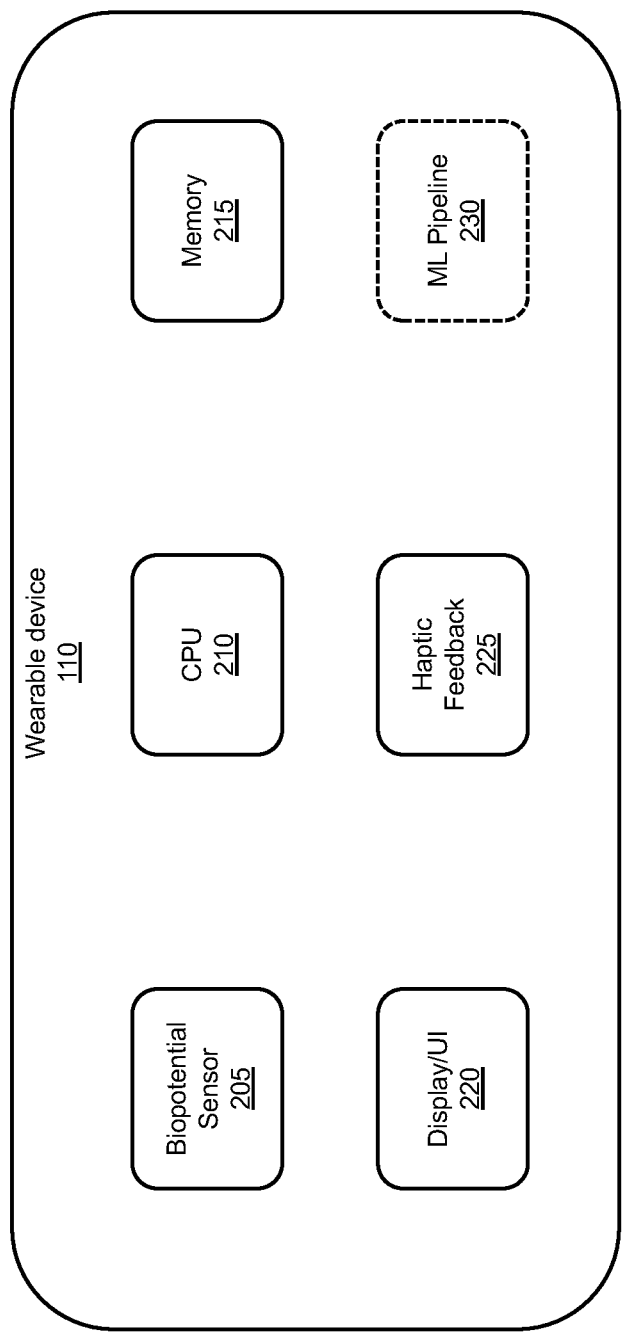
FIGS. 2A and 2B depict block diagrams of aspects of a wearable device and a user device.
Figure 2B:
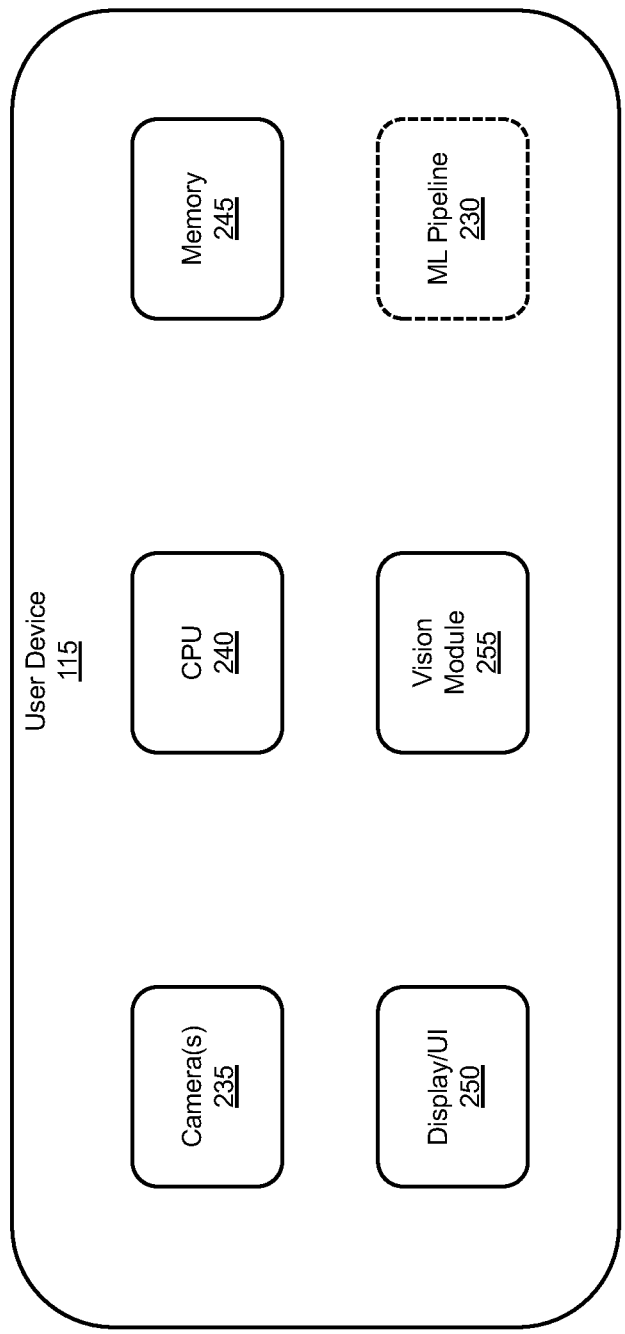

FIGS. 2A and 2B depict block diagrams 200A and 200B of aspects of a wearable device 110 and a user device 115. The aspects of the wearable device 110 and the user device 115 in block diagrams 200A and 200B may apply to the wearable device 110 and the user device 115, as discussed in FIG. 1 above.

In FIG. 2A, diagram 200A may depict a biopotential sensor 205, a CPU 210, a memory 215, a display/user interface 220 ("UI 220"), a haptic feedback module 225 (e.g., a vibration motor), and a machine learning pipeline 230 ("ML pipeline 230") in a wearable device 110.

The biopotential sensor 205 may detect gesture data. The gesture data may include biopotential signals detected by electrodes and motion data detected by a motion sensor. The biopotential signals may indicate electrical signals generated by nerves and muscles in the wrist/arm of the user. The motion data may relate to a motion of the portion of the arm of the user, such as acceleration data and/or orientation data of a portion of a user's arm. In some cases, the biopotential sensor 205 may have the ML pipeline 230 onboard and the biopotential sensor 205 may provide the gesture data to the ML pipeline 230, so that the ML pipeline 230 may generate a gesture output indicating a gesture performed by the user 105. In some cases, the biopotential sensor 205 may relay the gesture data to the ML pipeline 230 (e.g., in the CPU 210 or outside the wearable device 110, such as in the user device 115, a local device 120, and/or the server 130).

The memory 215 may store instructions (e.g., software code) for an operating system (e.g., a wearable device O/S) and at least one application, such as a biopotential sensor application. The memory 215 may also store data for the wearable device 110, such as user data, configurations of settings, and the like, but also biopotential sensor data. The biopotential sensor data may include various bits of data, such as raw biopotential data for gesture data, processed gesture data, gesture outputs, user feedback for the same, and the like.

The CPU 210 may execute the instructions to execute the O/S and the at least the biopotential sensor application. The O/S may control certain functions, such as interactions with the user 105 via the UI 220 and/or the haptic feedback module 225. The UI 220 may include a touch display, display, a microphone, a speaker, and/or software or hardware buttons, switches, dials, and the like. The haptic feedback module 225 may be an actuator to cause movement of the wearable device 110 (e.g., a vibration and the like) to indicate certain states or data. The CPU 210 may also include a communication module to send and receive communications to, e.g., the server 130, the user device 115, and/or the local device(s) 120.

The biopotential sensor application, via the CPU 210, may also interact with the user via the UI 220 and/or the haptic feedback module 225. In some cases, the biopotential sensor application, via the CPU 210, may send and receive communications to, e.g., the server 130, the user device 115, and/or the local device(s) 120. In some cases, the biopotential sensor application, via the CPU 210, may instruct the biopotential sensor 205 to change connection states, such as from gesture detection mode to ECG detection mode, and the like. In some cases, the biopotential sensor application, via the CPU 210, may interface between the biopotential sensor 205 and the O/S.

In some cases, the ML pipeline 230 may, based on the gesture data, generate the gesture output indicating the gesture performed by the user 105. As discussed herein, the ML pipeline 230 may be hosted on the wearable device 110, the user device 115, or the server 130. Generally, the ML pipeline 230 may receive the gesture data from the biopotential sensor 205 (e.g., if the ML pipeline 230 is on the wearable device 110) or via the wearable device 110 (e.g., if the ML pipeline is on the user device 115 or the server 130), and determine a gesture performed by the user 105, as discussed herein.

In FIG. 2B, diagram 200B may depict camera(s) 235, a CPU 240, a memory 245, a display/user interface 250 ("UI 250"), a vision module 255, and a machine learning pipeline 230 ("ML pipeline 230") in a user device 115.

The camera(s) 235 may be one or more digital camera(s) of a personal computing device (if the user device 115 is a personal computing device or connected to one), or one or more digital camera(s) of an XR device (if the user device 115 is an XR device or connected to one). Generally, while the camera(s) 235 are depicted as a part of the user device 115, the camera(s) 235 may be a part of any device of the environment 100, such as one or more digital camera(s) of local device(s) 120 (e.g., a television, a teleconference system, a smart speaker, a smart display, an IoT device, and the like) that is connected to other devices of the environment 100 and may process and/or transmit data (e.g., video or data based on the video) to other devices of the environment 100. As discussed herein, the camera(s) 235 may capture video (hereinafter, "video data") of a field of view 1202 (see FIG. 12) of the camera(s) 235. In some cases, the camera(s) 235 may perform some operations of the vision module 255 onboard the camera(s) 235 or pass the video data to the user device 115 (or other devices, such as the server 130 or the wearable device 110), which performs some or all operations of the vision module 255. The vision module 255 may be hosted on the camera(s) 235 (e.g., operations performed by software of the camera(s) 235), hosted on the user device 115 (e.g., operations performed by software of the user device 115), hosted on the server 130 (e.g., operations performed by software of the server 130), and/or hosted on the wearable device 110 (e.g., operations performed by software of the wearable device 110). Generally, the vision module 255 may process video data to generate image-based data, as discussed herein. In some cases, the vision module 255 may also process gesture data to synchronize the video-based data and the gesture data (see, e.g. FIG. 13), as discussed herein.

The memory 245 may store instructions (e.g., software code) for an operating system (e.g., a mobile device O/S, a tablet device O/S, a XR O/S, and the like) and at least one application, such as a biopotential control application. The memory 215 may also store data for the user device 115, such as user data, configurations of settings, and the like, but also biopotential sensor data, images, video, and the like. The biopotential sensor data may include various bits of data, such as raw biopotential data for gesture data, processed gesture data, gesture outputs, user feedback for the same, and the like.

The CPU 240 may execute the instructions to execute the O/S and at least the biopotential control application. The O/S may control certain functions, such as interactions with the user 105 via the UI 250 and/or other systems (e.g., the wearable device 110). The UI 250 may include a touch display, display, a microphone, a speaker, and/or software or hardware buttons, switches, dials, and the like. The CPU 240 may also include a communication module to send and receive communications to, e.g., the server 130, the wearable device 110, and/or the local device(s) 120.

The biopotential control application, via the CPU 240, may also interact with the user via the UI 250 and/or the wearable device 110. In some cases, the biopotential control application, via the CPU 240, may send and receive communications to, e.g., the server 130, the wearable device 110, and/or the local device(s) 120. In some cases, the biopotential control application, via the CPU 240, may instruct the biopotential sensor 205 to change connection states, such as from gesture detection mode to ECG detection mode, and the like. In some cases, the biopotential sensor application, via the CPU 240, may interface between the wearable device 110 and the O/S of the user device 115 and/or other devices (e.g., server or local devices).

In some cases, the ML pipeline 230 may, based on the gesture data and the video data, generate the gesture output indicating the gesture performed by the user 105. As discussed herein, the ML pipeline 230 may be hosted on the wearable device 110, the user device 115, or the server 130. Generally, the ML pipeline 230 may receive the gesture data from the biopotential sensor 205 (e.g., if the ML pipeline 230 is on the wearable device 110) or via the wearable device 110 (e.g., if the ML pipeline is on the user device 115 or the server 130); receive the video from the camera(s) 235;

and determine a gesture performed by the user 105, as discussed herein. In some embodiments, ML pipeline 230 may include any of the modules described below, including with respect to FIGS. 4, 5, and 8-10.

Figure 3:
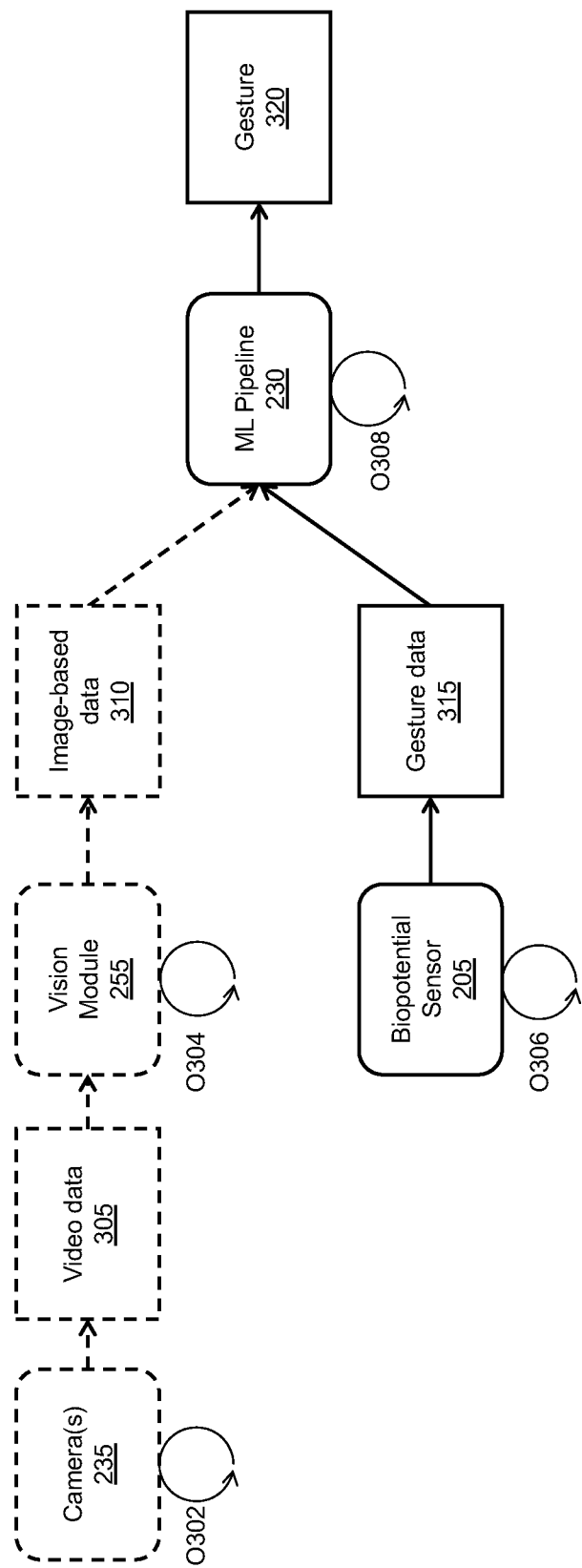
FIG. 3 depicts a block diagram depicting operations to infer a gesture based on inputs from camera(s) and/or a biopotential sensor.

FIG. 3 depicts a block diagram 300 depicting operations O302 through O308 to infer a gesture 320 based on inputs from camera(s) 235 and/or a biopotential sensor 205. Diagram 300 depicting operations O302 through O308 to infer a gesture 320 may apply to features of FIGS. 1, 2A-2B, and 4-15B herein. In particular, diagram 300 may depict interactions and operations of camera(s) 235, a vision module 255, a biopotential sensor 205, and a ML pipeline 230.

In operation O302, the camera(s) 235 may obtain video data 305. In some cases, the camera(s) 235 may be continuously on (while the user device 115 is on and operating) and obtaining video data 305 (e.g., as a part of using the user device 115). In this case, the camera(s) 235 may detect the user hand/arm with (or without) the wearable device 110. In this case, the camera(s) 235 (or another component of the environment, such as the vision module 255) may optionally process images of the video data 305 to: determine a presence of a hand/wrist/arm of the user (e.g., using image recognition software), determine a presence of a wearable device 110 on the wrist/arm (e.g., using the image recognition software), and in response to determining the presence of the hand/wrist/arm and/or the wearable device 110 on the wrist/arm, determine to start obtaining the video data 305. In some cases, the camera(s) 235 may be instructed to obtain the video data 305, e.g., by the user device 115 or the wearable device 110. For instance, the user device 115 and the wearable device 110 may connect (e.g., via Bluetooth or WIFI, and the like) and the user may start a session; the wearable device 110 or the user device 115 may determine to start obtaining the video data 305 in response to the user starting the session. In some cases, starting of a session may be indicated by a user input (e.g., on the wearable device 110 or on the user device 115), by a user putting the wearable device 110 on the user's arm/wrist, by the user performing a wake gesture with the hand/wrist/arm wearing the wearable device 110, and the like. The camera(s) 235 may transmit the video data 305 to the vision module 255.

In operation O304, the vision module 255 may receive the video data 305 from the camera(s) 235, and generate image-based data 310. In some cases, the vision module 255 may generate the image-based data 310 by processing the video data 305 to generate the image-based data 310. In some cases, the image-based data 310 may include a plurality of sets of key-point values. Each set of key-point values may indicate locations of portions of a hand of the user for an image of the image(s), as discussed herein. In some cases, the image-based data 310 may also include image timestamps for each set of key-point values. The image timestamps may correspond to a timestamp of each image of the video data 305 that was processed to determine the set of key-point values. The vision module 255 may transmit the image-based data 310 to the ML pipeline 230, such as by passing the image-based data 310 to a software module hosting the ML pipeline 230 onboard the user device 115 or by transmitting the image-based data 310 to a software module hosting the ML pipeline 230 onboard the wearable device 110 or the server 130.

In operation O306, the biopotential sensor 205 may obtain gesture data 315. In some cases, the biopotential sensor 205 may be continuously on (while the wearable device 110 is on and operating) and obtaining gesture data 315 (e.g., as a part of using the wearable device 110). In this case, the biopotential sensor 205 may detect the user is wearing the wearable device 110, and determine to start obtaining gesture data 315. In some cases, the biopotential sensor 205 may determine to start obtaining the gesture data 315 in response to a wake gesture (e.g., based on IMU data, with or without the electrodes turned on, and the like). In some cases, the biopotential sensor 205 may be instructed to obtain the gesture data 315, e.g., by the user device 115 or the wearable device 110. For instance, the user device 115 and the wearable device 110 may connect (e.g., via Bluetooth or WIFI, and the like) and the user may start a session; the wearable device 110 or the user device 115 may determine to start obtaining the gesture data 315 in response to the user starting the session. In some cases, starting of a session may be indicated by a user input (e.g., on the wearable device 110 or on the user device 115), by a user putting the wearable device 110 on the user's arm/wrist, by the user performing a wake gesture with the hand/wrist/arm wearing the wearable device 110, and the like. The biopotential sensor 205 may transmit the gesture data 315 to the ML pipeline 230, such as by passing the gesture data 310 to a software module hosting the ML pipeline 230 onboard the wearable device 110 or by transmitting the gesture data 310 to a software module hosting the ML pipeline 230 onboard the user device 115 or the server 130.

In operation O308, the ML pipeline 230 may receive the gesture data from the biopotential sensor 205 and/or of image-based data 310 from the vision module 255. The ML pipeline 230 may then determine a gesture 320 based on the gesture data 315 from the biopotential sensor 205 and/or of image-based data 310 from the vision module 255, as discussed herein. For instance, the ML pipeline 230 may infer a gesture 320, predict a gesture 320, output a three-dimensional model of the hand/wrist/arm of the user over time, using different types of classical ML models, neural network models, time-series based models, and the like.

In some cases, operations O302 and/or O304 may not be performed herein. For instance, in some cases, operations O302 and/or O304 may not be performed if camera(s) 235 are not available (e.g., the user device 115 does not have camera(s) 235) or connected to the devices of the environment 100. In some cases, operation O302 may be performed but operation O304 may not be performed if a user's arm/hand associated with the wearable device 110 is not in the field of view of the camera(s) 235.

ML Pipeline

Figure 4:
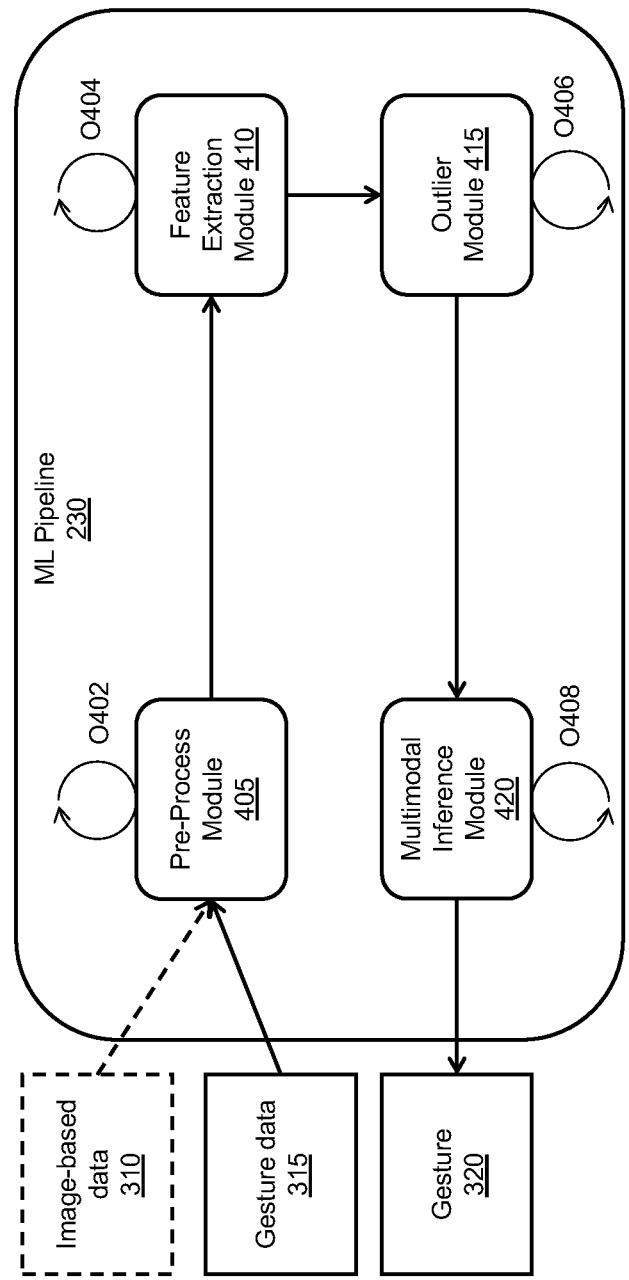
FIG. 4 depicts a block diagram depicting operations of a ML pipeline.

FIG. 4 depicts a block diagram 400 depicting operations O402 through O408 of a ML pipeline 230. Diagram 400 depicting operations O402 through O408 may apply to features of FIGS. 1-3 and 5-15B herein. In particular, the ML pipeline 230 may include a pre-process module 405, a feature extraction module 410, an outlier module 415, and a multimodal inference module 420.

In operation O402, the pre-process module 405 may receive image-based data 310 and/or gesture data 315 (collectively, "sensor data"), and perform one or more pre-process task(s), check(s), or transformations, as discussed herein. The sensor data may be obtained (directly or indirectly) from the vision module 255 and/or the biopotential sensor 205. Generally, the gesture data may be indexed by sensor data timestamps, while the image-based data (e.g., images of the video) may have image timestamps. The timestamps may be determined by the respective sensors and applied to portions of the sensor data, based on when the sensor data was collected (e.g., with respect to an independent time system, such as a GPS system or other system time indicator). The sensor data may be in data packet format (e.g., Bluetooth packets, WIFI packets, and the like). The sensor data may be streamed from the vision module 255 and/or the biopotential sensor 205. After pre-process tasks are performed, checks passed, and transformations (if any) are performed, the pre-process module 405 may transmit sensor data (or derivatives thereof) to the feature extraction module 410.

In some cases, the pre-process task(s) may include low-frequency filtering and/or electromagnetic interference filtering. The low-frequency filtering may remove low-frequency components of gesture data 315 (e.g., of the biopotential signals from the electrodes). Low-frequency signals of biopotential signals may be caused by a motion effect between electrodes of the biopotential sensor 205 and human skin of the user. The electromagnetic interference filtering may filter out, e.g., background electromagnetic interference noise caused by the electrical grids in the environment 100.

In some cases, the check(s) may include one or combinations of: a signal quality check, a data packet check, a baseline gesture check, a calibration check, and the like. Generally, the check(s) may improve accuracy (e.g., by only inferring gestures with useable sensor data) and/or control process flows of the wearable device 110 and/or the user device 115 (e.g., by routing the process to calibration/re-calibration). In some cases, the check(s) may be trigger conditions to trigger (if indicated by one of the check(s)) a prompt for the user to perform an action. The action may be a part of a calibration process, re-calibration process, or ML model selection process. For instance, a trigger condition may satisfied (1) when the wearable device 110 is initialized to a user during on initial bootup sequence, (2) when the first set of sensor data is for a new session after a period of time that the wearable device was not worn by the user, and/or (3) when the ML pipeline 230 assesses that one or more gestures were likely to have been m is-inferred or erroneously not inferred. In this case, the ML pipeline 230 may interrupt the process and request certain actions from the user, such as performing certain gestures and/or playing an interactive game, and the like.

In some cases, the signal quality check may determine whether a signal quality score is above a threshold value. The signal quality score may be based on (1) available data packets, (2) distribution of sensor data to expected values (e.g., based on historical values, such as in the outlier module 415 discussed herein), and (3) an amount of noise in the gesture data 315 of the sensor data (e.g., indicated by the low-frequency filtering and/or electromagnetic interference filtering). In this case, the ML models may be stricter and/or provide higher accuracy.

In some cases, the data packet check may determine an amount and/or sequence of sensor data, and determine whether the amount and/or sequence is sufficient to infer a gesture. In some cases, the data packet check may determine whether a sufficient number of samples of sensor data are received within a predefined period of time. For instance, if data is being routed over wireless communication (e.g., Bluetooth or WIFI, and the like) data packets may be dropped and/or not received by the ML pipeline 230. The data packet check may determine if a threshold number of sequential data packets have been received to infer a gesture. In some cases, the data packet check may determine a flag if there is a gap in data packets (e.g., a time gap of more than a set amount of time for signals). In some cases, the data packet check may determine not to infer a gesture if the gap is more than a threshold time period. In some cases, the data packet check may interpolate the sensor data (e.g., ENG or IMU data of gesture data 315, of key-point positions of the video data 305), and proceed with inference of a gesture.

In some cases, the baseline gesture check may determine if the user has performed certain baseline gestures for the session. In some cases, the baseline gesture check may not infer gestures until the user has performed the baseline gestures. If the user has not performed the baseline gestures (e.g., as a first action after performing a wake gesture) or for a given period of time (e.g., at the start of wearing the wearable device 110 or each day the wearable device 110 is worn), the baseline gesture check may interrupt the session and request the user perform the baseline gestures (or only omitted baseline gestures).

In some cases, the calibration check may determine whether the user has performed a calibration before. For instance, the calibration check may determine whether the user has performed a calibration process at a first time wearing the wearable device 110), and/or whether has performed a calibration process within a set period of time (e.g., each day, each session, and the like).

In some cases, the transformations may modify a ML model and/or the gesture data 315, as discussed herein, to address inter/intra-session variability. For instance, the transformations may include a first transformation and/or a second transformation. The first transformation may be a transformation to a ML model of the ML pipeline 230. The second transformation may be a transformation to the sensor data (e.g., a first set of sensor data that is collected for a session). The pre-process module 405 may apply the first transformation to the ML model to obtain a session ML model and/or apply the second transformation to the first set of sensor data (or derivatives thereof) to obtain mapped sensor data. The pre-process module 405 may indicate which (if any) transformations were applied, and cause the multimodal inference module 420 to use the session ML model (e.g., with the sensor data) and/or the mapped sensor data (e.g., with the ML model, not transformed) to infer a gesture.

In some cases, the pre-process module 405 may determine whether to determine/apply the first transformation or the second transformation (or neither). In some cases, the pre-process module 405 may determine whether the ML pipeline 230 has sufficient onboard processing power/memory, software, or hardware to determine the first transformation or the second transformation. For instance, the ML pipeline 230 may be hosted on the server 130 and may have access to additional resources that, e.g., the user device 115 or the wearable device 110 does not have access to perform certain processes. In response to determining the ML pipeline 230 (e.g., the CPU 210 or the like) does have the processing power/member, software, or hardware to determine the first transformation or the second transformation, the pre-process module 405 may activate the transformation functions of the ML pipeline 230. In response to determining the ML pipeline 230 (e.g., the CPU 210 or the like) does not have the processing power/member, software, or hardware to determine the first transformation or the second transformation, the pre-process module 405 may not activate the transformation functions of the ML pipeline 230.

In some cases, even if the ML pipeline 230 has the processing power/member, software, or hardware to determine the first transformation or the second transformation, the pre-process module 405 may determine a similarity score of calibration data for a user (referred to as "source data") and current session data (referred to as "target data"). The similarity score may be based on a cosine similarity score, Bhattacharyya distance, Hellinger distance, Mahalanobis distance, Earth mover's distance, kullback-leibler divergence, and the like. The ML pipeline 230 may determine whether to determine/apply the first transformation or the second transformation based on the similarity score. For instance, if a similarity score is over a threshold similarity, the pre-process module 405 may determine not to determine/apply the first transformation or the second transformation. On the other hand, if the similarity score is below the threshold similarity, the pre-process module 405 may determine to determine/apply the first transformation or the second transformation.

In some cases, the ML pipeline 230 may determine to determine/apply the first transformation if the target data has been deformed (e.g., non-covariate differences) with respect to the source data. For instance, the first transformation may enable the session ML model to still determine (e.g., lower confidence) inferences even with non-covariate differences in sensor data. In some cases, the ML pipeline 230 may determine to determine/apply the first transformation if the ML pipeline 230 determines to determine/apply the second transformation (e.g., even if the target data has not been deformed). In this case, the ML pipeline 230 may infer the gesture using both types of data/models (e.g., by selecting a higher confidence output, determining both types of data/models are in agreement, and the like).

In some cases, to determine the first transformation to the ML model, the pre-process module 405 may determine, based on the sensor data (or derivatives thereof), that the wearable device 110 is in a deviated state relative to the hand/wrist/arm of the user. In some cases, the deviated state may be known to modify the sensor data (or derivatives thereof) according to a known deviation pattern relative to the sensor data (or derivatives thereof) that would be received by the wearable device 110 if the wearable device were in a neutral state. The neutral state may be a defined posture/orientation (e.g., arm raised to in from to waist, and the like) and/or in normal wear (e.g., without sweat or damp). The pre-process module 405 may, based on the determined deviated state, determine the first transformation to the ML mode. Generally, the first transformation to the ML model may be configured to improve an inference accuracy of the ML model while the wearable device 110 is in the deviated state. In some cases, the deviated state includes a deviated arm posture that is different from the neutral arm posture when the wearable device 110 is in the neutral state. In some cases, the pre-process module 405 may determine the first transformation to the ML model by: determining, based on the motion data (or the video data 305), that the arm of the user is in the deviated arm posture (e.g., above head/shoulder, below waist, and the like). In some cases, the first transformation may be configured to apply adjustments to one or more parameters of the ML model of ML pipeline. In some cases, the model parameters may include one or more of weights, biases, thresholds, or values of the ML model. In the case the ML model includes a classical ML model (e.g., non-neural network based ML models), the first transformation may modify thresholds, conditions, policies, window sizing, and the like. In some cases, the classical ML models may include one or combinations of: linear regression model(s), linear discriminant analysis model(s), support vector machine model(s), decision tree model(s), k-nearest neighbor model(s). In some cases, the classical ML models may have regularization. For instance, ridge regularization may include a penalty equivalent to a sum of the squares of the magnitude of coefficients. In this case, the penalty may effectively shrink the coefficients of parametric models (such as linear regression model(s) or linear discriminant analysis model(s)) to avoid overfitting. For instance, lasso regularization may include a penalty equivalent to the sum of the absolute values of coefficients. In some cases, the classical ML models may include a scaling factor. For instance, in least squares support vector machine model(s), the model may include a scaling factor, $\beta$, to the parameters of the linear model. In some cases (e.g., linear discriminant analysis model(s)), the model may include shrinkage parameters. The shrinkage parameters may be applied to mean vectors and a pooled covariance matrix (PCM) of a particular user's training data, based on the mean vectors and PCM of a larger set of generalized training data (e.g., of a population of a plurality of users). In the case the ML model includes a neural network, the first transformation may modify weights, biases, activation values of one or more layers (e.g., a fully connected, end layer) of the neural network.

In some cases, the first transformation may adjust the model parameters in accordance with a difference between the source data and the target data. For instance, a magnitude (and direction) of the adjustments to the model parameters may correspond to a magnitude (and direction) of the difference.

In some cases, to determine the second transformation to the sensor data, the pre-process module 405 may determine, based on the sensor data, that the wearable device 110 is in a deviated state relative to the arm of the user, and, based on the deviated state, determine the second transformation to the sensor data. The second transformation to the sensor data may be configured to produce the mapped sensor data, so that the mapped sensor data is more similar to the sensor data that would be received by the wearable device 110 if the wearable device 110 was in the neutral state than is the sensor data. In some cases, the second transformation may include one or combinations of: a rotation, a translation, a projection, and/or a scaling. In this manner, the sensor data, as transformed to the mapped sensor data, is more similar to sensor data that would be received by the wearable device 110 if the wearable device 110 was in the neutral state.

In some cases, to determine the second transformation to the sensor data, the pre-process module 405 may determine a rotational matrix R that transforms target data $F_t$ to be similar to the source data $F_s$. In some cases, the pre-process module 405 may determine the rotational matrix R by: (1) generating a random rotational matrix $Rr$ $(\theta_1, \theta_2, \ldots, \theta_{Ck2})$, and applying the random rotational matrix $R_r$ to the target data $F_t$ to obtain a transformed target data $F_{s'}$, in accordance with Equation 1.

$$F_{s'} = F_t \times R_r(\theta_1, \theta_2, \ldots, \theta_{Ck2}) \qquad \text{Equation 1}$$

Next, the pre-process module 405 may calculate a cost in accordance with a cost function C $(F_s, F_{s'})$, in accordance with Equation 2.

$$C(F_s, F_{s'}) = \text{Dist}(F_s, F_{s'}) \qquad \text{Equation 2}$$

In some cases, Dist $(F_s, F_{s'})$ is a distance function of the source data $F_s$ and the transformed target data $F_{s'}$. For instance, the distance function may be a Bhattacharyya distance, Hellinger distance, Mahalanobis distance, Earth mover's distance, etc. Next, the pre-process module 405 may adjust the random rotational matrix $R_r$ to reduce the cost. For instance, the pre-process module 405 may optimize the random rotational matrix $R_r$ to minimize the cost. After adjusting the random rotational matrix $R_r$, the pre-process module 405 may determine the adjusted random rotational matrix $R_r$ as the rotational matrix R.

In some cases, to determine the second transformation to the sensor data, the pre-process module 405 may determine, during/after calibration, an orthogonal class centroid basis (OCCB) based on the source data, and, during inference, determine the second transformation based on the session data and the orthogonal class centroid basis. The orthogonal class centroid basis may be an orthogonal subspace spanned by class centroids of gestures of the source data. For instance, the orthogonal class centroid basis may be determined by Gram-Schmidt Orthogonalization on centroids of clusters of features in a first feature space (of the features). The orthogonal subspace of the orthogonal class centroid basis may be a subspace of the first feature space. During inference, the pre-process module 405 may determine the second transformation by determining a dot product of the target data (or subsets of the target data, such as sensor data features of session data, in the first feature space) and the orthogonal class centroid basis. In some cases, the target data may be modified by the class centroids of the target data, for instance by subtracting the class centroids from the target, before determining the dot product with the orthogonal class centroid basis.

In some cases, during calibration, the ML pipeline 230 may determine conventional and OCCB features (e.g., the orthogonal class centroid basis) of the source data, and train or modify the ML model of the ML pipeline 230 using the conventional and OCCB features. During inference, the ML pipeline 230 may determine the conventional and OCCB features of the target data (e.g., transformed session data by the second transformation on the session data), and perform inference using the conventional and/or OCCB features.

In operation O404, the feature extraction module 410 may receive the sensor data (or derivatives thereof) from the pre-process module 405, and determine sensor data features. The sensor data (and/or derivative thereof) and/or the sensor data features may be considered session data. Session data may be for a certain period of time or certain set of data packets. For instance, in the case the outlier module 415 or the multimodal inference module 420 only use sensor data features, the session data may omit sensor data (or derivatives thereof) and only include sensor data features; in other cases where the outlier module 415 or the multimodal inference module 420 use sensor data features and the sensor data (and/or derivatives thereof), the session data may include all (or subsets) of the sensor data (and/or derivatives thereof) and the sensor data features. In some cases, the session data (in additional to or without the sensor data) may include the mapped sensor data.

In some cases, the sensor data features may include image features, IMU features, and/or ENG features. In some cases, the sensor data features may include one or combinations of: time domain ENG features of the biopotential data; frequency domain ENG features of the biopotential data; temporal-spatial descriptor-based features; IMU features of the IMU data; discrete wavelet transform features of the biopotential data and/or IMU data; continuous wavelet transform features of the biopotential data and/or IMU data; short-time Fourier transform features of the biopotential data and/or IMU data; derivatives of the sensor data; and/or learned latent features determined by a ML model. In some cases, the sensor data features may include certain types of complexity features, such as sample entropy, maximum fractal length.

In operation O406, the outlier module 415 may receive the session data from the feature extraction module 410, and determine whether the session data is an outlier or not. Generally, the outlier module 415 may, if the outlier module 415 determines the session data is an outlier, raise flags (e.g., for other components of the environment) or interrupt inference and/or calibration to instruct the user to perform certain actions.

In some cases, the outlier module 415 may compare the session data to at least one statistical file. A statistical file may include a set of values. In some cases, the set of values may indicate a multi-variable distribution based on historical sensor data for known gestures. The multi-variable distribution may be one or combinations of types of sensor data features types or defined indicators. The historical sensor data may be obtained from test subjects (e.g., performing the known gestures) or obtained from calibration sessions. In some cases, the outlier module 415 may use a first statistical file during calibration and a second statistical file during inference. The first statistical file may be based on data gathered from a population of users (e.g., test subjects). The second statistical file may be based on calibration data gathered from the user during a calibration session. The outlier module 415 may reduce a false positive rate of the ML pipeline 230. For instance, without the outlier module 415, the ML pipeline 230 may infer a gesture based on any incoming data payload as one of the pre-trained gesture classes even if the data payload is actually poor quality data.

In some cases, the outlier module 415 may determine whether the session data (e.g., the sensor data features or defined indicators) is an outlier as compared to a statistical file based on a result from a Hotelling's T-Squared statistical test. For instance, the defined indicators may include one or combinations of: class means (e.g., class centroids) of training data/calibration data in a feature space for each gesture class; covariance matrices of the training data/calibration data in the training data/calibration session in the feature space for each gesture class; means of ratios of the electromagnetic inference component to a total of all other frequency components in the training data/calibration data for each gesture class; a standard deviation of ratios of the electromagnetic inference component to the total of all other frequency components in the training data/calibration data for each gesture class; a number of features extracted from the training data/calibration data; and/or a number of data points used for each gesture class.

In some cases, the first statistical file a global statistical file. The global statistical file may be based on multiple second statistical files of prior users. For instance, the global statistical file may be averages or distributions of the multi-variable distribution of the second statistical files of prior users. Each second statistical file may be determined from a calibration session of a specific user, as discussed below. The global statistical file may be used for calibration validation. The calibration validation may identify potential data quality issues in the calibration workflow to avoid a garbage-in-garbage-out scenario. The calibration validation may work similarly to the outlier detection in the inference time. When a specific gesture of calibration data is collected, the ML pipeline 230 may compare the calibration data to the multi-variable distribution of the global file to determine whether the collected data is similar to expected calibration data (e.g., within a range, such as one standard deviation of prior users). If not, the ML pipeline 230 may prompt the user to guide him/her to improve the gesture formation so that a high-quality calibration model can be generated.

In some cases, the second statistical file may be user-specific and based on a calibration session of a user. During an inference session, the session data may be processed and compared to the multi-variable distribution of the second statistical file. For instance, the multi-variable distribution of the second statistical file may include, but not limited to, class centroids and covariance matrices to compute Hoteling's T-squared statistics. The Hoteling's T-squared statistics may be statistical measures of how far the features of the session data are away from the class centroids in the feature space statistically from the multi-variable distribution of the second statistical file. In some cases, if the Hoteling's T-squared statistics are larger than a preset confidence level for all variables of the multi-variable distribution of the second statistical file (e.g., the class centroids), the session data is determined to be an outlier and the session data may not be used by the multimodal inference module 420 in inference. In some cases, the ML pipeline 230 may be interrupted until a next data packet of sensor data is received.

In operation O408, the multimodal inference module 420 may receive the session data from the feature extraction module 410 (or directly via the outlier module 415, if sensor data features are not used by the multimodal inference module 420), and determine a gesture 320. Generally, the multimodal inference module 420 may infer the gesture inference based on (1) the session ML model and the session data, and/or (2) the ML model and the mapped sensor data. In some cases, neither transformation is applied, and the multimodal inference module 420 may infer the gesture using the ML model and the session data.

In some cases, the ML model of the multimodal inference module 420 may include a first ML model to infer an IMU gesture inference based on the motion data, and a second ML model to infer a biopotential gesture inference based on the biopotential data and the motion data. In this case, the multimodal inference module 420 determines the gesture inference based on the IMU gesture inference and the biopotential gesture inference. In some cases, the first ML model and the second ML model may be modified by the first transformation. In some cases, only the second ML model may be modified by the first transformation. In some cases, only the first ML model may be modified by the first transformation.

In some cases, the multimodal inference module 420 may store successive biopotential gesture inferences; determine a threshold number of the successive biopotential gesture inferences have been stored; and determine the gesture inference based on the threshold number of the successive biopotential gesture inferences. For instance, the multimodal inference module 420 may determine the gesture inference based on probability information of a confusion matrix. The confusion matrix may be generated during training of the second ML model.

After a gesture is inferred, the ML pipeline 230 may pass the inferred gesture to an application, such as the biopotential control application and/or the biopotential sensor application. The application, based on the gesture inference, may determine a machine interpretable event, and execute an action corresponding to the machine interpretable event. The application may have a defined list of machine interpretable event (e.g., types of gestures) that correspond to actions (e.g., depending on context, such as connected devices or which device is being controlled).

Figure 5:
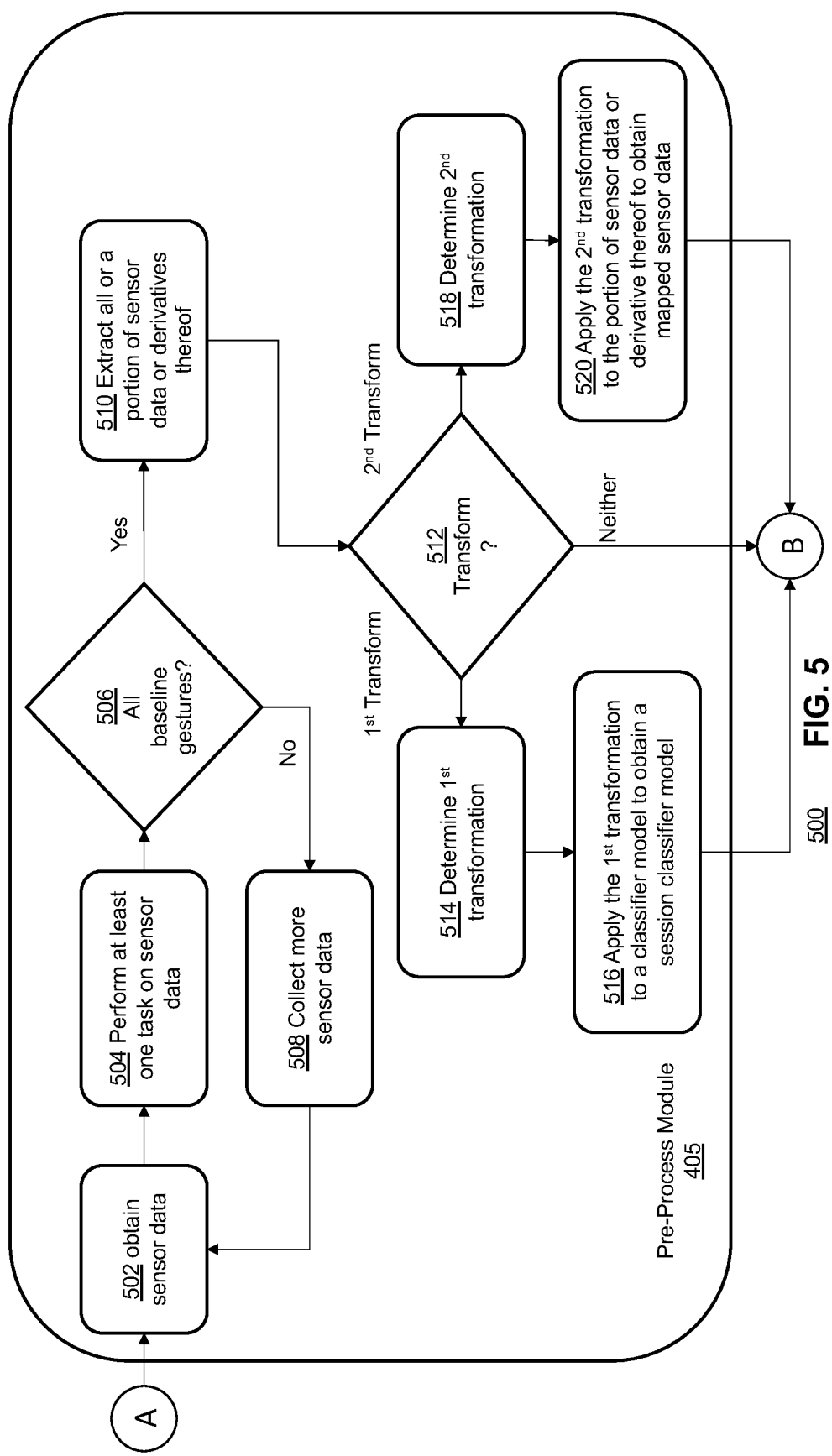
FIG. 5 depicts a flowchart of a pre-process module.

FIG. 5 depicts a flowchart 500 of a pre-process module 405. The flowchart 500 may apply to features of FIGS. 1-4 and 6-15B herein. In some cases, the flowchart 500 may start at point A and end at point B.

In block 502, the pre-process module 405 may obtain sensor data. In some cases, the pre-process module 405 may obtain the sensor data by receiving data packets from wearable device 110 and/or the user device 115, as discussed herein.

In block 504, the pre-process module 405 may perform at least one task on the sensor data. In some cases, the pre-process module 405 may perform the pre-process task(s) and, in some cases, the check(s), as discussed herein.

In block 506, the pre-process module 405 may determine whether all baseline gestures have been obtained. In some cases, the pre-process module 405 may determine all baseline gestures have been obtained if the biopotential sensor 205 has been calibrated for this session, calibrated within a certain threshold of time, and the like, as discussed herein.

In block 508, in response to determining all the baseline gestures have not been obtained (block 506: No), the pre-process module 405 may collect more sensor data. In some cases, the pre-process module 405 may determine certain baseline gestures have not been collected, or the wearable device 110 needs to be (re)calibrated, and the like, as discussed herein. After collecting more sensor data (block 502), the pre-process module 405 may start the sequence again.

In block 510, in response to determining all the baseline gestures have been obtained (block 506: Yes), the pre-process module 405 may extract all or a portion of sensor data or derivatives thereof. In some cases, the pre-process module 405 may select data from sequential data packets (e.g., indicating continuous sensor data) or sequential data packets with sufficiently small gaps for interpolation, as discussed herein.

In block 512, the pre-process module 405 may determine if (any) transformations are to be generated. In some cases, the pre-process module 405 may determine that a first transformation and/or a second transformation, or neither are to be determined, as discussed herein.

In block 514, in response to determining that a first transformation is to be determined (block 512: first transform), the pre-process module 405 may determine the first transformation. In some cases, the pre-process module 405 may determine the first transformation based on a deviated state, as discussed herein. In block 516, the pre-process module 405 may apply the first transformation to a ML model to obtain a session ML model. In some cases, the pre-process module 405 may modify the model parameters, as discussed herein. The pre-process module 405 may then proceed to point B (in parallel to or without the second transformation).

In block 518, in response to determining that a second transformation is to be determined (block 512: second transform), the pre-process module 405 may determine the second transformation. In some cases, the pre-process module 405 may determine the second transformation based on the deviated state, as discussed herein. In block 520, the pre-process module 405 may apply the second transformation to the portion of sensor data or derivative thereof to obtain mapped sensor data. In some cases, the pre-process module 405 may translate, rotate, scale, or project the sensor data, as discussed herein. The pre-process module 405 may then proceed to point B (in parallel to or without the first transformation).

In some cases, the pre-process module 405 may determine that neither a first transformation nor a second transformation are to be determined (block 512: neither). In this case, the pre-process module 405 may proceed directly to point B.

Figure 6:
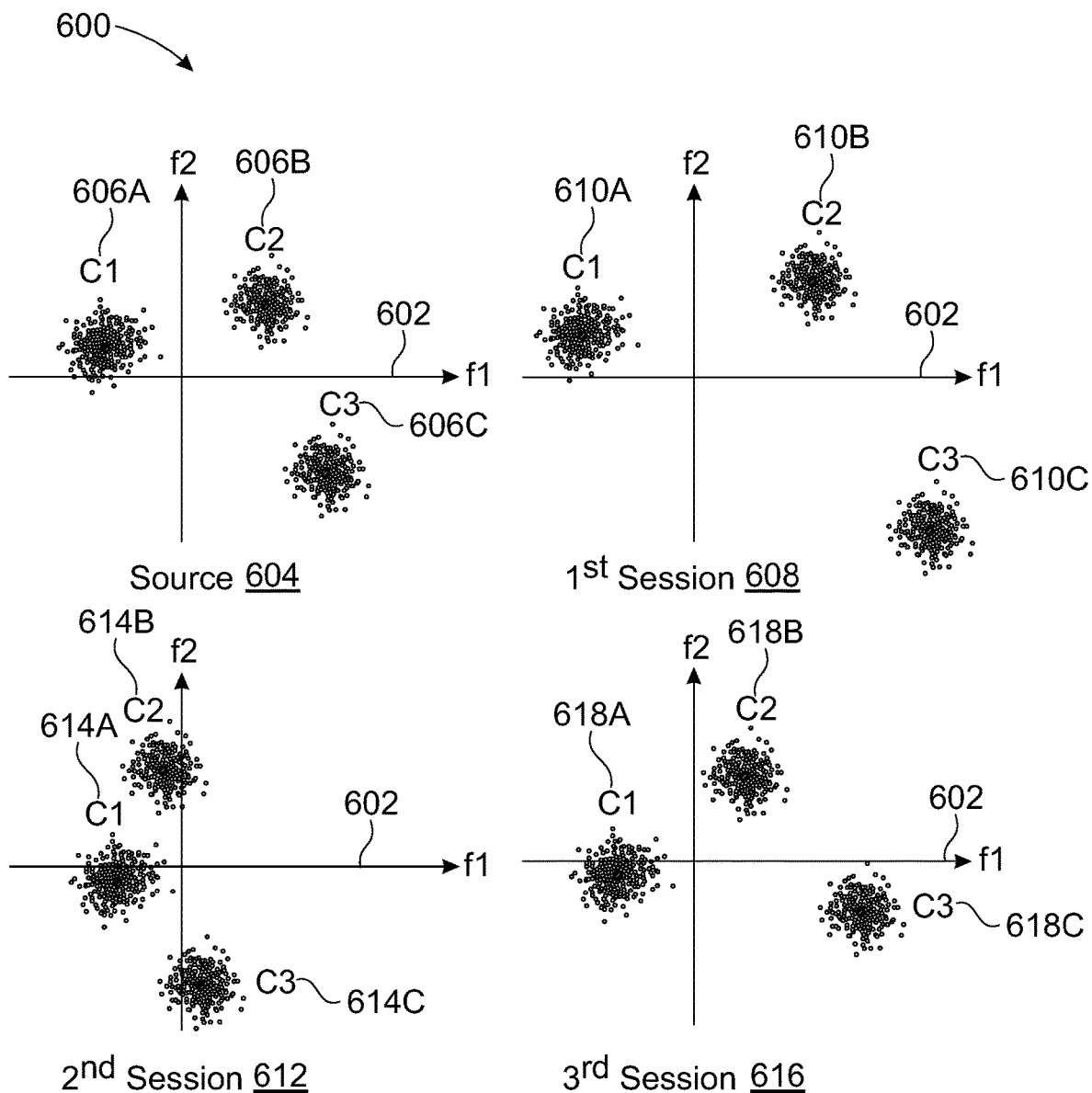
FIG. 6 depicts a diagram depicting inter-session variability.

FIG. 6 depicts a diagram 600 depicting inter-session variability. Diagram 600 may apply to features of FIGS. 1-5 and 7-15B herein. In particular, the diagram 600 includes different distributions of clusters in a feature space, as compared from a source data set 604 to a first session data set 608, second session data set 606, and a third session data set 608.

In some cases, the source data set 604 may depict source session data from one or a plurality of calibration sessions. A calibration session may be a known default (e.g., normal) operating environment/situation and for known user gestures. In some cases, the calibration session may instruct the user on how to place the wearable device 110 and when to perform the known user gestures. In some cases, the wearable device 110 may instruct the user on how to perform the known user gestures or the user may perform known user gestures in response to timed stimuli (e.g., an interactive game, and the like). The source session data may be depicted as clusters within a feature space 602. While the feature space 602 is depicted with two dimensions (corresponding to certain aspects of components of the session data), the feature space 602 may include N dimensions (N being a number corresponding to aspects of the components of the session data). The source session data may include a first cluster 606A, a second cluster 606B, and a third cluster 606C. While three clusters are depicted, there may be a smaller or a larger number of clusters, based on which components of the session data are clustered and how the data is related.

In some cases, the system (e.g., the wearable device 110/server 130) may collect session data from different types of sessions. Each type of session may be a known operating environment/situation and, optionally, for known user gestures. In some cases, the known operating environment/situation may be a certain user state (e.g., post workout/sweaty/damp situation, etc.), a certain arm position (e.g., overhead or by waist, etc.), and/or a certain placement of the wearable device 110 on the user (e.g., off center of wrist by a certain range of distance), and the like. The wearable device 110 may instruct the user on how to place the wearable device 110 and/or when to perform the known user gestures. In some cases, the wearable device 110 may instruct the user on how to perform the known user gestures or the user may perform known user gestures in response to timed stimuli (e.g., an interactive game, and the like).

In some cases, the first session data set 608 may depict first session data from one or a plurality of first sessions (e.g., post workout/sweaty/damp situation, in which the biopotential electrodes may experience an impedance change). The first session data may be depicted as clusters within the feature space 602. The first session data may include a first cluster 610A, a second cluster 6106, and a third cluster 610C, corresponding to the first cluster 606A, the second cluster 606B, and the third cluster 606C. As depicted, the first cluster 610A, the second cluster 6106, and the third cluster 610C may be scaled relative to the first cluster 606A, the second cluster 606B, and the third cluster 606C.

In some cases, the second session data set 612 may depict second session data from one or a plurality of second sessions (e.g., significant electrode shift). The second session data may be depicted as clusters within the feature space 602. The second session data may include a first cluster 614A, a second cluster 614B, and a third cluster 614C, corresponding to the first cluster 606A, the second cluster 606B, and the third cluster 606C. As depicted, the first cluster 614A, the second cluster 614B, and the third cluster 614C may be non-covariately changed (e.g., deformed) relative to the first cluster 606A, the second cluster 606B, and the third cluster 606C.

In some cases, the third session data set 616 may depict third session data from one or a plurality of third sessions (e.g., minor electrode shift). The third session data may be depicted as clusters within the feature space 602. The third session data may include a first cluster 618A, a second cluster 618B, and a third cluster 618C, corresponding to the first cluster 606A, the second cluster 606B, and the third cluster 606C. As depicted, the first cluster 618A, the second cluster 618B, and the third cluster 618C may be covariately changed (e.g., rotated) relative to the first cluster 606A, the second cluster 606B, and the third cluster 606C.

In other cases, the clusters may be one or combinations of: translated, rotated, scaled, deformed, projected, and the like, in different types of sessions. These types of different signal readings (e.g., for biopotential signals) may cause degradation of performance of ML models across sessions.

Figure 7:
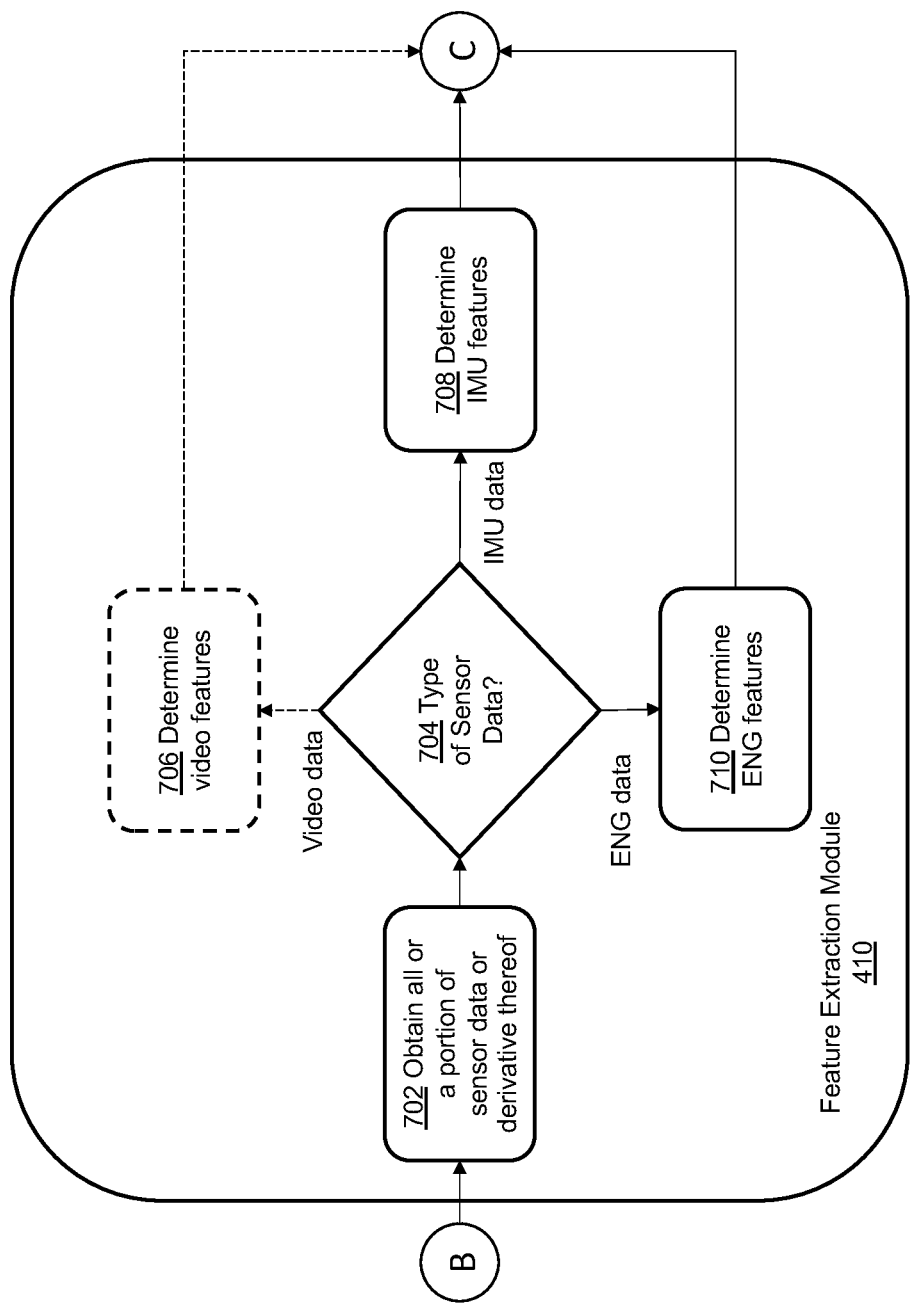
FIG. 7 depicts a flowchart of a feature extraction module.

FIG. 7 depicts a flowchart 700 of a feature extraction module 410. The flowchart 700 may apply to features of FIGS. 1-6 and 8-15B herein. In some cases, the flowchart 700 may start at point B from FIG. 5 and end at point C.

In block 702, the feature extraction module 410 may obtain all or a portion of sensor data or derivative thereof. In some cases, the feature extraction module 410 may obtain the selected subset of sensor data from the pre-process module 405, as discussed herein.

In block 704, the feature extraction module 410 may determine types of sensor data. In some cases, the feature extraction module 410 may determine whether video data, IMU data, and/or ENG data are included in the sensor data, as discussed herein.

In block 706, in response to determining the types of sensor data includes video data (block 704: video data), the feature extraction module 410 may determine video features. In some cases, the feature extraction module 410 may determine video features, such as sets of key-point values, as discussed herein. The feature extraction module 410 may then proceed to point C (in parallel to or without other features, based on types of sensor data).

In block 708, in response to determining the types of sensor data includes IMU data (block 704: IMU data), the feature extraction module 410 may determine IMU features. In some cases, the feature extraction module 410 may determine temporal-spatial descriptor-based features; IMU features of the IMU data (e.g., position, velocity, acceleration, orientation, etc.); discrete wavelet transform features of IMU data; continuous wavelet transform features of IMU data; short-time Fourier transform features of IMU data; derivatives of the sensor data; and/or learned latent features determined by a ML model, as discussed herein. The feature extraction module 410 may then proceed to point C (in parallel to or without other features, based on types of sensor data).

In block 710, in response to determining the types of sensor data includes determine ENG features (block 704: ENG data), the feature extraction module 410 may determine ENG features. In some cases, the feature extraction module 410 may determine time domain ENG features of the biopotential data; frequency domain ENG features of the biopotential data; temporal-spatial descriptor-based features; discrete wavelet transform features of the biopotential data; continuous wavelet transform features of the biopotential data; short-time Fourier transform features of the biopotential data; derivatives of the sensor data; and/or learned latent features determined by a ML model, as discussed herein. The feature extraction module 410 may then proceed to point C (in parallel to or without other features, based on types of sensor data).

Figure 8:
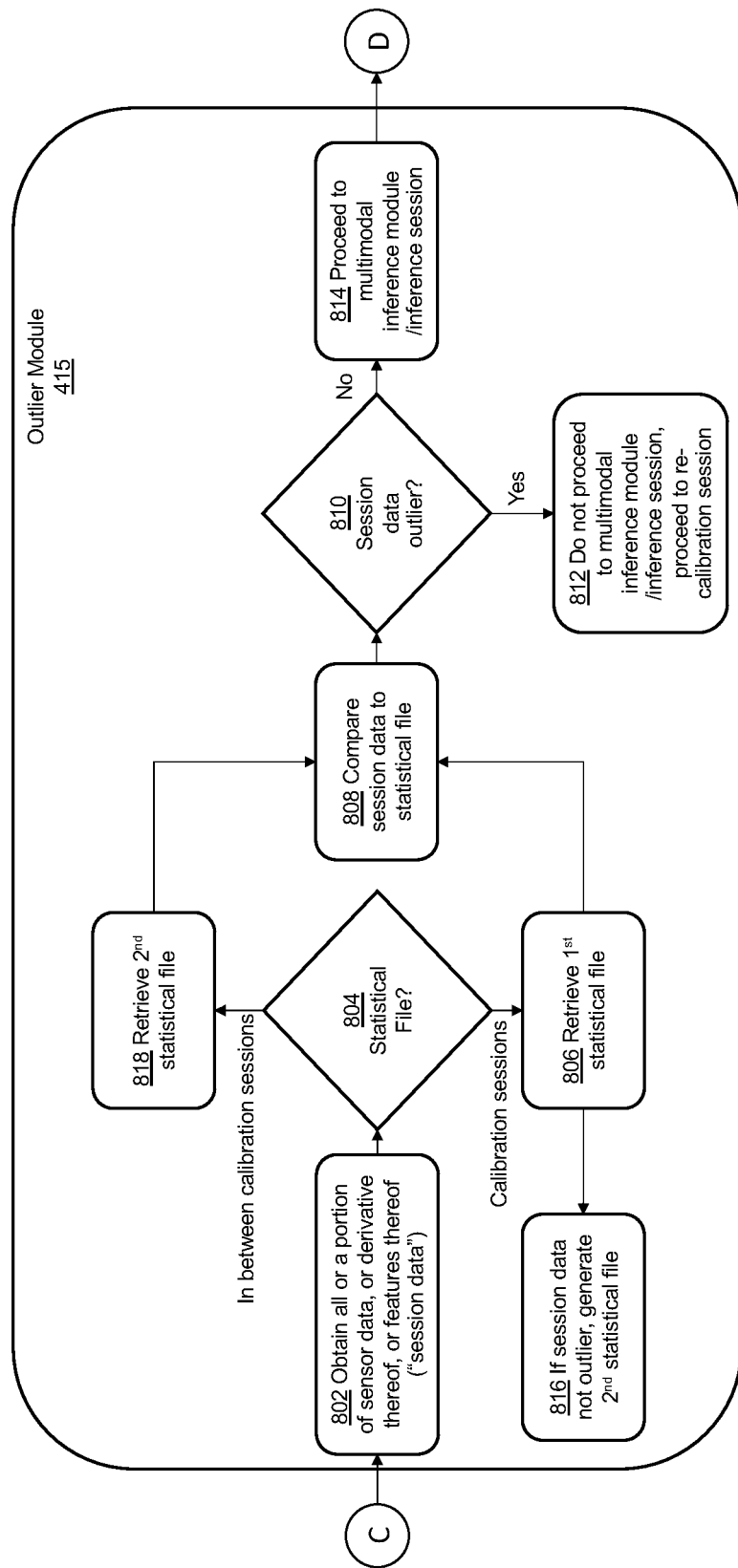
FIG. 8 depicts a flowchart of an outlier module.

FIG. 8 depicts a flowchart 800 of an outlier module 415. The flowchart 800 may apply to features of FIGS. 1-7 and 9-15B herein. In some cases, the flowchart 800 may start at point C from FIG. 7 and end at point D.

In block 802, the outlier module 415 may obtain all or a portion of the sensor data (and/or derivative thereof), and/or sensor data features ("session data"). In some cases, the outlier module 415 may obtain the session data, or subsets thereof, from the pre-process module 405 and/or the feature extraction module 410, as discussed herein.

In block 804, the outlier module 415 may determine a statistical file to use. In some cases, the outlier module 415 may determine whether the wearable device 110 and/or user has not been calibrated before or within a certain period of time, and the like, as discussed herein. If so, the outlier module 415 may determine to use a first statistical file; if not, the outlier module 415 may determine to use a second statistical file.

In block 806, in response to determining to use the first statistical file (block: 804: calibration session), the outlier module 415 may retrieve the first statistical file. In some cases, the outlier module 415 may retrieve the first statistical file from a memory associated with the ML pipeline 230 (e.g., on a same device or in the cloud, etc.), as discussed herein.

In block 808, the outlier module 415 may compare the session data to a statistical file. In some cases, the outlier module 415 may compare the session data to a first or second statistical file based on which one the outlier module 415 determined to use, as discussed herein. Thus, in some cases, the outlier module 415 may compare the session data to the first statistical file (e.g., during a calibration session) or compare the session data to a second statistical file (e.g., during a non-calibration session/inference session, in between calibration sessions).

In block 810, the outlier module 415 may determine whether the session data is an outlier. In some cases, the outlier module 415 may determine whether the session data is an outlier based on the comparison of the session data to the statistical file, as discussed herein.

In block 812, in response to determining the session data is an outlier (block 810: Yes), the outlier module 415 may not proceed to the multimodal inference module 420 to infer a gesture, not proceed to an inference session (e.g., to capture new session data and infer a gesture), and/or proceed to a re-calibration session (e.g., to capture calibration session data and re-calibrate the wearable device 110).

In block 814, in response to determining the session data is not an outlier (block 810: No), the outlier module 415 may proceed to the multimodal inference module 420 to infer a gesture and/or proceed to an inference session (e.g., to capture new session data and infer a gesture). The outlier module 415 may then proceed to point D.

In block 816, the outlier module 415 may, if session data (e.g., for a calibration session) is determined not to be an outlier, generate a second statistical file. In some cases, the outlier module 415 may determine one or combinations of: class means (e.g., class centroids) of calibration data in a feature space for each gesture class; covariance matrices of the calibration data in the calibration session in the feature space for each gesture class; means of ratios of the electromagnetic inference component to a total of all other frequency components in the calibration data for each gesture class; a standard deviation of ratios of the electromagnetic inference component to the total of all other frequency components in the calibration data for each gesture class; a number of features extracted from the calibration data; and/or a number of data points used for each gesture class.

In block 818, in response to determining to use the second statistical file (block: 804: in between calibration sessions), the outlier module 415 may retrieve a second statistical file. The outlier module 415 may then compare the session data to the second statistical file (block 808) and determine whether the session data is an outlier or not (block 810). In response to determining the session data is not an outlier, the outlier module 415 may proceed to point D and perform inference; in response to determining the session data is an outlier, the outlier module 415 may not proceed to point D and may not perform inference of a gesture.

Figure 9:
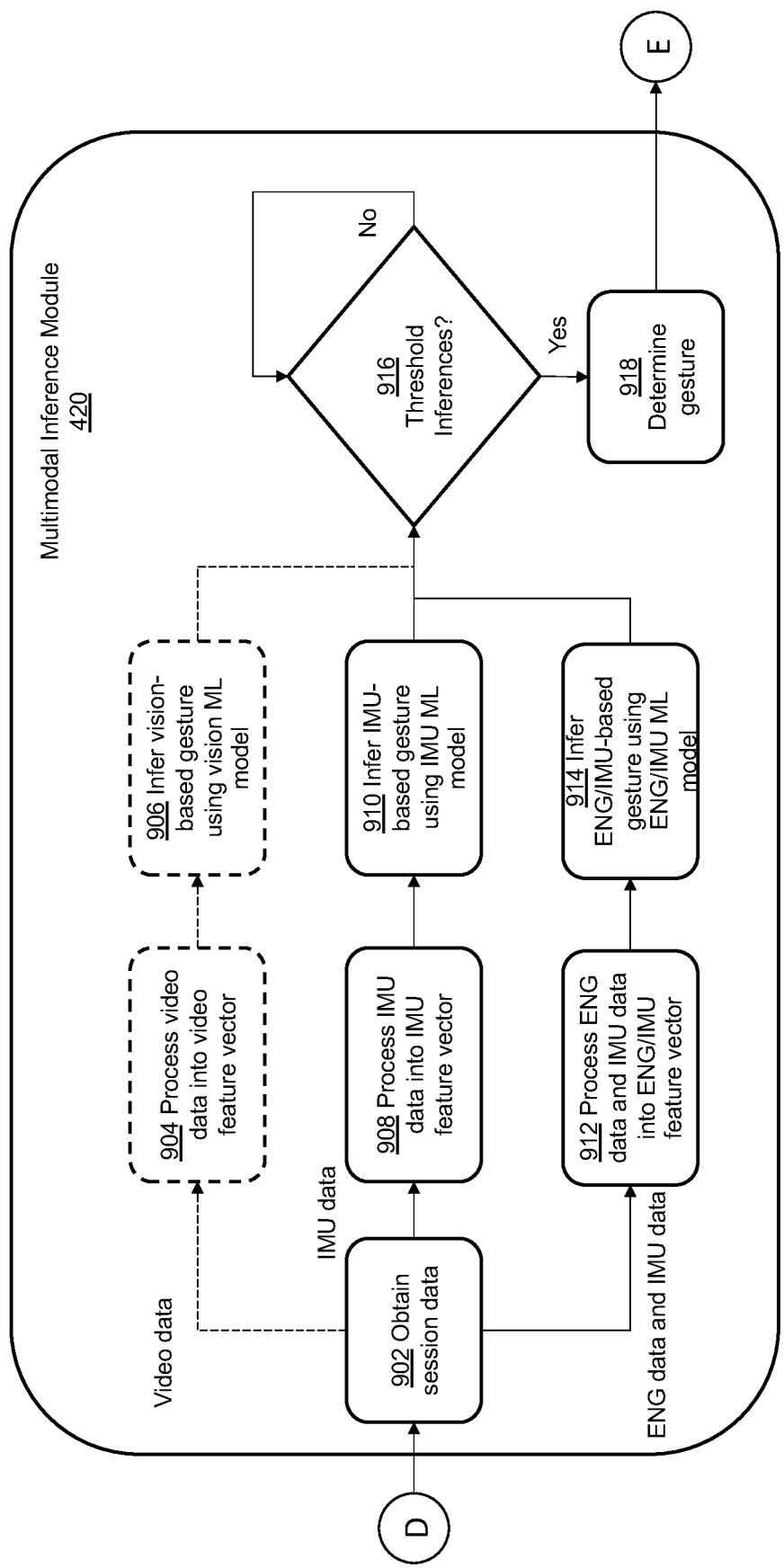
FIG. 9 depicts a flowchart of a multimodal inference module.

FIG. 9 depicts a flowchart 900 of a multimodal inference module 420. The flowchart 900 may apply to features of FIGS. 1-8 and 10-15B herein. In some cases, the flowchart 900 may start at point D from FIG. 8 and end at point E.

In block 902, the multimodal inference module 420 may obtain the session data. In some cases, the multimodal inference module 420 may obtain the session data from the outlier module 415 and/or from the feature extraction module 410, as discussed herein.

In block 904, in the case the session data includes video data, the multimodal inference module 420 may process video data into a video feature vector. In some cases, the multimodal inference module 420 may generate the video feature vector to include images of the video data and/or sets of key-point values for the images of the video data. For instance, in the case that the video feature vector includes images, the images may be processed as a matrix of pixel values and/or concatenated vectors of rows/columns of pixel values from the images. In the case the video feature vector includes sets of key-point values, the sets may be processed as a matrix of values (e.g., each column corresponding to an image timestamp, each row corresponding to a key-point of the user hand), and/or concatenated vectors of a set of key-point values.

In block 906, the multimodal inference module 420 may infer a vision-based gesture using a vision ML model. In some cases, the multimodal inference module 420 may infer a vision-based gesture inference by processing the video feature vector through the vision ML model, and receiving an output of the vision-based gesture inference, as discussed herein.

In block 908, in the case the session data includes IMU data, the multimodal inference module 420 may process the IMU data into an IMU feature vector. In some cases, the multimodal inference module 420 may generate the IMU feature vector by generate a matrix of timestamped IMU data, and/or a concatenated vectors of rows/columns of the matrix from the timestamped IMU data. For instance, the timestamped IMU data may include a plurality of IMU channels (e.g., X position, Y position, Z position, alpha angle, beta angle, and zeta angle (with respect to, e.g., magnetic north or vertical against gravity), and columns (or rows) may include IMU channels, while the rows (or columns) may correspond different timestamps.

In block 910, the multimodal inference module 420 may infer an IMU-based gesture using a IMU ML model. In some cases, the multimodal inference module 420 may infer the IMU-based gesture inference by processing the IMU feature vector through the IMU ML model, as discussed herein.

In block 912, in the case the session data includes ENG data and IMU data, the multimodal inference module 420 may process the ENG data and the IMU data into an ENG/IMU feature vector. In some cases, the multimodal inference module 420 may generate a matrix of timestamped ENG/IMU data, and/or a concatenated vectors of rows/columns of the matrix. For instance, the timestamped ENG/IMU data may include a plurality of ENG channels and the plurality of IMU channels. The ENG channels may include biopotential signal of electrodes, differential of combinations of pairs of electrodes (e.g., fixed or dynamic), a reference signal of a reference electrode(s), impendence measurements (of channels or as a system), and the like, and columns (or rows) may include ENG channels, while the rows (or columns) may correspond different timestamps.

In block 914, the multimodal inference module 420 may infer an ENG/IMU-based gesture using an ENG/IMU ML model. In some cases, the multimodal inference module 420 may infer the ENG/IMU-based gesture inference by processing the ENG/IMU feature vector through the ENG/IMU ML model, as discussed herein.

In block 916, the multimodal inference module 420 may determine whether a threshold number of inferences have been determined. In some cases, the multimodal inference module 420 may determine whether a threshold number of inferences have been determined for a type of inference. In some cases, the threshold number of inferences may an aggregate of vision-based gesture inferences, IMU-based gesture inferences, and/or ENG/IMU-based gesture inferences. In some cases, the threshold number of inference may be a summation of ENG/IMU-based gesture inferences, while the IMU-based gesture inference and/or the vision-based gesture inferences may be confirmatory (e.g., indeterminate or in agreement with the ENG/IMU-based gesture inferences). In response to determining that a threshold number of inferences have not been determined (block 916: No), the multimodal inference module 420 may return to wait for more inferences until the threshold number of inferences have been determined. For instance, the multimodal inference module 420 may store the inferences for a set period of time, for a set number of data packets, and the like. For instance, the inferences may be stored in a first-in, first out data structure (based on inference/sensor time, and count), such that a set of inferences may be associated with a same user gesture.

In block 918, in response to determining that a threshold number of inferences have been determined (block 916: Yes), the multimodal inference module 420 may determine a gesture based on the determined inferences. In some cases, the multimodal inference module 420 may determine whether ENG/IMU-based gesture inferences, the IMU-based gesture inference, and/or the vision-based gesture inferences are in agreement, select an inference with highest confidence, and the like.

ML Models

Figure 10:
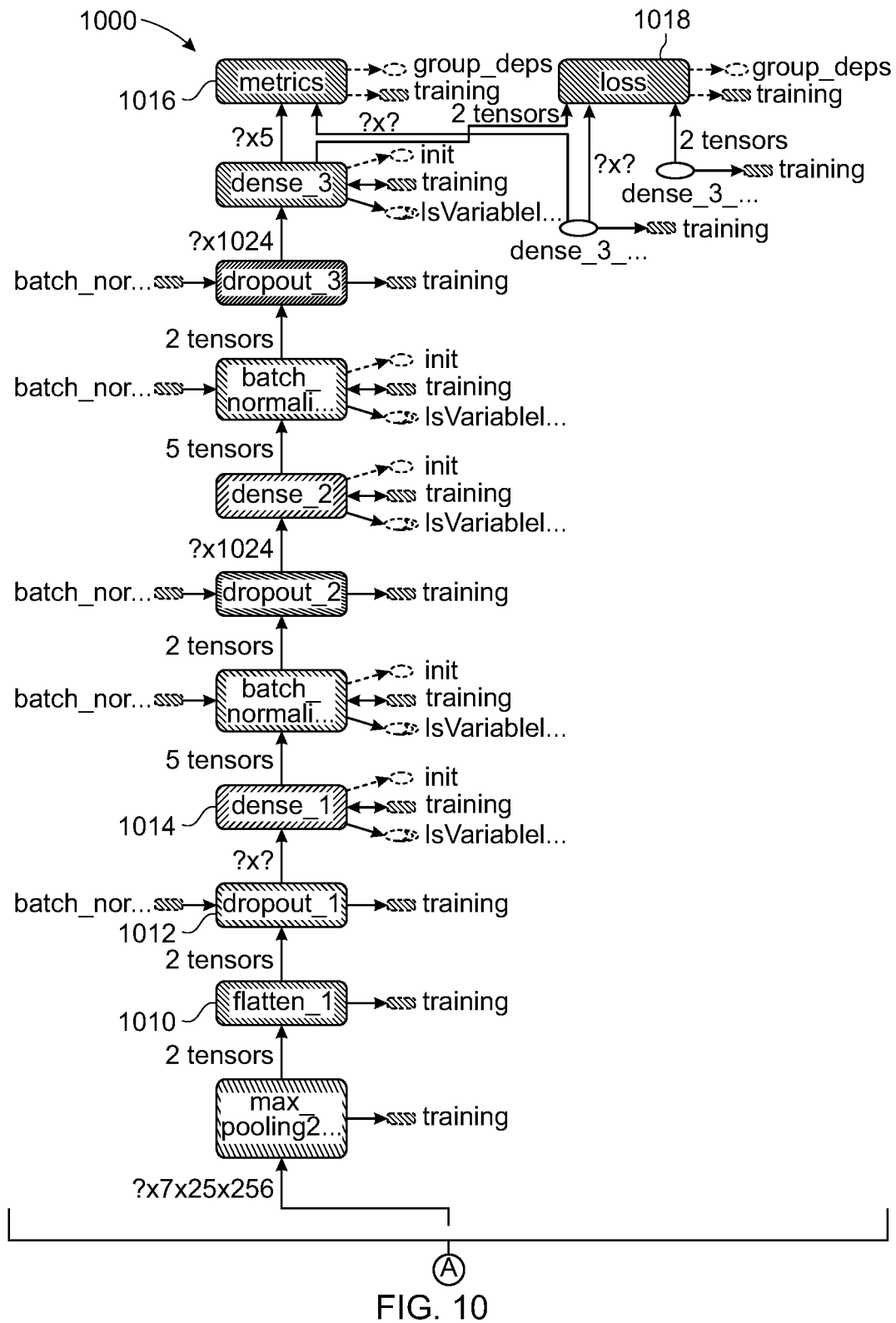
FIGS. 10 and 11 depict diagrams of ML models for inference of a gesture.
Figure 11:
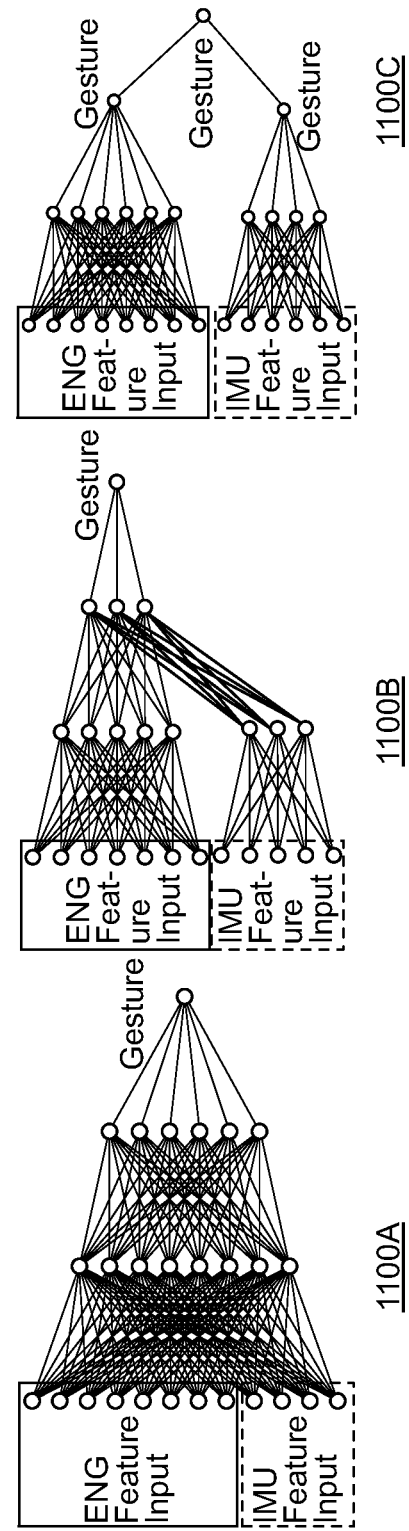

FIGS. 10 and 11 depict diagrams 1000, 1100A, 1100B, and 1100C of ML models for inference of a gesture. Diagrams 1000, 1100A, 1100B, and 1100C depict various alternative arrangements of ML models. Diagrams 1000, 1100A, 1100B, and 1100C depicting alternative arrangements of ML models may apply to features of FIGS. 1-9 and 12-15B herein.

In diagram 1000, diagram 1000 may depict a convolutional neural network (CNN). For instance, the CNN may include various components, connected in series (e.g., input from one layer to another layer), connected in parallel (e.g., input from one layer to another layer), or connected in feedback (e.g., input from one a layer closer to an output side to a layer close to an input side). In this case, the CNN may include at least an input feature vector 1002, at least one convolutional layer 1004, at least one pooling layer 1006, at least one batch normalization layer 1008, at least one flattening layer 1010, at least one dropout layer 1012, at least one dense layer 1014 (or fully connected layer), at least one metrics layer 1016, and at least one loss function 1018.

Generally, neural networks discussed herein may be specifically configured neural networks. A neural network may have one or more hidden layers of nodes, in addition to an input layer of nodes, and an output layer of nodes. The number of hidden layers may depend on the particular implementation, and may be, for example, 2 or more, 5 or more, 10 or more, 25 or more, 50 or more, 100 or more, etc. The number of nodes within each layer, and the number of total nodes in the neural network may depend on the particular implementation. For example, the number of total nodes in the one or more hidden layers may be 5 or more, 10 or more, 50 or more, 100 or more, 500 or more, etc. The number of nodes in the input and output layers may depend on the input variables and desired output of the particular implementation. In the neural network, each node of each layer before the output layer may have a connection to each node of the next layer, and may have a respective weight for each of the connections to the nodes of the next layer. Alternatively, each node of each layer before the output layer may have a connection to one or more node(s) of the next layer, and may have a respective weight for each of the connections to the nodes of the next layer. For example, if a first hidden layer includes nodes $a_1$, $a_2$, $a_3$, $a_4$, and $a_5$, and the next layer includes nodes $b_1$, $b_2$, $b_3$, and $b_4$, then the node $a_1$ may have weights $w_{a1b1}$, $w_{a1b2}$, $w_{a1b3}$, and $w_{a1b4}$, respectively corresponding to its connections to nodes $b_1$, $b_2$, $b_3$, and $b_4$. Likewise, the node $a_2$ may have weights $w_{a2b1}$, $w_{a2b2}$, $w_{a2b3}$, and $w_{a2b4}$, respectively corresponding to its connections to nodes $b_1$, $b_2$, $b_3$, and $b_4$. The weights of a node may be used as a multiplier to the output of the node for purposes of input into the following node. In the example discussed above, the outputs of the first hidden layer nodes $a_1$, $a_2$, $a_3$, $a_4$, and $a_5$ into node $b_1$ may be respectively multiplied by weights $w_{a1b1}$, $w_{a2b1}$, $w_{a3b1}$, $w_{a4b1}$, and $w_{a5b1}$, to obtain weighted outputs. The weighted output may be used as an input parameter for a function that determines or affects the output of node $b_1$. For example, the weighted outputs may be summed, and the sum may be input into an activation function of the node $b_1$. The activation function of the node $b_1$, as well as any other node, may be any suitable function, such as a sigmoidal function, a logistic function, a hyperbolic tangent function, or a rectified linear unit function, etc.

Furthermore, generally, when a neural networks' architecture is discussed, it refers to all the decisions a modeler may make, such as: what are the inputs, what basic blocks/layers (e.g., CNN, RNN, Dense layer etc.) to use, forward pass (how information moves from inputs to the outputs), backward pass (how information moves backward), what kind of nonlinear function to use, how to regularize the model (dropout, batch normalization etc.), what loss function to use, etc. In the CNN, all of the components may be either completely changed or tailored for video, biopotential, and/or IMU based gesture inference.

While certain characteristics of a neural network have been discussed herein for purposes of illustration, it is understood that the neural network to which methodologies of this disclosure may be applied may have any characteristic of neural networks now known or later developed.

Moreover, the CNN may have different components connected in different arrangements based on a type of sensor data being input to the CNN. For instance, in some cases, the CNN may process (1) ENG data, (2) ENG data and IMU data, (3) ENG data, IMU data, and video data, formatted in feature vectors. In cases where the CNN does not process IMU data or video data (or where IMU data or video data is processed in an additional manner), a different one or more ML model(s) (e.g., a classifier model or neural network) may process the IMU data and/or the video data, formatted in feature vectors. As an example, IMU data and ENG data fusion may take one of the three strategies: early fusion, intermediate fusion, or late fusion.

In diagram 1100A, the diagram 1100A may depict early fusion of IMU data and ENG data. In this example, the ENG data and the IMU data (formatted as input vectors) are directly concatenated as input vectors to a multimodal neural network. The multimodal neural network may infer the gesture based on the concatenated joint input vectors.

In diagram 1100B, the diagram 1100B may depict intermediate fusion of IMU data and ENG data. In this example, marginal ENG and IMU features (e.g., features determined and output by one or more of: the at least one convolutional layer 1004, the at least one pooling layer 1006, the at least one batch normalization layer 1008, the at least one flattening layer 1010, the at least one dropout layer 1012, and/or the at least one dense layer 1014) may be fused together from separate initial branches (where each branch processes ENG data or IMU data separately before fusing together) of the multimodal neural network.

In diagram 1100C, the diagram 1100C may depict late fusion of IMU data and ENG data. In this example, the marginal ENG features and IMU features may be used respectively to infer gestures, and the two inferred gestures may be used to determine a final gesture inference.

Gesture Inference Using Computer Vision

Figure 12:
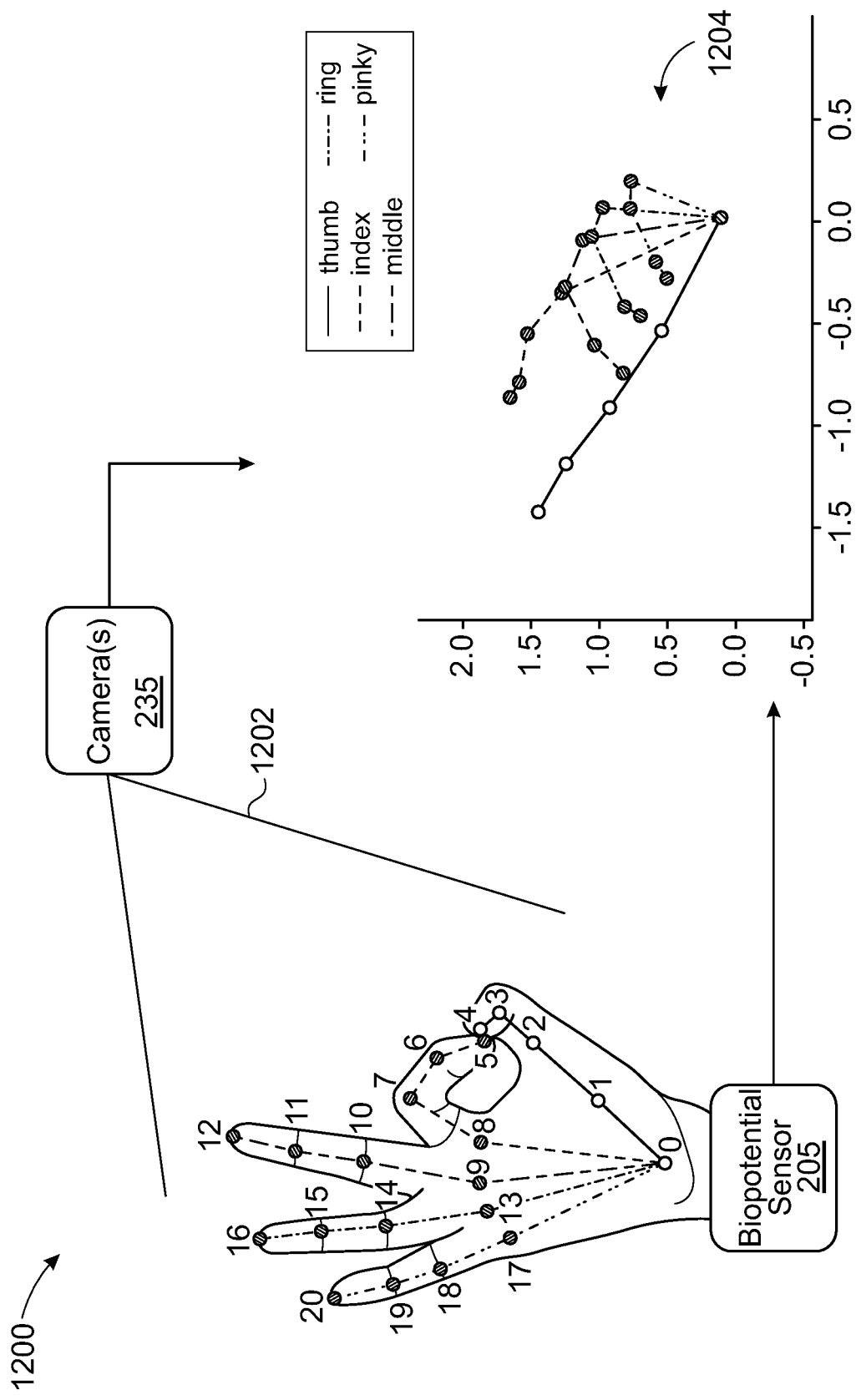
FIGS. 12 and 13 depict aspects of inferring gestures using computer vision and a biopotential sensor.
Figure 13:
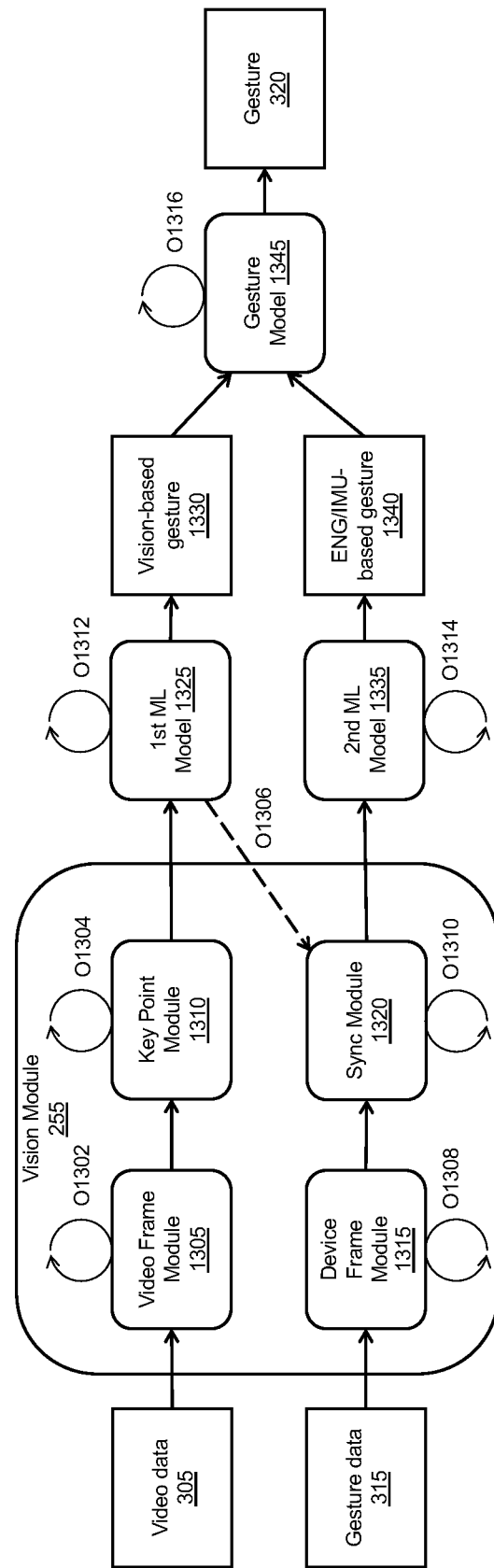

FIGS. 12 and 13 depict aspects of inferring gestures using computer vision and a biopotential sensor. FIG. 12 depicts an environment 1200 depicting camera(s) 235 and biopotential sensor 205 inferring a gesture 1204 in a field of view 1202 of the camera(s) 235. The environment 1200 depicting camera(s) 235 and biopotential sensor 205 inferring a gesture 1204 in a field of view 1202 of the camera(s) 235 may apply to features of FIGS. 1-11 and 13-15B herein. In some cases, the ML pipeline 230 may determine a gesture as a part of a multimodal sensing system (e.g., based on video data and gesture data) and/or as part of a multimodal sensing system (e.g., based on gesture data) that was trained on video data and/or gesture data. Thus, in some cases, the ML pipeline 230 may be used to infer a gesture based on gesture data of the session data or infer a gesture based on gesture data and video data of the session data, depending on if the session data includes video data or not.

In some cases, the ML pipeline 230 may use the video data to train a ML model based on a portion of the gesture data. In some cases, the ML pipeline 230 may use the video data to select a portion of the gesture data, so that the ML model using the gesture data yields higher accuracy and/or is a higher accuracy ML model. In some cases, the ML pipeline 230 may train a ML model that infers gestures based on gesture data (e.g., biopotential signals and/or IMU signal) on labels determined by a ML model that infers gestures based on video data. In training or inference sessions, the ML model may sync video data and gesture data, so that data from different sensor systems is characterizing a same gesture of the user. In some cases, the ML pipeline 230 may determine inferences based on different modalities (e.g., vision-based inferences and ENG/IMU inferences) and determine a final gesture inference based on agreement or confidence levels thereof. In this manner, training of ENG/IMU ML models may be accelerated and/or have their accuracy/robustness improved. In some cases, the ENG/IMU ML models may be supplemented by vision-based ML models, so that overall accuracy of the ML pipeline 230 is improved in complex environments. For instance, the complex environments may include with or without the wearable device 110 in the field of view 1202 of the camera(s) 235, if the wearable device 110 is occluded from the field of view 1202 of the camera(s) 235, the environment is dark (e.g., low light situation), and the like.

In some cases, ML pipeline 230 may include a first ML model (e.g., a vision ML model) and a second ML model (e.g., the IMU ML model and/or the ENG/IMU ML model). The first ML model may be configured to output a first gesture inference of the user's hand/arm based on a plurality of sets of key-point values determined based on image(s) of the environment from a video (e.g., of the camera(s) 235). In some cases, the first gesture inference may indicate a gesture from a plurality of defined gestures.

The second ML model may be configured to output a second gesture inference of the user's hand/arm using a combination at least the biopotential data and the motion data relating to the motion of the portion of the arm of the user, as discussed herein.

In some cases, the ML pipeline 230 may obtain the image(s) of the environment from the video, and determine a plurality of sets of key-point values. As discussed herein, each set of key-point values may indicate locations of portions of a hand of the user for an image of the image(s). For instance, the key-points may correspond to joints of a wrist and/or hand of a user. For instance, the sets of key-point values (e.g., with timestamps from video data) may correspond to positions of joints of the wrist and/or hand of the user over time (e.g., as the user wrist/hand performs a gesture). In some cases, the key-point values may be determined by computer-vision algorithms, such as open pose or others. For instance, in FIG. 12, the gesture 1204 may depict a predefined number of key-point values at a particular point in time (e.g., for a full hand extension). In this case, twenty key-point values.

In some cases, as discussed herein, the ML pipeline 230 (or another component) may determine a presence of a user hand/wrist/arm in the field of the field of view 1202 of the camera(s) 235 (e.g., using the image recognition software), determine a presence of a wearable device 110 on the wrist/arm (e.g., using the image recognition software), and in response to determining the presence of the hand/wrist/arm and/or the wearable device 110 on the wrist/arm, determine the sets of key-point values. Each set of key-point values may correspond to a single image timestamp (e.g., for a particular point in time). A series of sets of key-point values may track the user hand/wrist/arm over time.

In some cases, the ML pipeline 230 may, using the first ML model, process the plurality of sets of key-point values to obtain the first gesture inference. In some cases, the ML pipeline 230 may train the first ML model on a set of training data to process the plurality of sets of key-point values to obtain the first gesture inference. The training data may include training images (e.g., of video of training sessions of test subjects) and labels. For instance, the ML pipeline 230 may train the first ML model in the cloud (e.g., with data on the server 130) or based on calibration sessions of the user (with access to video data of the user) performing known gestures (or in response to timed stimuli). In this case, the ML pipeline 230 may obtain training image(s) from a training video of the hand/wrist/arm of the user performing a gesture. The training image(s) may have training image frame(s) (e.g., images and timestamps corresponding to training video). The ML pipeline 230 may determine a plurality of training sets of key-point values. For instance, the ML pipeline 230 may determine the plurality of training sets of key-point values based on the training image(s) (e.g., via open pose). As discussed herein, each training set of key-point values may indicate locations of portions of the hand of the user for a training image frame of the training image frame(s).

In some cases, the ML pipeline 230 may determine a label for portions of the training images. For instance, the ML pipeline 230 may determine a ground truth label for a gesture corresponding to the training image frame (or set of frames).

The ML pipeline 230 may train the first ML model to infer the first gesture inference based on: (1) one or more feature vectors based on the plurality of training sets of key-point values; and (2) ground truth data based on the ground truth label. For instance, given a sufficiently large training data set of example gestures, the first ML model may be able to infer the plurality of defined gestures. In some cases, the plurality of defined gestures may include a plurality of hand states or motions. In some cases, the same set of a plurality of hand states or motions may be recognized by both the first ML model and the ML learning model. In some cases, the plurality of hand states or motions may be converted to machine interpretable events by the ML pipeline 230 (or the application(s)).

In some cases, the ML pipeline 230 may determine the ground truth label for the gestures by: obtaining user input(s), determining the gestures using classical ML models, and/or outlier models of expected distributions. For instance, in the case of user inputs, the ML pipeline 230 may receive/obtain a user input indicating a gesture to correspond to the gesture inference (e.g., a label). For instance, the wearable device 110 or the user device 115 may receive a user input indicating a type of gesture, or the user may perform a known gesture in response to stimuli (e.g., an interactive game), or a user input may label a video of a user (or another user) performing a known gesture. In this manner, known gestures may be mapped to known labels, so as to train the first ML model. In some cases, the same data may be used to train the second ML model. However, user input labeling may be slow and/or hard to scale to populations of users, thus the ML pipeline 230 may rely on additional sources of training data.

In some cases, to achieve a large enough data set for training, the ML pipeline 230 may determine a first estimated gesture inference based on a plurality of gesture statistical conditions and the plurality of training sets of key-point values. For instance, each gesture statistical condition may correspond to one of the plurality of defined gestures, and each gesture statistical condition have threshold values. The threshold values may include thresholds for one or combinations: magnitudes of values of key-point values, differentials of the values of the key-point values, rates of change of the values of the key-point values, or statistical features of the plurality of training sets of key-point values. In this manner, lower confidence inference and/or lower robustness ML models, may assist training of higher confidence inference and/or higher robustness ML models.

In some cases, to achieve a large enough data set for training, the ML pipeline 230 may determine a second estimated gesture inference based on clustering of data. For instance, the ML pipeline 230 may cluster the plurality of training sets of key-point values and/or the statistical features of the plurality of training sets of key-point values with respect to defined clusters. In some cases, the defined clusters may correspond to one of the plurality of defined gestures. In this manner, the examples of the training data may be considered sufficiently similar (e.g., based on a cosine similarity score) to the defined clusters for defined gestures (e.g., from test subjects). In this manner, the training data set may be grown over time, as additional users are added to the environment.

In some cases, the ML pipeline 230 may, based on the image timestamps, assign a first gesture inference timestamp to the first gesture inference. In some cases, the first gesture inference timestamp may include: (1) a starting timestamp of the gesture, or (2) the starting timestamp and an end timestamp of the gesture. For instance, the ML pipeline 230 may determine a starting timestamp and/or end timestamp of the gesture based on the first ML model. For instance, the first ML model may output starting timestamp and/or end timestamp. In some cases, the first ML model may provide a range of image timestamps that correspond to the first gesture inference, as a range of first gesture inference timestamps.

In some cases, the ML pipeline 230 may select a subset of the biopotential data and the motion data having sensor data timestamps that overlap the first gesture inference timestamp (or range of the gesture inference timestamp). For instance, the ML pipeline 230 may select sensor data that has sensor data timestamps overlaps (e.g., is within a threshold time of the starting timestamp and an end timestamp, or the range of image timestamps). In some cases, the ML pipeline 230 may select the subset of the biopotential data and the motion data having the sensor data timestamps that overlap the first gesture inference timestamp, by selecting a subset of data packets based on the first gesture inference timestamp. As discussed herein, the biopotential data and the motion data may be transmitted/processed in data packets. Thus, in some cases, only subsets of data packets that overlap the first gesture inference timestamp may be selected by the ML pipeline 230.

In some cases, the ML pipeline 230 may use the second machine learning model to process the subset of the biopotential data and the motion data to generate the second gesture inference. In some case, the second gesture inference may be a training inference, a training prediction, a training classification, an inference, a prediction, or a classification, depending on a type of ML model being used by the ML pipeline 230.

In some cases, the ML pipeline 230 may, based on at least a comparison between the first gesture inference and the second gesture inference, modify the second machine learning model. In some case, in training of the second ML model, a number of observations (e.g., of training date) may be processed, in an interactive manner, through the second ML model with a loss function to train the second ML second model. In some cases, in training of the second ML model, a number of observations (e.g., of training date) may be processed to determine parameters of the second ML model. In some cases, the second ML model may be trained with/without a loss function. In some cases, the second ML model may be a statistical model determined based on the training data.

In some cases, the ML pipeline 230 may detect the wearable device is on the portion of the arm of the user by: detecting, in at least one image of the image(s) of the video, the wearable device 110 in a field of view 1202 of the at least one camera (e.g., camera(s) 235) and on the portion of the arm/wrist of the user. In some cases, the ML pipeline 230 may detect the wearable device is on the portion of the arm of the user by: determining the gesture data (e.g., the biopotential data) satisfies an outlier detection condition, and thus proceed with training and/or inference using the ML pipeline 230 with computer vision and gesture data.

In some cases, the ML pipeline 230 may, after the second ML model has been modified: obtain new biopotential data and new motion data; process the new biopotential data and the new motion data through the second ML model to obtain a new second gesture inference for the new biopotential data and the new motion data; based on at least the new second gesture inference, determine a machine interpretable event. In this case, the ML pipeline 230 may enable gesture inference using the trained ENG/IMU model, without the vision-based ML model. The ML pipeline 230 may then determine a machine interpretable event based on the gesture inference.

In some cases, the ML pipeline 230 may, after the second ML. model has been modified: obtain new image(s) (e.g., of new video), new biopotential data, and new motion data; determine a new plurality of sets of key-point values; process the new plurality of sets of key-point values through the first ML model to obtain a new first gesture inference; sync new sensor data timestamps and new image timestamps for the new image(s), the new biopotential data, and the new motion data; process the synced the new biopotential data and the new motion data through the second ML model to obtain a new second gesture inference for the new biopotential data and the new motion data. In this case, the ML pipeline 230 may enable inference using the trained vision-model and the ENG/IMU model. For instance, based on at least the new first gesture inference and the new second gesture inference, the ML pipeline 230 may determine a gesture. The ML pipeline 230 may then determine a machine interpretable event based on the gesture inference.

In some cases, the ML pipeline 230 may execute an action corresponding to the machine interpretable event, as discussed herein. For instance, an action may be define based on context and the machine interpretable event (e.g., indicated by the inferred gesture of the user).

In some cases, the ML pipeline 230 may determine the machine interpretable event by inputting the new first gesture inference and the new second gesture inference to a third machine learning model. The third ML model may output the machine interpretable event. The third ML model may be a ML model that weighs each inference from the first ML model and the second ML model (if available), and determines a final gesture inference.

FIG. 13 depicts a block diagram 1300 depicting operations O1302 through O1316 to infer a gesture based on video and ENG/IMU data. Diagram 1300 depicting operations O1302 through O1316 to infer a gesture based on video and ENG/IMU data may apply to features of FIGS. 1-12 and 14-15B herein. In particular, the diagram 1300 depicts aspects of the vision module 255, including a video frame module 1305, a key-point module 1310, a device frame module 1315, and a sync module 1320, along with a first ML model 1325, a second ML model 1335, and a gesture model 1345.

In operation O1302, the video frame module 1305 may obtain video data 305 from a camera (such as camera(s) 235) and determine whether a user's hand/wrist/arm in a field of view 1202 of the camera. In some cases, the video frame module 1305 may determine a presence of a hand/wrist/arm of the user (e.g., using image recognition software) in the field of view 1202 of the camera and/or determine a presence of a wearable device 110 on the wrist/arm (e.g., using the image recognition software) in the field of view 1202 of the camera, as discussed herein. In response to determining at least the user's hand/wrist/arm in the field of view 1202 of the camera, the video frame module 1305 may select a set of the video data 305 (e.g., segments where the hand/wrist/arm are in field of view), and transmit the selected set to the key-point module 1310.

In the case that the video frame module 1305 determines the presence of the hand/wrist/arm of the user in the field of view 1202 of the camera and the presence of the wearable device 110 on the (e.g., same) wrist/arm the in the field of view 1202 of the camera, the video frame module 1305 may flag the portion of sensor data (e.g., this segment of video data) as a gesture with video data and (possible) gesture data. In this case, the ML pipeline 230 may receive relevant gesture data (e.g., if sufficient data packets are received) and use multi-model inference using both vision data and ENG/IMU data.

In the case that the video frame module 1305 determines the presence of the hand/wrist/arm of the user in the field of view 1202 of the camera but no presence of the wearable device 110 on the (e.g., same) wrist/arm the in the field of view 1202 of the camera, the video frame module 1305 may flag the portion of sensor data (e.g., this segment of video data) as a gesture with video data and without gesture data (e.g., vision-only based gesture inference). In this case, gesture data may be obtained but that gesture may not be seen in the field of view.

In the case that the video frame module 1305 determines no presence of the hand/wrist/arm of the user in the field of view 1202 of the camera and no presence of the wearable device 110 on the (e.g., same) wrist/arm the in the field of view 1202 of the camera, the video frame module 1305 may flag the portion of sensor data (e.g., this segment of video data) as a gesture without video data and possibly with gesture data. In this case, the ML pipeline 230 may receive relevant gesture data (e.g., if sufficient data packets are received) and use multi-model inference on only ENG/IMU data.

In some cases, the video frame module 1305 may break the video data 305 (e.g., for test collection sessions or longer calibration sessions) time periods of video into smaller discrete periods. For instance, each discrete period may correspond to known gestures or gesture sequences. The video frame module 1305 may receive data indicating the discrete periods from, e.g., user inputs or a log of an interactive game, etc. The discrete periods may enable training of the first or second ML model, without having to calculate more key-point times for segments of time where no gesture is being performed.

In operation O1304, the key-point module 1310 may generate image-based data. The image-based data may include a plurality of sets of key-point values. For instance, the key-point module 1310 may receive the selected set to the from the video frame module 1305, and generate the image-based data. Each set of key-point values may indicate locations of portions of a hand of the user for an image of the image(s). In some cases, the image-based data may also include image timestamps for each set of key-point values. The image timestamps may correspond to a timestamp of each image of the video data 305 that was processed to determine the set of key-point values. The key-point module 1310 may transmit the image-based data to the first ML model 1325.

In operation O1312, the first ML model 1325 may infer a vision-based gesture 1330. In some cases, the first ML model 1325 may infer the vision-based gesture 1330 based on the image-based data, such as the plurality of sets of key-point values and/or the image timestamps. In some cases, the first ML model 1325 may, based on the image timestamps, assign a first gesture inference timestamp to vision-based gesture 1330. The first gesture inference timestamp may be a start window a gesture inferred by the first ML model 1325, or the first gesture inference timestamp may be a range from the start of the start window to an end point. The first ML model 1325 may infer the start point and/or end point timestamp when inferring the vision-based gesture 1330

In operation O1306, the first ML model 1325 may transmit the first gesture inference timestamp to the sync module 1320. In some cases, the key-point module 1310 may only determine to transfer the first gesture inference timestamp, when the presence of the hand/wrist/arm of user is detected, when the presence of the wearable device 110 is on the wrist/arm is detected, and/or when the first ML model 1325 infers a gesture (e.g., at least one inference has a confidence above a threshold).

In operation O1308, the device frame module 1315, may receive gesture data 315 and determine, e.g., one or more pre-process task(s), check(s), or transformations. For instance, the device frame module 1315 may receive gesture data from at least one biopotential sensor 205, and perform functions similar to the pre-process module 405, discussed herein. In some cases, the device frame module 1315 may receive, buffer (e.g., store), and determine whether sufficient data (e.g., data packets over time) has been received to infer a gesture. The device frame module 1315 may transmit the gesture data 315 (e.g., as buffered) to the sync module 1320.

In operation O1310, the sync module 1320 may select a subset of the gesture data 315 (e.g., the biopotential data and the motion data) that have sensor data timestamps that overlap the first gesture inference timestamp. In some cases, the sync module 1320 may only select a subset of the gesture data 315 in response to receiving the first gesture inference timestamp from the first ML model 1325. In this case, the sync module 1320 may avoid larger sets of data (e.g., of gesture data), thereby reducing computational/memory requirements to infer a gesture. In some cases, the sync module 1320 may not select the subset of the gesture data 315 if the sync module 1320 did not receive the first gesture inference timestamp from the first ML model 1325. In this case, the sync module 1320 may pass all (or at least a subset) of the gesture data 315 to the second ML model 1335.

In some cases, the sync module 1320 may sync training data, as outlined above. For instance, the sync module 1320 may sync training data for the second ML model 1335 to ensure ground truth labels (e.g., determined by the first ML model) are time-synced to gesture data, to thereby provide high quality training/calibration data for the second ML model. In certain circumstances, gathering enough high-quality training/calibration data may be a challenge, and these systems and methods may enable faster training/higher accuracy models, on a per-user basis or on a user population basis. For instance, in some cases, the sync module 1320 may time-sync calibration data from a video feed and the gesture data, so as to calibrate/adjust the ENG/IMU models based on a separately trained vision model.

In operation O1314, the second ML model 1335 may infer an ENG/IMU-based gesture 1340. In some cases, the second ML model 1335 may infer the ENG/IMU-based gesture 1340 based the gesture data 315 (or subsets selected thereof), as discussed herein. In the case that the sync module 1320 indicates a relevant period (e.g., where a vision-based gesture is inferred), the second ML model 1335 may provide higher confidence inferences and/or be more robust to inputs, as the second ML model 1335 may infer gestures based on an identified time window (e.g., based on sensor data timestamps that overlap the first gesture inference timestamp).

In operation O1316, the gesture model 1345 may infer a gesture 320. In some cases, the gesture model 1345 may infer the gesture 320 based on the ENG/IMU-based gesture 1340 and/or the vision-based gesture 1330, as discussed herein. In some cases, the gesture model 1345 may infer the gesture 320 based on the vision-based gesture 1330 and the ENG/IMU-based gesture 1340 when both are available (e.g. by a selection algorithm). In some cases, the gesture model 1345 may infer the gesture 320 based on the ENG/IMU-based gesture 1340 when the vision-based gesture 1330 is not available (e.g. by the selection algorithm). In some cases, the gesture model 1345 may infer the gesture 320 based on the vision-based gesture 1330 when the ENG/IMU-based gesture 1340 is not available (e.g. by the selection algorithm).

In some cases, the gesture model 1345 may determine the gesture 320 based on a combination the ENG/IMU-based gesture 1340 and the vision-based gesture 1330, or a highest confidence inference of the ENG/IMU-based gesture 1340 and the vision-based gesture 1330. In some cases, the gesture model 1345 may determine the gesture 320 based on whether the ENG/IMU-based gesture 1340 and the vision-based gesture 1330 are available to the gesture model 1345. In some cases, the gesture model 1345 may determine the gesture 320 only if both the ENG/IMU-based gesture 1340 and the vision-based gesture 1330 are available. In some cases, the gesture model 1345 may determine the gesture 320 based on weights of the ENG/IMU-based gesture 1340 and the vision-based gesture 1330. For instance, the gesture model 1345 may determine the gesture 320 at a higher confidence level if the ENG/IMU-based gesture 1340 and the vision-based gesture 1330 are available, while the gesture model 1345 may determine the gesture at a lower confidence level when only one of the ENG/IMU-based gesture 1340 or the vision-based gesture 1330 are available.

Selection of ML Model

Figure 14:
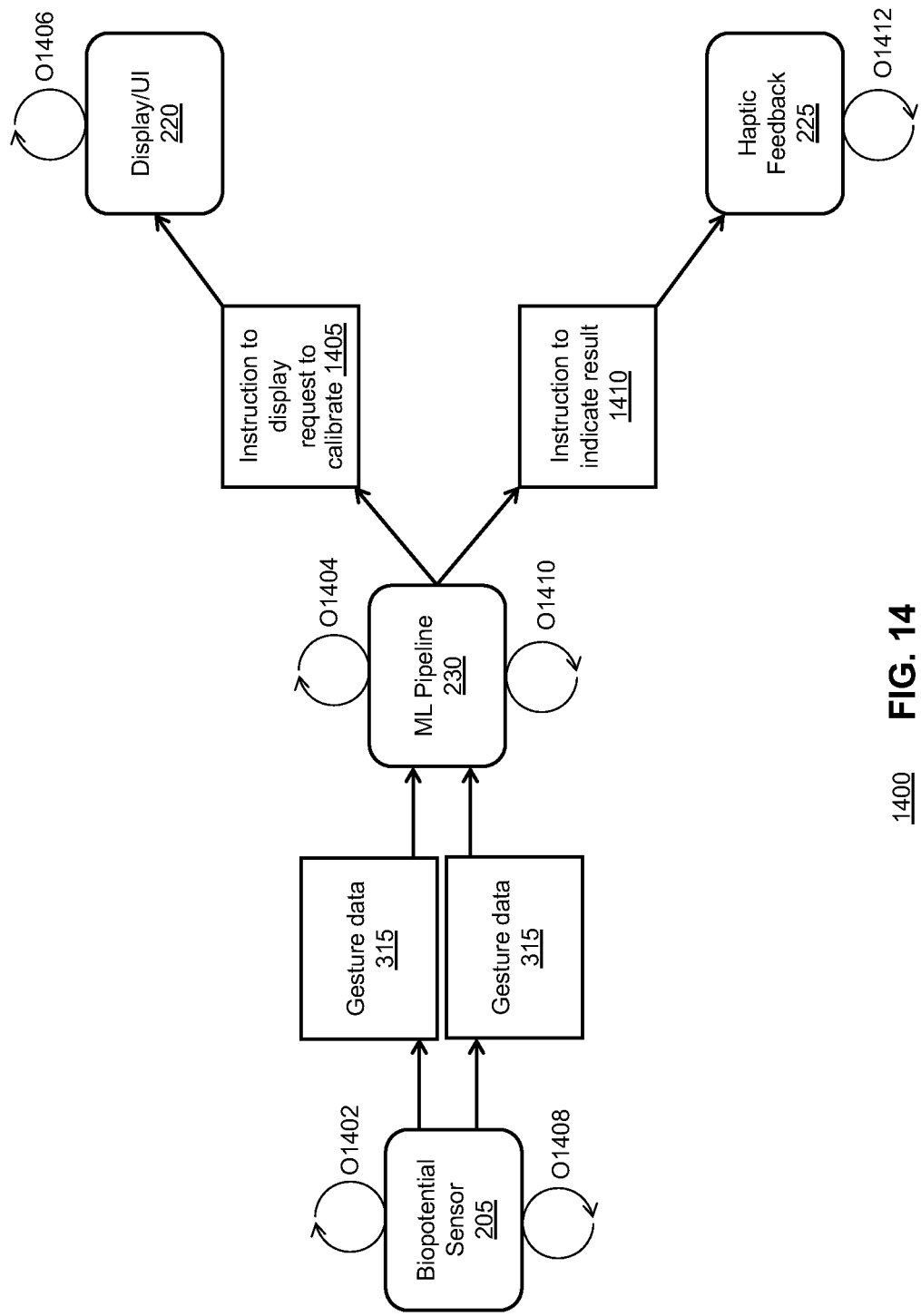
FIG. 14 depicts a block diagram of aspects of selecting a ML model.
Figure 15A:
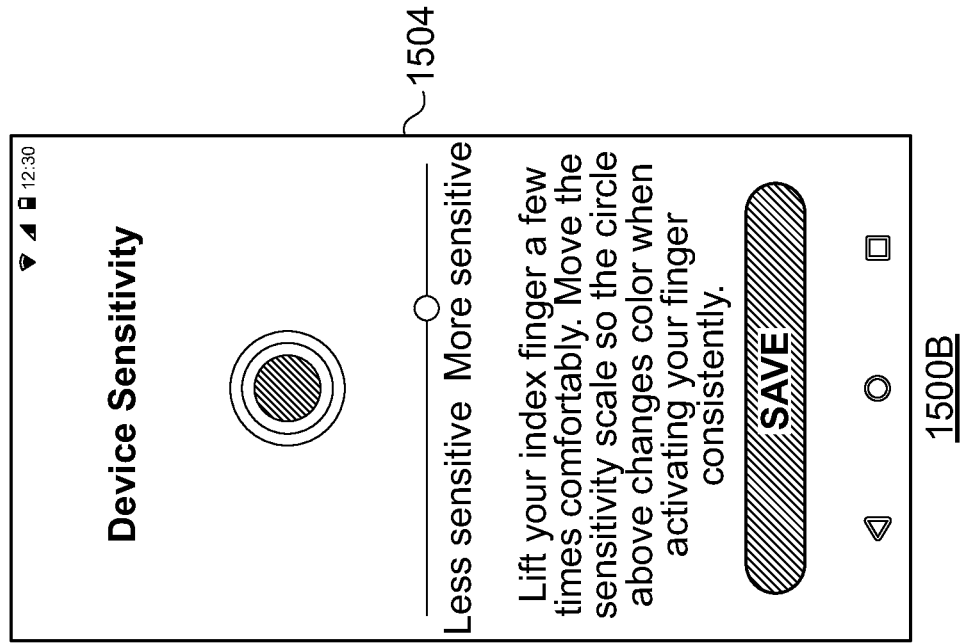
FIGS. 15A and 15B depict graphical user interfaces of aspects of selecting a ML model.
Figure 15A:
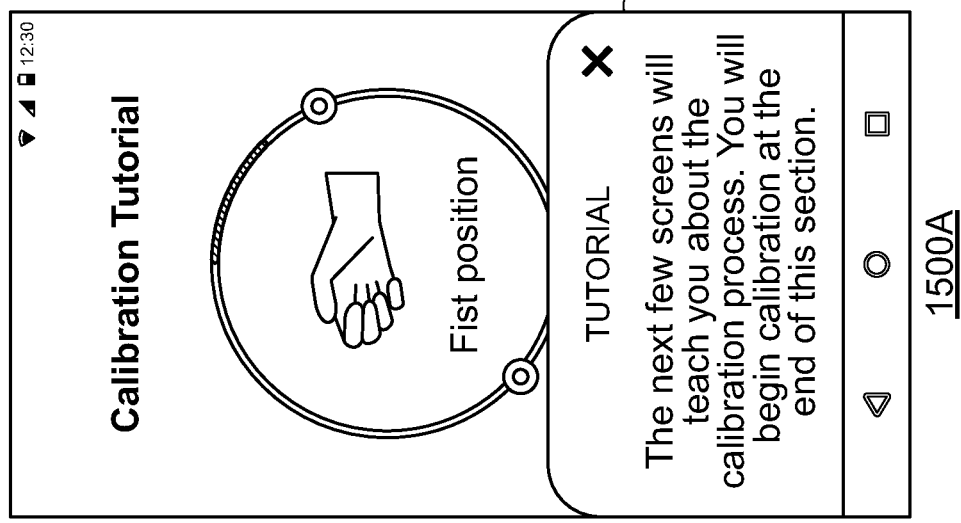
Figure 15B:
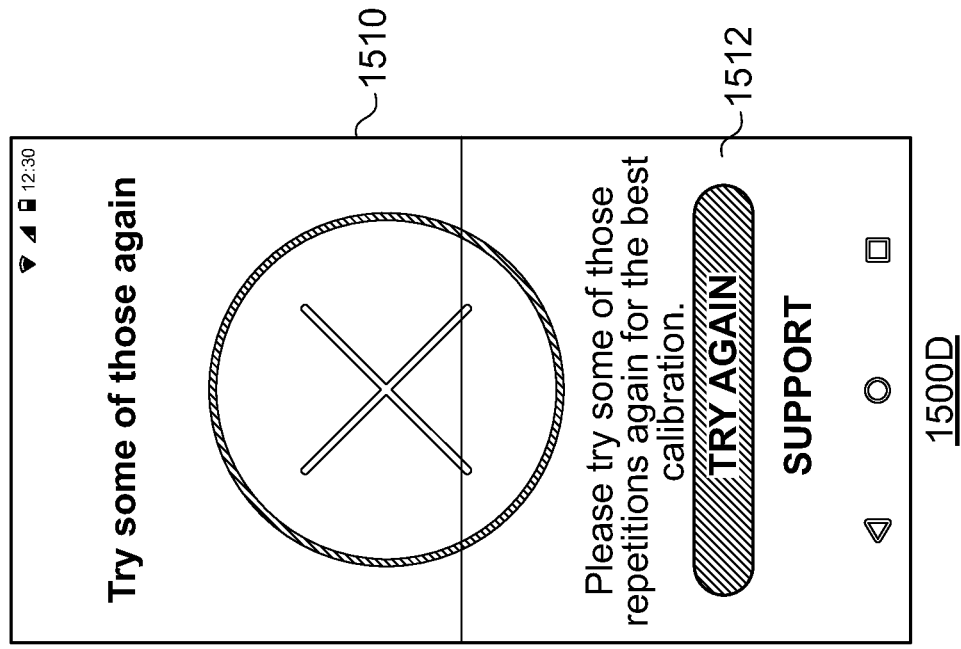
Figure 15B:
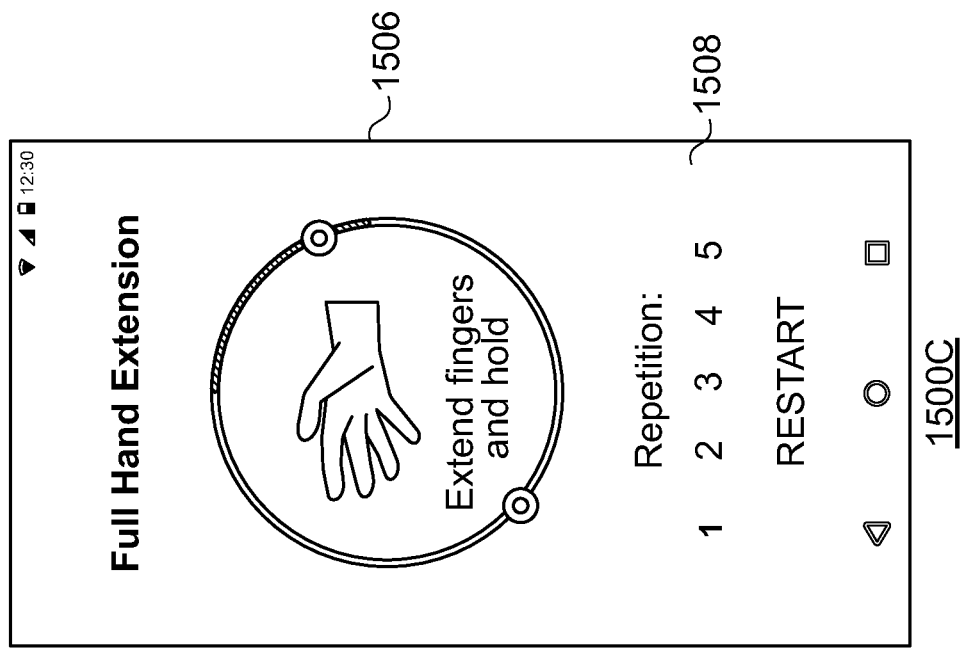

FIGS. 14, 15A, and 15B depict aspects of selecting a ML model. FIG. 14 depicts a block diagram 1400 of aspects of selecting a ML model. The block diagram 1400 depicts operations O1402 through O1412 to select a ML model. Diagram 1400 depicting operations O1402 through O1412 to select a ML model may apply to features of FIGS. 1-13 and 15A-15B herein.

In operation O1402, the biopotential sensor 205 may obtain gesture data 315. The biopotential sensor 205 may obtain gesture data 315 and determine, e.g., one or more pre-process task(s), check(s), or transformations. For instance, the device frame module 1315 may obtain gesture data 315 at a first instance from at least one biopotential sensor 205, and perform functions similar to the pre-process module 405, discussed herein. The biopotential sensor 205 may transmit the gesture data 315 to the ML pipeline 230 ("first gesture data").

In some cases, the ML pipeline 230 may determine an inference using a base ML model. In some case, ML pipeline 230 may determine an inference after calibrating the system, e.g., for a user, for a session, and the like, so that the base ML model is adjusted to a user-specific model.

In operation O1404, the ML pipeline 230 may determine to prompt the user to perform a first action. In some cases, the ML pipeline 230 may, before prompting the user to perform the first action, determine whether a trigger condition is satisfied. In some cases, the trigger condition may be satisfied when the wearable device 110 is initialized to a user during on initial bootup sequence. In some cases, the trigger condition may be satisfied when the gesture data 315 is for a new session after a period of time that the wearable device 110 was not worn by the user. For instance, the period of time may be 5 minutes, 12 hours, 24 hours and the like. In some cases, the trigger condition may be satisfied when the ML pipeline 230 (or another component of the environment) assesses that one or more gestures were likely to have been m is-inferred or erroneously not inferred. For instance, in some cases, the ML pipeline 230, when the ML pipeline 230 has access to video data 305, the ML pipeline 230 may detect and determine vision-based inference(s) and, if one or a threshold number of disagreements to detected, or confidence differences are exceeded, the ML pipeline 230 may determine that the ENG/IMU based inferences are being m is-inferred or not inferred. In some cases, the ML pipeline 230 may determine that gesture inferences are below a threshold confidence level while also determining the session data is not an outlier (e.g., by the outlier module 415), thereby indicating the ML pipeline 230 may require (re) calibration.

In some cases, to determine that the first action was performed by the user, the ML pipeline 230 may use at least the base ML model and the session data to generate a first gesture inference. The ML pipeline 230 may then determine whether the first gesture inference matches a gesture inference for the first action. For instance, the ML pipeline 230 may store a record of what first action was prompted and determine whether the first gesture inference matches the record. In response to determining the first gesture inference does not match the gesture inference for the first action, the ML pipeline 230 may prompt the user to perform a different action or a same action but with a different intensity. A different intensity may be a rate of change or speed of fingers (e.g., extension or contraction), or rate of change or speed of motion (e.g., of a wrist rotation), and the like. In some cases, the outlier module 415 may determine whether a first action was performed by the user, instead or addition to the base ML model.

In some cases, to determine that the first action was performed by the user, the ML pipeline 230 may determine the session data does not satisfy one or more conditions. In response to determining the session data does not satisfy one or more conditions, the ML pipeline 230 may then prompt the user to perform a different action or a same action but with a different intensity. For instance, the one or more conditions may be based on (1) time differentials (of when action is requested and signals are received), (2) amplitude of signals (e.g., of individual electrodes, differentials of electrodes, and the like), and (3) distances (e.g., between pairs or defined sets of key-points) and rates of change thereof.

In operation O1406, the UI 220 may output a user interface to request the user to calibrate the wearable device 110, based on instructions to display a request to calibrate 1405 from the ML pipeline 230. While the UI 220 is depicted as the user interface, any other suitable methods may be utilized, such as the haptic feedback module 225, the UI 250, and the like. For instance, the request to the user to calibrate the wearable device 110 may include instructions, data, feedback, and/or interactive games.

In operation O1408, the biopotential sensor 205 may obtain gesture data 315. The biopotential sensor 205 may obtain gesture data 315 and determine, e.g., one or more pre-process task(s), check(s), or transformations, as discussed herein. For instance, the device frame module 1315 may obtain gesture data 315 at a first instance from at least one biopotential sensor 205, and perform functions similar to the pre-process module 405, discussed herein. The biopotential sensor 205 may transmit the gesture data 315 to the ML pipeline 230. For instance, the biopotential sensor 205 may obtain, gesture data while the user performs the first action ("second gesture data").

In operation O1410, the ML pipeline 230 may select, based on at least the first gesture data and/or second gesture data, a second ML model. The second ML model may be selected to provide improved inference accuracy for the user as compared to the base ML model. In some cases, based on the first gesture data and/or second gesture data, the ML pipeline 230 may (i) assess an inference accuracy or sensitivity of the second ML model for the user, or (ii) modify the second ML model.

In some cases, the ML pipeline 230 may determine a selected/modified ML model is sufficient for inference, and output an indication to the user. Thus, the ML pipeline 230 may output an instruction to indicate result 1410 of success (or not) of selecting the ML model.

In operation O1412, the haptic feedback module 225 may vibrate to indicate success (or not) of selecting the ML model. While the haptic feedback module 225 is depicted as the user interface, any other suitable methods may be utilized, such as the UI 220, the UI 250, and the like.

In some cases, after selecting the second ML model, the biopotential sensor 205 may obtain gesture data 315 ("third gesture data"). The ML pipeline 230 may, using at least the second ML model and third gesture data, generate an inference output indicating that the user performed an action.

In some cases, the ML pipeline 230 may prompt the user to perform a second action after the second ML model has been selected. In this case, the ML pipeline 230 may confirm the second action has been performed based on gesture data 315 and an accuracy and/or robustness of the second ML model may be confirmed.

In some cases, the ML pipeline 230 may, to select the second ML model based on session data: determine sensor data features of the first sensor data; and select the second ML model from a set of ML models based on the sensor data features. In some cases, the sensor data features may include image features, IMU features, and/or ENG features. In some cases, the sensor data features may include one or combinations of: time domain ENG features of the biopotential data; frequency domain ENG features of the biopotential data; temporal-spatial descriptor-based features; IMU features of the IMU data; discrete wavelet transform features of the biopotential data and/or IMU data; continuous wavelet transform features of the biopotential data and/or IMU data; short-time Fourier transform features of the biopotential data and/or IMU data; derivatives of the sensor data; and/or learned latent features determined by a ML model.

In some cases, to select the second ML model based on session data, the ML pipeline 230 may compare the sensor data features to a set of model feature clusters. The ML pipeline 230 may, based on the comparison, select a model feature cluster that is closest to the sensor data features, and obtain a ML model that corresponds to the selected model feature cluster as the second ML model. In some cases, each model feature cluster corresponds to one ML model of a plurality of ML models. In some cases, the model feature clusters may be determined (e.g., by the server 130) from session data from one or a plurality of calibration sessions in different types of known circumstances. A calibration session in a known circumstance may be a known circumstance (e.g., normal, wet, high heartrate, high movement circumstances) having an operating environment/situation and for known user gestures. In some cases, the calibration session may instruct the user on how to place the wearable device 110 and when to perform the known user gestures. In some cases, the wearable device 110 may instruct the user on how to perform the known user gestures or the user may perform known user gestures in response to timed stimuli (e.g., an interactive game, and the like). The data that forms the clusters may be clusters within a feature space (like feature space 602). Thus, the feature space may include N dimensions (N being a number corresponding to aspects of the components of the data). The data may include a predefined number of clusters, so as to compare incoming session data to the clusters of each ML model, so to determine a similarity score for the incoming session data to each of the clusters of each ML model. The similarity score may be based on a cosine similarity score, Bhattacharyya distance, Hellinger distance, Mahalanobis distance, Earth mover's distance, kullback-leibler divergence, and the like. Each ML model may be trained or tuned based on session data of corresponding the clusters. Thus, each ML model may perform with better accuracy and/or in a more robust manner, given its similar clustering pattern to the clusters a selected ML model of the plurality of ML models.

In some cases, the ML pipeline 230 may determine a distance (or similarity score) between the sensor data features and the model feature cluster that is closest to the sensor data features. For instance, the distance function may a multi-variable distance function, as discussed herein (e.g., a cosine similarity score, Bhattacharyya distance, Hellinger distance, Mahalanobis distance, Earth mover's distance, kullback-leibler divergence, and the like). The ML pipeline 230 may then determine adjustments to the ML model that corresponds to the selected model feature cluster based on the distance; and apply the adjustment to the ML model to obtain the second ML model. In some cases, the adjustments may include one or more of weights, biases, thresholds, or values of the ML model. In the case the ML model includes a classical ML model (e.g., a linear regression classifier, and the like), the adjustments may modify thresholds, conditions, policies, window sizing, and the like. In the case the ML model includes a neural network, the adjustments may modify weights, biases, activation values of one or more layers (e.g., a fully connected, end layer) of the neural network. In some cases, the adjustment may be a change in a magnitude (and direction) of the weights, biases, thresholds, or values that match a magnitude (and direction) of the difference.

In some cases, to select the second ML model based on session data, the ML pipeline 230 may compare embeddings of the feature space. For instance, instead of comparing manually-combined feature data (and/or session data), you can reduce (e.g., the dimension and size of data) the feature data to embedding representations, and then compare the embedding representations. Embedding representations may be generated by training a (e.g., supervised) deep neural network (DNN) on the session data (e.g., sensor data and/or feature data thereof) of calibration sessions. The embedding representations map the feature data to a vector in an embedding space (different than the feature space). In some cases, the embedding space has fewer dimensions than the feature space of the feature data. In some cases, the embedding space captures latent structure of the feature data set. The ML pipeline 230 may compare the embedded vectors using a similarity score, such as a cosine similarity or a distance measure (e.g., Bhattacharyya distance, Hellinger distance, Mahalanobis distance, Earth mover's distance, kullback-leibler divergence, and the like). In some cases, this may be more efficient than directly comparing feature clusters in the feature space of the feature clusters.

In some cases, latent features may be learned using encoder-decoder model. The encoder takes the session data (of calibration data) and learns a latent feature space. The decoder then takes the learned latent feature space and tries to reconstruct the original session data. The objective function of the encoder is to minimize the difference between the original signal and the reconstructed signal, and training on the calibration data may adjust parameters of the encoder-decoder model to minimize the difference. At inference, the encoder may determine latent space features of the real-time session data, and the ML pipeline 230 may compare the latent space features of the real-time session data versus (each or subsets) of a set of class learned latent space features. Each one of the class learned latent space features may correspond to a specific ML model (e.g., DNN, encoder-decoder model, etc.) trained on a specific set of training data (e.g., class of calibration data). The class learned latent space feature with a highest similarity score (e.g., using a cosine similarity or a distance measure (e.g., Bhattacharyya distance, Hellinger distance, Mahalanobis distance, Earth mover's distance, kullback-leibler divergence, and the like)) to the latent space features of the real-time session data may be selected as the ML model.

In some cases, to select the second ML model based on session data, the ML pipeline 230 may determine latent-space features of the first sensor data. The ML pipeline 230 may determine the latent-space features of the first sensor data by applying transformations to the session data. For instance, in the case the ML model includes a neural network, a first portion (e.g., nearer an input side) of the ML model may include one or more layers that output marginal IMU features, marginal ENG features, and/or marginal ENG/IMU features. The ML model may select all or a subset of the marginal IMU features, marginal ENG features, and/or marginal ENG/IMU features as the latent-space features of the first sensor data.

The ML pipeline 230 may then obtain a set of latent-space distributions. Each latent-space distribution may correspond to a set of training data that was used to train a ML model of a plurality of ML models. Each latent-space distribution may be a set of marginal IMU features, marginal ENG features, and/or marginal ENG/IMU features determined by the one or more layers on the training data. In this manner, the distribution may reflect a structure of latent-space features for different training datasets, thereby addressing inter/inter-session variability, using a marginal feature based on session data.

The ML pipeline 230 may then determine distances between the latent-space features of the first sensor data and each of the set of latent-space distributions. For instance, the ML pipeline 230 may determine multi-variable distances, as discussed herein. The ML pipeline 230 may then select a latent-space distribution that has a smallest distance, and obtain a ML model that corresponds to the selected latent-space distribution as the second ML model.

In some cases, the ML pipeline 230 may then determine adjustments to the ML model, that corresponds to the selected latent-space distribution, based on the distance (that was smallest). The ML pipeline may then apply the adjustment to the ML model to obtain the second ML model. In some cases, the adjustments may include one or more of weights, biases, thresholds, or values of the ML model. In the case the ML model includes a classical ML model (e.g., a linear regression classifier, and the like), the adjustments may modify thresholds, conditions, policies, window sizing, and the like. In the case the ML model includes a neural network, the adjustments may modify weights, biases, activation values of one or more layers (e.g., a fully connected, end layer) of the neural network. In some cases, the adjustment may be a change in a magnitude (and direction) of the weights, biases, thresholds, or values that match a magnitude (and direction) of the difference.

FIGS. 15A and 15B depict graphical user interfaces 1500A through 1500D of aspects of selecting a ML model. The graphical user interfaces 1500A through 1500D depict user interactions to select a ML model. The graphical user interfaces 1500A through 1500D depict user interactions to select a ML model may apply to features of FIGS. 1, 2A-2B, and 3-14 above. In some cases, the graphical user interfaces 1500A through 1500D may be displayed by the wearable device 110 and/or the user device 115 (referred to as display device hereinafter).

In some cases, the display device may start by displaying graphical user interfaces 1500A. The graphical user interfaces 1500A may display instructions, data, and/or context 1502 to a user. In some cases, the graphical user interfaces 1500A may receive a user input (e.g., a gesture and the like) to proceed. In some cases, the graphical user interfaces 1500A may proceed to the graphical user interfaces 1500B, and/or the graphical user interfaces 1500C, based on the user input.

In some cases, the display device may proceed to display graphical user interfaces 1500B. The graphical user interfaces 1500B may display a sensitivity interface 1504. In some cases, the sensitivity interface 1504 may enable a user (via user inputs) to adjust a sensitivity of one or more parameters of the wearable device 110 and/or user device 115.

In some cases, the display device may proceed to display graphical user interfaces 1500C. The graphical user interfaces 1500C may one or more reptations 1508 of a defined gesture 1506. In some cases, the graphical user interfaces 1500C may indicate a completion rate of one or more reptations 1508 the gesture 1506, in graphic of numerical form, so that the user is informed where in the process the user is progressing. In the case that the user successfully performs the one or more repetitions, for each type of gesture, the display device may indicate success in calibration/selection of a ML model based on the session data.

In some cases, the display device may proceed to display graphical user interface 1500D. The graphical user interface 1500D may display a request to repeat one or more repetitions, for at least one type of gesture, if the display device determines that the calibration/selection of a ML model based on the session data was insufficient. For instance, the calibration data may be considered an outlier by the outlier module 415. In this case, the graphical user interface 1500D may indicate a negative outcome 1510 and a retry element 1512. The retry element 1512 may be user selectable to start over portions or all of the calibration/ML model selection process.

Computer System

Figure 16:
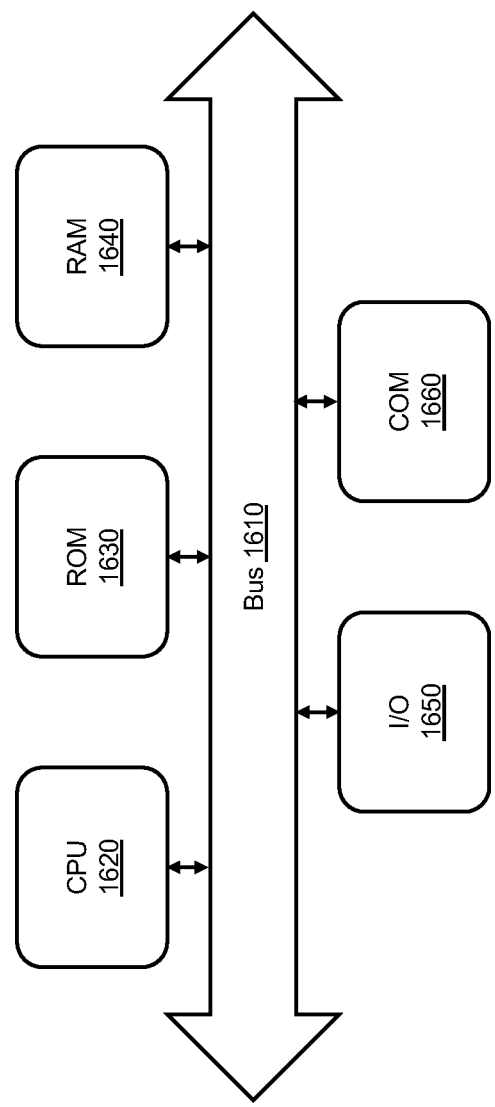
FIG. 16 depicts an example system that may execute techniques presented herein.

FIG. 16 depicts an example system that may execute techniques presented herein. FIG. 16 is a simplified functional block diagram of a computer that may be configured to execute techniques described herein, according to exemplary cases of the present disclosure. Specifically, the computer (or "platform" as it may not be a single physical computer infrastructure) may include a data communication interface 1660 for packet data communication. The platform may also include a central processing unit ("CPU") 1620, in the form of one or more processors, for executing program instructions. The platform may include an internal communication bus 1610, and the platform may also include a program storage and/or a data storage for various data files to be processed and/or communicated by the platform such as ROM 1630 and RAM 1640, although the system 1600 may receive programming and data via network communications. The system 1600 also may include input and output ports 1650 to connect with input and output devices such as keyboards, mice, touchscreens, monitors, displays, etc. Of course, the various system functions may be implemented in a distributed fashion on a number of similar platforms, to distribute the processing load. Alternatively, the systems may be implemented by appropriate programming of one computer hardware platform.

The general discussion of this disclosure provides a brief, general description of a suitable computing environment in which the present disclosure may be implemented. In some cases, any of the disclosed systems, methods, and/or graphical user interfaces may be executed by or implemented by a computing system consistent with or similar to that depicted and/or explained in this disclosure. Although not required, aspects of the present disclosure are described in the context of computer-executable instructions, such as routines executed by a data processing device, e.g., a server computer, wireless device, and/or personal computer. Those skilled in the relevant art will appreciate that aspects of the present disclosure can be practiced with other communications, data processing, or computer system configurations, including: Internet appliances, hand-held devices (including personal digital assistants ("PDAs")), wearable computers, all manner of cellular or mobile phones (including Voice over IP ("VoIP") phones), dumb terminals, media players, gaming devices, virtual reality devices, multi-processor systems, microprocessor-based or programmable consumer electronics, set-top boxes, network PCs, mini-computers, mainframe computers, and the like. Indeed, the terms "computer," "server," and the like, are generally used interchangeably herein, and refer to any of the above devices and systems, as well as any data processor.

Aspects of the present disclosure may be embodied in a special purpose computer and/or data processor that is specifically programmed, configured, and/or constructed to perform one or more of the computer-executable instructions explained in detail herein. While aspects of the present disclosure, such as certain functions, are described as being performed exclusively on a single device, the present disclosure may also be practiced in distributed environments where functions or modules are shared among disparate processing devices, which are linked through a communications network, such as a Local Area Network ("LAN"), Wide Area Network ("WAN"), and/or the Internet. Similarly, techniques presented herein as involving multiple devices may be implemented in a single device. In a distributed computing environment, program modules may be located in both local and/or remote memory storage devices.

Aspects of the present disclosure may be stored and/or distributed on non-transitory computer-readable media, including magnetically or optically readable computer discs, hard-wired or preprogrammed chips (e.g., EEPROM semiconductor chips), nanotechnology memory, biological memory, or other data storage media. Alternatively, computer implemented instructions, data structures, screen displays, and other data under aspects of the present disclosure may be distributed over the Internet and/or over other networks (including wireless networks), on a propagated signal on a propagation medium (e.g., an electromagnetic wave(s), a sound wave, etc.) over a period of time, and/or they may be provided on any analog or digital network (packet switched, circuit switched, or other scheme).

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

Terminology

The terminology used above may be interpreted in its broadest reasonable manner, even though it is being used in conjunction with a detailed description of certain specific examples of the present disclosure. Indeed, certain terms may even be emphasized above; however, any terminology intended to be interpreted in any restricted manner will be overtly and specifically defined as such in this Detailed Description section. Both the foregoing general description and the detailed description are exemplary and explanatory only and are not restrictive of the features, as claimed.

As used herein, the terms "comprises," "comprising," "having," including," or other variations thereof, are intended to cover a non-exclusive inclusion such that a process, method, article, or apparatus that comprises a list of elements does not include only those elements, but may include other elements not expressly listed or inherent to such a process, method, article, or apparatus.

In this disclosure, relative terms, such as, for example, "about," "substantially," "generally," and "approximately" are used to indicate a possible variation of ±10% in a stated value.

The term "exemplary" is used in the sense of "example" rather than "ideal." As used herein, the singular forms "a," "an," and "the" include plural reference unless the context dictates otherwise.

Examples

Exemplary embodiments of the systems and methods disclosed herein are described in the numbered paragraphs below.

A1. A system for gesture inference, the system comprising:

at least one camera configured to capture video having image(s) of an environment, the image(s) having image timestamps;

a wearable device configured to be worn on a portion of an arm of a user, the wearable device comprising:
 a biopotential sensor, the biopotential sensor being configured to obtain biopotential data indicating electrical signals generated by nerves and muscles in the arm of the user; and
 a motion sensor, the motion sensor being configured to obtain motion data relating to a motion of the portion of the arm of the user, the biopotential data and/or the motion data having sensor data timestamps;

a first machine learning model, the first machine learning model being configured to output a first gesture inference of the user's hand/arm based on a plurality of sets of key-point values determined based on the image(s) of the environment from the video, the first gesture inference indicating a gesture from a plurality of defined gestures; and a second machine learning model, the second machine learning model being configured to output a second gesture inference of the user's hand/arm using a combination at least the biopotential data and the motion data relating to the motion of the portion of the arm of the user;

wherein the system is configured to:
 obtain the image(s) of the environment from the video;
 determine a plurality of sets of key-point values, each set of key-point values indicating locations of portions of a hand of the user for an image of the image(s);
 using the first machine learning model, process the plurality of sets of key-point values to obtain the first gesture inference;
 based on the image timestamps, assign a first gesture inference timestamp to the first gesture inference;
 select a subset of the biopotential data and the motion data having sensor data timestamps that overlap the first gesture inference timestamp;
 using the second machine learning model, process the subset of the biopotential data and the motion data to generate the second gesture inference; and
 based on at least a comparison between the first gesture inference and the second gesture inference, modify the second machine learning model.

A2. The system of A1, wherein the system is configured to detect the wearable device is on the portion of the arm of the user by: (1) detecting, in at least one image of the image(s), the wearable device in a field of view of the at least one camera and on the portion of the arm of the user, and/or (2) determining the biopotential data satisfies an outlier detection condition.

A3. The system of any of A1-A2, wherein the first gesture inference timestamp includes: (1) a starting timestamp of the gesture, or (2) the starting timestamp and an end timestamp of the gesture.

A4. The system of any of A1-A3, wherein the biopotential data and the motion data are processed in data packets, and, to select the subset of the biopotential data and the motion data having the sensor data timestamps that overlap the first gesture inference timestamp, the system is configured to: select a subset of data packets based on the first gesture inference timestamp.

A5. The system of any of A1-A4, wherein the system is configured to, after the second machine learning model has been modified:
 obtain new biopotential data and new motion data;
 process the new biopotential data and the new motion data through the second machine learning model to obtain a new second gesture inference for the new biopotential data and the new motion data;
  based on at least the new second gesture inference, determine a machine interpretable event; and
  execute an action corresponding to the machine interpretable event.

A6. The system of any of A1-A4, wherein the system is configured to, after the second machine learning model has been modified:
  obtain new image(s), new biopotential data, and new motion data;
  determine a new plurality of sets of key-point values;
  process the new plurality of sets of key-point values through the first machine learning model to obtain a new first gesture inference;
  sync new sensor data timestamps and new image timestamps for the new image(s), the new biopotential data, and the new motion data;
  process the synced the new biopotential data and the new motion data through the second machine learning model to obtain a new second gesture inference for the new biopotential data and the new motion data;
  based on at least the new first gesture inference and the new second gesture inference, determine a machine interpretable event; and
  execute an action corresponding to the machine interpretable event.

A7. The system of A6, wherein, to determine the machine interpretable event, the system is configured to: input the new first gesture inference and the new second gesture inference to a third machine learning model; and output, from the third machine learning model, the machine interpretable event.

A8. The system of any of A1-A7, wherein the plurality of defined gestures includes a plurality of hand states or motions that are configured to be recognized by both the first machine learning model and the second machine learning model and converted to machine interpretable events by the system.

A9. The system of any of A1-A8, wherein, to train the first machine learning model, the system is configured to:
  obtain training image(s) from a training video of the hand of the user performing a gesture, the training image(s) having training image frame(s);
  determine a plurality of training sets of key-point values, each training set of key-point values indicating locations of portions of the hand of the user for a training image frame of the training image frame(s);
  determine a ground truth label for the gesture; and
  train the first machine learning model to infer the first gesture inference based on: (1) one or more feature vectors based on the plurality of training sets of key-point values; and (2) ground truth data based on the ground truth label.

A10. The system of A9, wherein, to determine the ground truth label for the gesture, the system is configured to:
  obtain a user input indicating a gesture inference;
  determine a first estimated gesture inference based on a plurality of gesture statistical conditions and the plurality of training sets of key-point values, each gesture statistical condition corresponding to one of the plurality of defined gestures, each gesture statistical condition having threshold values for one or combinations: magnitudes of values of key-point values, differentials of the values of the key-point values, rates of change of the values of the key-point values, or statistical features of the plurality of training sets of key-point values; and/or
  determine a second estimated gesture inference based on clustering of the plurality of training sets of key-point values and/or the statistical features of the plurality of training sets of key-point values with respect to defined clusters, each of the defined clusters corresponding to one of the plurality of defined gestures.

A11. A computer-implemented method for gesture inference, the computer-implemented method comprising:
  obtaining, from at least one camera, image(s) of an environment from a video, the at least one camera being configured to capture the video, the image(s) having image timestamps;
  determining a plurality of sets of key-point values based on the image(s) of the environment from the video, each set of key-point values indicating locations of portions of a hand of a user for an image of the image(s);
  using a first machine learning model, processing the plurality of sets of key-point values to obtain a first gesture inference, the first machine learning model being configured to output the first gesture inference of the user's hand/arm based on the plurality of sets of key-point values, the first gesture inference indicating a gesture from a plurality of defined gestures;
  based on the image timestamps, assigning a first gesture inference timestamp to the first gesture inference;
  obtaining biopotential data from a biopotential sensor of a wearable device and motion data from a motion sensor of the wearable device, the biopotential sensor being configured to obtain the biopotential data indicating electrical signals generated by nerves and muscles in the arm of the user; the motion sensor being configured to obtain the motion data relating to a motion of the portion of the arm of the user, the biopotential data and/or the motion data having sensor data timestamps;
  selecting a subset of the biopotential data and the motion data having sensor data timestamps that overlap the first gesture inference timestamp;
  using a second machine learning model, processing the subset of the biopotential data and the motion data to generate a second gesture inference, the second machine learning model being configured to output the second gesture inference of the user's hand/arm using a combination at least the biopotential data and the motion data relating to the motion of the portion of the arm of the user; and based on at least a comparison between the first gesture inference and the second gesture inference, modifying the second machine learning model.

A12. The computer-implemented method of A11, wherein the computer-implemented method further includes: detecting the wearable device is on the portion of the arm of the user by: (1) detecting, in at least one image of the image(s), the wearable device in a field of view of the at least one camera and on the portion of the arm of the user, and/or (2) determining the biopotential data satisfies an outlier detection condition.

A13. The computer-implemented method of any of A11-A12, wherein the first gesture inference timestamp includes: (1) a starting timestamp of the gesture, or (2) the starting timestamp and an end timestamp of the gesture.

A14. The computer-implemented method of any of A11-A13, wherein the biopotential data and the motion data are processed in data packets, and, to select the subset of the biopotential data and the motion data having the sensor data timestamps that overlap the first gesture inference timestamp, the computer-implemented method further includes: selecting a subset of data packets based on the first gesture inference timestamp.

A15. The computer-implemented method of any of A11-A14, wherein the computer-implemented method further includes, after the second machine learning model has been modified:
 obtaining new biopotential data and new motion data;
 processing the new biopotential data and the new motion data through the second machine learning model to obtain a new second gesture inference for the new biopotential data and the new motion data;
 based on at least the new second gesture inference, determining a machine interpretable event; and
 executing an action corresponding to the machine interpretable event.

A16. The computer-implemented method of any of A11-A14, wherein the computer-implemented method further includes, after the second machine learning model has been modified:
 obtaining new image(s), new biopotential data, and new motion data;
 determining a new plurality of sets of key-point values;
 processing the new plurality of sets of key-point values through the first machine learning model to obtain a new first gesture inference;
 syncing new sensor data timestamps and new image timestamps for the new image(s), the new biopotential data, and the new motion data;
 processing the synced the new biopotential data and the new motion data through the second machine learning model to obtain a new second gesture inference for the new biopotential data and the new motion data;
 based on at least the new first gesture inference and the new second gesture inference, determining a machine interpretable event; and
 executing an action corresponding to the machine interpretable event.

A17. The computer-implemented method of A16, wherein, to determine the machine interpretable event, the computer-implemented method further includes: inputting the new first gesture inference and the new second gesture inference to a third machine learning model; and outputting, from the third machine learning model, the machine interpretable event.

A18. The computer-implemented method of any of A11-A17, wherein the plurality of defined gestures includes a plurality of hand states or motions that are configured to be recognized by both the first machine learning model and the second machine learning model and converted to machine interpretable events.

A19. The computer-implemented method of A11, wherein, to train the first machine learning model, the computer-implemented method further includes:
 obtaining training image(s) from a training video of the hand of the user performing a gesture, the training image(s) having training image frame(s);
 determining a plurality of training sets of key-point values, each training set of key-point values indicating locations of portions of the hand of the user for a training image frame of the training image frame(s);
 determining a ground truth label for the gesture; and
 training the first machine learning model to infer the first gesture inference based on: (1) one or more feature vectors based on the plurality of training sets of key-point values; and (2) ground truth data based on the ground truth label.

A20. The computer-implemented method of A19, wherein, to determine the ground truth label for the gesture, the computer-implemented method further includes:
 obtaining a user input indicating a gesture inference;
 determining a first estimated gesture inference based on a plurality of gesture statistical conditions and the plurality of training sets of key-point values, each gesture statistical condition corresponding to one of the plurality of defined gestures, each gesture statistical condition having threshold values for one or combinations: magnitudes of values of key-point values, differentials of the values of the key-point values, rates of change of the values of the key-point values, or statistical features of the plurality of training sets of key-point values; and/or
 determining a second estimated gesture inference based on clustering of the plurality of training sets of key-point values and/or the statistical features of the plurality of training sets of key-point values with respect to defined clusters, each of the defined clusters corresponding to one of the plurality of defined gestures.

B1. A system for gesture inference, the system comprising:
 a wearable device configured to be worn on a portion of an arm of a user, the wearable device comprising:
  a biopotential sensor, the biopotential sensor being configured to obtain biopotential data indicating electrical signals generated by nerves and muscles in the arm of the user; and
  a motion sensor, the motion sensor being configured to obtain motion data relating to a motion of the portion of the arm of the user, the motion data and biopotential data collectively being sensor data; and
 a processing pipeline configured to receive the biopotential data and the motion data and process the biopotential data and the motion data to generate a gesture inference output using a ML model, wherein the processing pipeline includes:
  a pre-process module configured to:
   obtain a first set of sensor data;
   determine, based on the sensor data or a derivative thereof, a first transformation to the ML model and/or a second transformation to the first set of sensor data; and
   apply the first transformation to the ML model to obtain a session ML model and/or apply the second transformation to the first set of sensor data or derivative thereof to obtain mapped sensor data; and
  an inference module configured to infer the gesture inference based on (1) the session ML model and the first set of sensor data, and/or (2) the ML model and the mapped sensor data;
 wherein the system is configured to, based on the gesture inference, determine a machine interpretable event, and execute an action corresponding to the machine interpretable event.

B2. The system of B1, wherein the processing pipeline further includes an outlier detection module configured to confirm the first set of sensor data and/or derivatives of the first set of sensor data are not an outlier.

B3. The system of B2, wherein the outlier detection module compares the first set of sensor data and/or the derivatives of the first set of sensor data to at least one statistical file, a first statistical file of the at least one statistical file includes a set of values, the set of values indicating a multi-variable distribution based on historical sensor data for known gestures.

B4. The system of B3, wherein the outlier detection module uses the first statistical file during calibration and a second statistical file during inference.

B5. The system of B4, wherein the first statistical file is based on data gathered from a population of users, and the second statistical file is based on calibration data gathered from the user during calibration.

B6. The system of any of B1-B5, wherein, to determine the first transformation to the ML model, the pre-process module is configured to:
 determine, based on the sensor data or derivative thereof, that the wearable device is in a deviated state relative to the arm of the user, the deviated state being known to modify the sensor data received by the wearable device according to a known deviation pattern relative to the sensor data that would be received by the wearable device if the wearable device were in a neutral state; and
 based on the determined deviated state, determine the first transformation to the ML model, the determined first transformation to the ML model being configured to improve inference accuracy of the ML model while the wearable device is in the deviated state.

B7. The system of B6, wherein the deviated state comprises a deviated arm posture that is different from a neutral arm posture when the wearable device is in a neutral state, and determining the first transformation to the ML model comprises:
 determining, based on the motion data, that the arm of the user is in the deviated arm posture.

B8. The system of any of B1-137, wherein the first transformation applies adjustments to one or more model parameters, wherein the model parameters include one or more of weights, biases, thresholds, or values of the ML model.

B9. The system of any of B1-B8, wherein, to determine the second transformation to the first set of sensor data, the pre-process module is configured to:
 determine, based on the sensor data, that the wearable device is in a deviated state relative to the arm of the user, the deviated state being known to modify the sensor data received by the wearable device according to a known deviation pattern relative to the sensor data that would be received by the wearable device if the wearable device were in a neutral state; and
 based on the determined deviated state, determine the second transformation to the first set of sensor data, the determined second transformation to the first set of sensor data being configured produce the mapped sensor data, which is more similar to the sensor data that would be received by the wearable device if the wearable device were in the neutral state than is the first set of sensor data.

B10. The system of any of B1-139, wherein the second transformation comprises a rotation, a translation, a projection, and/or a scaling, so that the first set of sensor data, as transformed to the mapped sensor data, is more similar to sensor data that would be received by the wearable device if the wearable device were in a neutral state.

B11. The system of any of B1-610, wherein the ML model includes a first ML model to infer an IMU gesture inference based on the motion data, and a second ML model to infer a biopotential gesture inference based on the biopotential data and the motion data, and the inference module determines the gesture inference based on the IMU gesture inference and the biopotential gesture inference.

B12. The system of B11, wherein the inference module is configured to:
 store successive biopotential gesture inferences;
 determine a threshold number of the successive biopotential gesture inferences have been stored; and
 determine the gesture inference based on the threshold number of the successive biopotential gesture inferences and probability information of a confusion matrix, the confusion matrix having been generated during training of the second ML model.

B13. A computer-implemented method for gesture inference, the computer-implemented method comprising:
 obtaining a first set of sensor data, the first set of sensor data including motion data and biopotential data, the motion data being obtained by a motion sensor of a wearable device, the motion sensor being configured to obtain the motion data relating to a motion of a portion of an arm of a user wearing the wearable device, the biopotential data being obtained by a biopotential sensor of the wearable device, the biopotential sensor being configured to obtain the biopotential data indicating electrical signals generated by nerves and muscles in the arm of the user;
 determining, based on the sensor data or a derivative thereof, a first transformation to a ML model and/or a second transformation to the first set of sensor data;
 applying the first transformation to the ML model to obtain a session ML model and/or applying the second transformation to the first set of sensor data or derivative thereof to obtain mapped sensor data; and
 inferring a gesture inference based on (1) the session ML model and the first set of sensor data, and/or (2) the ML model and the mapped sensor data;
 wherein the wearable device is configured to, based on the gesture inference, determine a machine interpretable event, and execute an action corresponding to the machine interpretable event.

B14. The computer-implemented method of B13, wherein, to determine the first transformation to the ML model, the computer-implemented method further includes:
 determining, based on the sensor data or derivative thereof, that the wearable device is in a deviated state relative to the arm of the user, the deviated state being known to modify the sensor data received by the wearable device according to a known deviation pattern relative to the sensor data that would be received by the wearable device if the wearable device were in a neutral state; and
 based on the determined deviated state, determining the first transformation to the ML model, the determined first transformation to the ML model being configured to improve inference accuracy of the ML model while the wearable device is in the deviated state.

B15. The computer-implemented method of B14, wherein the deviated state comprises a deviated arm posture that is different from a neutral arm posture when the wearable device is in a neutral state, and, to determine the first transformation to the ML model, the computer-implemented method further comprises:
 determining, based on the motion data, that the arm of the user is in the deviated arm posture.

B16. The computer-implemented method of B13-B15, wherein the first transformation applies adjustments to one or more model parameters, wherein the model parameters include one or more of weights, biases, thresholds, or values of the ML model.

B17. The computer-implemented method of any of B13-B16, wherein, to determine the second transformation to the first set of sensor data, the computer-implemented method further includes:
  determining, based on the sensor data, that the wearable device is in a deviated state relative to the arm of the user, the deviated state being known to modify the sensor data received by the wearable device according to a known deviation pattern relative to the sensor data that would be received by the wearable device if the wearable device were in a neutral state; and
  based on the determined deviated state, determining the second transformation to the first set of sensor data, the determined second transformation to the first set of sensor data being configured produce the mapped sensor data, which is more similar to the sensor data that would be received by the wearable device if the wearable device were in the neutral state than is the first set of sensor data.

B18. The computer-implemented method of any of B13-B17, wherein the second transformation comprises a rotation, a translation, a projection, and/or a scaling, so that the first set of sensor data, as transformed to the mapped sensor data, is more similar to sensor data that would be received by the wearable device if the wearable device were in a neutral state.

B19. The computer-implemented method of any of B13-B18, wherein the ML model includes a first ML model to infer an IMU gesture inference based on the motion data, and a second ML model to infer a biopotential gesture inference based on the biopotential data and the motion data, and the ML model determines the gesture inference based on the IMU gesture inference and the biopotential gesture inference.

B20. The computer-implemented method of B19, wherein the computer-implemented method further includes:
  storing successive biopotential gesture inferences;
  determining a threshold number of the successive biopotential gesture inferences have been stored; and
  determining the gesture inference based on the threshold number of the successive biopotential gesture inferences and probability information of a confusion matrix, the confusion matrix having been generated during training of the second ML model.

C1. A system for gesture inference, the system comprising:
  a wearable device configured to be worn on a portion of an arm of a user, the wearable device comprising:
    a biopotential sensor, the biopotential sensor being configured to obtain biopotential data indicating electrical signals generated by nerves and muscles in the arm of the user; and
    a motion sensor, the motion sensor being configured to obtain motion data relating to a motion of the portion of the arm of the user, the motion data and biopotential data collectively being sensor data; and a base ML model;
  wherein the system is configured to:
    prompt the user to perform a first action;
    obtain, using the biopotential sensor and the motion sensor, first sensor data while the user performs the first action;
    using at least the base ML model and the first sensor data, determine that the first action was performed by the user;
    select, based on at least the first sensor data, a second ML model, the second ML model being selected to provide improved inference accuracy for the user as compared to the base ML model;
    obtain, using the biopotential sensor and the motion sensor, second sensor data while the user performs a second action;
    using at least the second ML model and the second sensor data, generate an inference output indicating that the user performed the second action.

C2. The system of C1, wherein the system is configured to, before prompting the user to perform the first action, determine whether a trigger condition is satisfied.

C3. The system of C2, wherein the trigger condition is satisfied when the wearable device is initialized to a user during on initial bootup sequence or when the first sensor data is for a new session after a period of time that the wearable device was not worn by the user.

C4. The system of C2, wherein the trigger condition is satisfied when the system assesses that one or more gestures were likely to have been m is-inferred or erroneously not inferred.

C5. The system of any of C1-C4, wherein the system is further configured to: based on the second sensor data, (i) assess an inference accuracy or sensitivity of the second ML model for the user, or (ii) modify the second ML model.

C6. The system of any of C1-C5, wherein the system is further configured to, before obtaining the second sensor data while the user performs the second action:
  prompt the user to perform the second action after the second ML model has been selected.

C7. The system of any of C1-C6, wherein, to select the second ML model based on at least the first sensor data, the system is configured to:
  determine sensor data features of the first sensor data; and
  select the second ML model from a set of ML models based on the sensor data features.

C8. The system of C7, wherein the sensor data features include one or combinations of:
  time domain ENG features of the biopotential data;
  frequency domain ENG features of the biopotential data;
  temporal-spatial descriptor-based features;
  IMU features of the IMU data;
  discrete wavelet transform features of the biopotential data and/or IMU data;
  continuous wavelet transform features of the biopotential data and/or IMU data;
  short-time Fourier transform features of the biopotential data and/or IMU data;
  derivatives of the second set of sensor data; and/or
  learned latent features determined by second ML model.

C9. The system of any of C1-C8, wherein, to determine that the first action was performed by the user, the system is configured to:
  using at least the base ML model and the first sensor data, generate a first gesture inference;
  determine whether the first gesture inference matches a gesture inference for the first action; and
  in response to determining the first gesture inference does not match the gesture inference for the first action, prompt the user to perform a different action or a same action but with a different intensity.

C10. The system of any of C1-C8, wherein, to determine that the first action was performed by the user, the system is configured to: determine the first sensor data does not satisfy one or more conditions; and in response to determining the first sensor data does not satisfy one or more conditions, prompt the user to perform a different action or a same action but with a different intensity.

C11. The system of any of C1-C6 and C8-C10, wherein, to select the second ML model based on at least the first sensor data, the system is configured to:
determine sensor data features of the first sensor data;
obtain a set of model feature clusters, each model feature cluster corresponding to one ML model of a plurality of ML models;
compare the sensor data features to the set of model feature clusters;
based on the comparison, select a model feature cluster that is closest to the sensor data features; and
obtain a ML model that corresponds to the selected model feature cluster as the second ML model.

C12. The system of C11, wherein the system is configured to:
determine a distance between the sensor data features and the model feature cluster that is closest to the sensor data features;
determine adjustments to the ML model that corresponds to the selected model feature cluster based on the distance; and
apply the adjustment to the ML model to obtain the second ML model.

C13. The system of any of C1-C6 and C8-C10, wherein, to select the second ML model based on at least the first sensor data, the system is configured to:
determine latent-space features of the first sensor data;
obtain a set of latent-space distributions, each latent-space distribution corresponding to a set of training data that was used to train a ML model of a plurality of ML models;
determine distances between the latent-space features of the first sensor data and each of the set of latent-space distributions;
select a latent-space distribution that has a smallest distance; and
obtain a ML model that corresponds to the selected latent-space distribution as the second ML model.

C14. A computer-implemented method for gesture inference, the computer-implemented method comprising:
prompting a user to perform a first action;
obtaining, using a biopotential sensor of a wearable device and a motion sensor of the wearable, first sensor data while the user performs the first action, the biopotential sensor being configured to obtain biopotential data indicating electrical signals generated by nerves and muscles in an arm of the user, the motion sensor being configured to obtain motion data relating to a motion of a portion of the arm of the user, the motion data and biopotential data collectively being sensor data; and;
using at least a base ML model and the first sensor data, determining that the first action was performed by the user;
selecting, based on at least the first sensor data, a second ML model, the second ML model being selected to provide improved inference accuracy for the user as compared to the base ML model;
obtaining, using the biopotential sensor and the motion sensor, second sensor data while the user performs a second action; and
using at least the second ML model and the second sensor data, generate an inference output indicating that the user performed the second action.

C15. The computer-implemented method of C14, wherein the computer-implemented method further includes:
based on the second sensor data, (i) assessing an inference accuracy or sensitivity of the second ML model for the user, or (ii) modifying the second ML model.

C16. The computer-implemented method of any of C14-C15, wherein the computer-implemented method further includes, before obtaining the second sensor data while the user performs the second action: prompting the user to perform the second action after the second ML model has been selected.

C17. The computer-implemented method of any of C14-C16, wherein selecting the second ML model based on at least the first sensor data includes:
determining sensor data features of the first sensor data; and
selecting the second ML model from a set of ML models based on the sensor data features.

C18. The computer-implemented method of C17, wherein the sensor data features include one or combinations of:
time domain ENG features of the biopotential data;
frequency domain ENG features of the biopotential data;
temporal-spatial descriptor-based features;
IMU features of the IMU data;
discrete wavelet transform features of the biopotential data and/or IMU data;
continuous wavelet transform features of the biopotential data and/or IMU data;
short-time Fourier transform features of the biopotential data and/or IMU data;
derivatives of the second set of sensor data; and/or
learned latent features determined by second ML model.

C19. The computer-implemented method of any of C14-C18, wherein determining that the first action was performed by the user includes:
using at least the base ML model and the first sensor data, generating a first gesture inference;
determining whether the first gesture inference matches a gesture inference for the first action; and
in response to determining the first gesture inference does not match the gesture inference for the first action, prompting the user to perform a different action or a same action but with a different intensity.

C20. The computer-implemented method of any of C14-C18, wherein determining that the first action was performed by the user includes:
determining the first sensor data does not satisfy one or more conditions; and
in response to determining the first sensor data does not satisfy one or more conditions, prompting the user to perform a different action or a same action but with a different intensity.

Other aspects of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A system for gesture inference, the system comprising:
a wearable device configured to be worn on a portion of an arm of a user, the wearable device comprising:
a biopotential sensor, the biopotential sensor being configured to obtain biopotential data indicating electrical signals generated by nerves and muscles in the arm of the user; and a motion sensor, the motion sensor being configured to obtain motion data relating to a motion of the portion of the arm of the user, the motion data and biopotential data collectively being sensor data; and a processing pipeline configured to receive the biopotential data and the motion data and process the biopotential data and the motion data to generate a gesture inference output using a ML model, wherein the processing pipeline includes:

a pre-process module configured to:

obtain a first set of sensor data;

determine, based on the sensor data or a derivative thereof, a first transformation to the ML model and/or a second transformation to the first set of sensor data; and apply the first transformation to the ML model to obtain a session ML model and/or apply the second transformation to the first set of sensor data or derivative thereof to obtain mapped sensor data; and an inference module configured to infer the gesture inference based on (1) the session ML model and the first set of sensor data, and/or (2) the ML model and the mapped sensor data;

wherein the system is configured to, based on the gesture inference, determine a machine interpretable event, and execute an action corresponding to the machine interpretable event.

2. The system of claim 1, wherein the processing pipeline further includes an outlier detection module configured to confirm the first set of sensor data and/or derivatives of the first set of sensor data are not an outlier.

3. The system of claim 2, wherein the outlier detection module compares the first set of sensor data and/or the derivatives of the first set of sensor data to at least one statistical file, a first statistical file of the at least one statistical file includes a set of values, the set of values indicating a multi-variable distribution based on historical sensor data for known gestures.

4. The system of claim 3, wherein the outlier detection module uses the first statistical file during calibration and a second statistical file during inference.

5. The system of claim 4, wherein the first statistical file is based on data gathered from a population of users, and the second statistical file is based on calibration data gathered from the user during calibration.

6. The system of claim 1, wherein, to determine the first transformation to the ML model, the pre-process module is configured to:

determine, based on the sensor data or derivative thereof, that the wearable device is in a deviated state relative to the arm of the user, the deviated state being known to modify the sensor data received by the wearable device according to a known deviation pattern relative to the sensor data that would be received by the wearable device if the wearable device were in a neutral state; and based on the determined deviated state, determine the first transformation to the ML model, the determined first transformation to the ML model being configured to improve inference accuracy of the ML model while the wearable device is in the deviated state.

7. The system of claim 6, wherein the deviated state comprises a deviated arm posture that is different from a neutral arm posture when the wearable device is in a neutral state, and determining the first transformation to the ML model comprises:

determining, based on the motion data, that the arm of the user is in the deviated arm posture.

8. The system of claim 1, wherein the first transformation applies adjustments to one or more model parameters, wherein the model parameters include one or more of weights, biases, thresholds, or values of the ML model.

9. The system of claim 1, wherein, to determine the second transformation to the first set of sensor data, the pre-process module is configured to:

determine, based on the sensor data, that the wearable device is in a deviated state relative to the arm of the user, the deviated state being known to modify the sensor data received by the wearable device according to a known deviation pattern relative to the sensor data that would be received by the wearable device if the wearable device were in a neutral state; and based on the determined deviated state, determine the second transformation to the first set of sensor data, the determined second transformation to the first set of sensor data being configured produce the mapped sensor data, which is more similar to the sensor data that would be received by the wearable device if the wearable device were in the neutral state than is the first set of sensor data.

10. The system of claim 1, wherein the second transformation comprises a rotation, a translation, a projection, and/or a scaling, so that the first set of sensor data, as transformed to the mapped sensor data, is more similar to sensor data that would be received by the wearable device if the wearable device were in a neutral state.

11. The system of claim 1, wherein the ML model includes a first ML model to infer an IMU gesture inference based on the motion data, and a second ML model to infer a biopotential gesture inference based on the biopotential data and the motion data, and the inference module determines the gesture inference based on the IMU gesture inference and the biopotential gesture inference.

12. The system of claim 11, wherein the inference module is configured to:

store successive biopotential gesture inferences;

determine a threshold number of the successive biopotential gesture inferences have been stored; and determine the gesture inference based on the threshold number of the successive biopotential gesture inferences and probability information of a confusion matrix, the confusion matrix having been generated during training of the second ML model.

13. A computer-implemented method for gesture inference, the computer-implemented method comprising:

obtaining a first set of sensor data, the first set of sensor data including motion data and biopotential data, the motion data being obtained by a motion sensor of a wearable device, the motion sensor being configured to obtain the motion data relating to a motion of a portion of an arm of a user wearing the wearable device, the biopotential data being obtained by a biopotential sensor of the wearable device, the biopotential sensor being configured to obtain the biopotential data indicating electrical signals generated by nerves and muscles in the arm of the user;

determining, based on the sensor data or a derivative thereof, a first transformation to a ML model and/or a second transformation to the first set of sensor data;

applying the first transformation to the ML model to obtain a session ML model and/or applying the second transformation to the first set of sensor data or derivative thereof to obtain mapped sensor data; and inferring a gesture inference based on (1) the session ML model and the first set of sensor data, and/or (2) the ML model and the mapped sensor data;

wherein the wearable device is configured to, based on the gesture inference, determine a machine interpretable event, and execute an action corresponding to the machine interpretable event.

14. The computer-implemented method of claim 13, wherein, to determine the first transformation to the ML model, the computer-implemented method further includes:

determining, based on the sensor data or derivative thereof, that the wearable device is in a deviated state relative to the arm of the user, the deviated state being known to modify the sensor data received by the wearable device according to a known deviation pattern relative to the sensor data that would be received by the wearable device if the wearable device were in a neutral state; and based on the determined deviated state, determining the first transformation to the ML model, the determined first transformation to the ML model being configured to improve inference accuracy of the ML model while the wearable device is in the deviated state.

15. The computer-implemented method of claim 14, wherein the deviated state comprises a deviated arm posture that is different from a neutral arm posture when the wearable device is in a neutral state, and, to determine the first transformation to the ML model, the computer-implemented method further comprises:

determining, based on the motion data, that the arm of the user is in the deviated arm posture.

16. The computer-implemented method of claim 13, wherein the first transformation applies adjustments to one or more model parameters, wherein the model parameters include one or more of weights, biases, thresholds, or values of the ML model.

17. The computer-implemented method of claim 13, wherein, to determine the second transformation to the first set of sensor data, the computer-implemented method further includes:

determining, based on the sensor data, that the wearable device is in a deviated state relative to the arm of the user, the deviated state being known to modify the sensor data received by the wearable device according to a known deviation pattern relative to the sensor data that would be received by the wearable device if the wearable device were in a neutral state; and based on the determined deviated state, determining the second transformation to the first set of sensor data, the determined second transformation to the first set of sensor data being configured produce the mapped sensor data, which is more similar to the sensor data that would be received by the wearable device if the wearable device were in the neutral state than is the first set of sensor data.

18. The computer-implemented method of claim 13, wherein the second transformation comprises a rotation, a translation, a projection, and/or a scaling, so that the first set of sensor data, as transformed to the mapped sensor data, is more similar to sensor data that would be received by the wearable device if the wearable device were in a neutral state.

19. The computer-implemented method of claim 13, wherein the ML model includes a first ML model to infer an IMU gesture inference based on the motion data, and a second ML model to infer a biopotential gesture inference based on the biopotential data and the motion data, and the ML model determines the gesture inference based on the IMU gesture inference and the biopotential gesture inference.

20. The computer-implemented method of claim 19, wherein the computer-implemented method further includes:

storing successive biopotential gesture inferences;

determining a threshold number of the successive biopotential gesture inferences have been stored; and determining the gesture inference based on the threshold number of the successive biopotential gesture inferences and probability information of a confusion matrix, the confusion matrix having been generated during training of the second ML model.

* * * * *